United States Patent
Cernerud et al.

(10) Patent No.: US 7,244,722 B2
(45) Date of Patent: Jul. 17, 2007

(54) AMINO-SUBSTITUTED 1H-PYRAZIN-2-ONES AND 1H-QUINOXALIN-2-ONES

(75) Inventors: Magnus Cernerud, Stockholm (SE); Helena Lundström, Sundbyberg (SE); Björn M Nilsson, Stockholm (SE); Markus Thor, Knivsta (SE)

(73) Assignee: Biovitrum AB (SE)

( * ) Notice: Subject to any disclaimer, the term of this patent is extended or adjusted under 35 U.S.C. 154(b) by 132 days.

(21) Appl. No.: 10/622,055

(22) Filed: Jul. 17, 2003

(65) Prior Publication Data

US 2004/0063693 A1 Apr. 1, 2004

Related U.S. Application Data

(60) Provisional application No. 60/426,240, filed on Nov. 14, 2002.

(30) Foreign Application Priority Data

Jul. 19, 2002 (SE) .................................. 0202287

(51) Int. Cl.
- *A01N 43/00* (2006.01)
- *A01N 43/58* (2006.01)
- *A01N 43/60* (2006.01)
- *A61K 31/553* (2006.01)
- *C07D 241/02* (2006.01)

(52) U.S. Cl. ............. 514/211.15; 514/249; 514/252.11; 540/575; 540/598; 544/354; 544/357

(58) Field of Classification Search .................... None
See application file for complete search history.

(56) References Cited

U.S. PATENT DOCUMENTS

| | | | | |
|---|---|---|---|---|
| 4,163,849 | A | 8/1979 | Lumma, Jr. et al. | 544/357 |
| 5,134,149 | A | 7/1992 | Carr et al. | 514/317 |
| 5,538,974 | A | 7/1996 | Ogawa et al. | 514/253 |
| 6,143,792 | A | 11/2000 | Cattelin | 514/640 |
| 6,358,977 | B1 | 3/2002 | Carlsson | 514/317 |

FOREIGN PATENT DOCUMENTS

| | | |
|---|---|---|
| EP | 0522226 A1 | 12/1991 |
| EP | 0695545 A1 | 6/1995 |
| GB | 1440722 | 6/1976 |
| GB | 1492528 | 11/1977 |
| WO | WO 95/33721 | 12/1995 |
| WO | WO 00/12090 | 3/2000 |
| WO | WO 00/76984 | 12/2000 |
| WO | WO 01/89498 A2 | 11/2001 |

OTHER PUBLICATIONS de Angelis, "5-HT2A antagonists in psychiatric disorders" Current Opinion in Investigational Drugs, vol. 3(1), pp. 106-112 (2002).*
Kihara et al, "AT-1015, a Novel Serotonin (5-HT)2 Receptor Antagonist, Blocks Vascular and Platelet 5-HT2A Receptors and Prevents the Laurate-Induced Peripheral Vascular Lesion in Rats" Journal of Cardiovascular Pharmacology, vol. 35(4), pp. 523-530 (2000).*
Hans Bundgaard, Design of Prodrugs, p. 1. © 1985 Elsevier Science Publishers.*
Richard B. Silverman, The Organic Chemistry of Drug Design and Drug Action, pp. 352-400. © 1992 Academic Press, Inc.*
Al-Dabbagh and Smith, "Species differences in oxidative drug metabolism: some basic considerations." Archives of toxicology. Supplement. Archiv fur Toxikologie. supplement, vol. 7, pp. 219-231 (1984).*
Camras et al, "Efficacy and Adverse Effects of Medications Used in the Treatment of Glaucoma" Drugs & Aging, vol. 15(5), pp. 377-388 (Nov. 1999).*
Phelan Peter "Reappraising First-Line Treatment in Glaucoma Management" Hospital Medicine, vol. 63(9), pp. 540-545 (Sep. 2002).*
Webster's II New Riverside University Dictionary, p. 944 © 1994 Houghton Mifflin Company.*
Nilsson et al, "A behavioural pattern analysis of hypoglutamatergic mice—effects of four different antipsychotic agents" Journal of Neural Transmission, vol. 108, pp. 1181-1196 (2001).*
Manabu Hori et al., "Design and Syntheses of a Series of Novel Serotonin₃ Antagonists", *Chemical & Pharmaceutical Bulletin*, vol. 41, No. 10, pp. 1832-1841 (1993).
William C. Lumma, Jr., et al., "Piperazinylpyrazines with Central Serotoninmimetic Activity", *Journal of Medicinal Chemistry*, vol. 21, No. 6, pp. 536-542 (1978).
William C. Lumma, Jr., et al., "Piperazinylquinoxalines with Central Serotoninmimetic Activity", *Journal of Medicinal Chemistry*, vol. 24, No. 1, pp. 93-101 (1981).
Abbot, F.V., et al., "Activation of 5-HT$_{2A}$ Receptors Potentiates Pain Produced by Inflammatory Mediators", *Neuropharmacology*, vol. 35(1), pp. 99-110, 1996.

(Continued)

*Primary Examiner*—Zachary C. Tucker
(74) *Attorney, Agent, or Firm*—Fish & Richardson P.C.

(57) ABSTRACT

Compounds of the general formula (I):

(I)

wherein m, n, $R^1$, $R^2$, $R^3$ and $R^4$ are as described in the specification.

Further included are pharmaceutical compositions comprising the compounds, processes for their preparation, as well as the use of the compounds for the preparation of a medicament for the treatment of 5-HT$_{2A}$ receptor-related disorders or medical conditions.

33 Claims, No Drawings

OTHER PUBLICATIONS

Apelqvist, J., et al., "Ketanserin in the treatment of diabetic foot ulcer with severe peripheral vascular disease", *International Angiology*, vol. 9, pp. 120-124, 1990.

Bush, L.R., et al., "The Role of the Endothelium in Arterial Thrombosis and the Influence of Antithrombotic Therapy", *Drug Development Research*, vol. 7, pp. 319-340, 1986.

Cohen, M.L., "Canine, but not rat bladder contracts to serotonin via activation of 5HT$_2$ receptors", *The Journal of Urology*, vol. 143, pp. 1037-1040, 1990.

Costagliola, C., et al., "Effect of tropical ketanserin administration on intraocular pressure", *British Journal of Ophthalmology*, vol. 77, pp. 344-348, 1993.

Danton, G., et al., "Endothelium-targeted pharmacotherapeutics for the treatment of stroke", *Current Opinion in Investigational Drugs*, vol. 3(6), pp. 896-904, 2002.

Dietrich, W.D., et al., "Effect of the serotonin antagonist ketanserin on the hemodynamic and morphological consequences of thrombotic infarction", *Journal of Cerebral Blood Flow and Metabolism*, vol. 9, pp. 812-820, 1989.

Dursun, S.M., et al., "An exploratory approach to the serotonergic hypothesis of depression: bridging the synaptic gap", *Medical Hypotheses*, vol. 56(2), pp. 235-243, 2001.

Furukawa, K., et al., "Therapeutic effects of sarpogrelate hydrochloride (MCI-9042) on chronic arterial occlusive diseases: a double-blind comparison with ticlopidine hydrochloride", *J. Clin. Ther. Med.* 1991, 7, 1747-1770.

Gelders, Y.G., "Thymosthenic agents, a novel approach in the treatment of schizophrenia", *British Journal of Psychiatry*, vol. 155(suppl.), pp. 33-36, 1989.

Hara, N., et al., "Antithrombotic effect of MCI-9042, a new antiplatelet agent on experimental thrombosis models", *Thrombosis and Haemostasis*, vol. 66(4), pp. 484-488, 1991.

Hemmeter, U., et al., "Schlafstorungen bei chronischen schmerzen und generalisierter tendomyopathie", *Schweiz Med Wochenschr*, vol. 125, pp. 2391-2397, 1995. (Abstract Only).

Hotta, N., et al., "Effects of the 5-HT$_{2A}$ receptor antagonist sarpogrelate in diabetic patients with complications", *Clin Drug Invest*, vol. 18(3), pp. 199-207, 1999.

Ichiyanagi, N., et al., "Changed responsiveness of the detrusor in rabbits with alloxan induced hyperglycemia: Possible role of 5-hydroxytryptamine for diabetic bladder dysfunction", *The Journal of Urology*, vol. 168, pp. 303-307, 2002.

Ishimura, E., et al., "Therapeutic effect of sarpogrelate, a new 5-hydroxytryptamine receptor 2A antagonist, on diabetic nephropathy and neuropathy", *Nephron*, vol. 76, pp. 227-229, 1997.

Jackson, J., et al., "Enhancement of [m-methoxy 3H]MDL100907 binding to 5HT$_{2A}$ receptors in cerebral cortex and brain stem of streptozotocin induced diabetic rats", *Molecular and Cellular Biochemistry*, vol. 199, pp. 81-85, 1999.

Kaplan, S.A., et al., "Urodynamic findings in patients with diabetic cystopathy", *The Journal of Urology*, vol. 153, pp. 342-344, 1995.

Kihara, H., et al., "Antithrombotic activity of AT-1015, a potent 5-HT$_{2A}$ receptor antagonist, in rat arterial thrombosis model and its effect on bleeding time", *European Journal of Pharmacology*, vol. 433, pp. 157-162, 2001.

Kim, H.J., et al., "Acute effects of serotonin on rat bladder contractility", *Urologia Internationalis*, vol. 68, pp. 44-48, 2002.

Kobori, S., et al., "Effect of 5-hydroxytryptamine$_{2A}$ receptor antagonist on the development of diabetic nephropathy in early stage", *Diabetes Mellitus: Recent Advances for the 21$^{st}$ Century*, pp. 283-286, 2000.

Kodama, M., et al., "Influence of 5-hydroxytrytamine and the effect of a new serotonin receptor antagonist (sarpogrelate) on detrusor smooth muscle of streptozotocin-induced diabetes mellitus in the rat", *International Journal of Urology*, vol. 7, pp. 231-235, 2000.

Leysen, D., et al., "5-HT$_2$ antagonists: a concept for the treatment of schizophrenia", *Current Pharmaceutical Design*, vol. 3, pp. 367-390, 1997.

Malyszko, J., et al., "Daily variations of platelet aggregation in relation to blood and plasma serotonin in diabetes", *Thrombosis Research*, vol. 75(5), pp. 569-576, 1994.

Mano, T., et al., "The effect of anplag (sarpogrelate HCI), new selective 5-HT$_2$ antagonist on intraocular pressure in rabbits", *Investigative Ophthalmology & Visual Science*, vol. 36(4), pp. 3322-3309, 1995.

Martinzez-De Jesus, F.R., et al., "Randomized single-blind trial of topical ketanserin for healing acceleration of diabetic foot ulcers", *Archives of Medical Research*, vol. 28(1), pp. 95-99, 1997.

Menendez, V., et al., "Urodynamic evaluation in simultaneous insulin-dependent diabetes mellitus and end stage renal disease", *The Journal of Urology*, vol. 155, pp. 2001-2004, 1996.

Mermoud, A., et al., "Le traitment du glaucoma a pression normale avec un antagoniste des recepteurs S2 del la serotonine, le naftidrofuryl (praxilen)", *Klin. Mbl. Augenheilk.*, vol. 198, pp. 332-334, 1991.

Mermoud, A., et al., "Double-blind study in the treatment of normal tension glaucoma with naftidrofuryl", *Opthalmologica*, vol. 201, pp. 145-151, 1990.

Nabeshima, T., et al., "Effect of naftidrofuryl oxalate on 5-HT$_2$ receptors in mouse brain: evaluation based on quantitative autoradiography and head-twitch response", *European Journal of Pharmacology*, vol. 223, pp. 109-115, 1992.

Obata, H., et al., "Antinociception in rat by sarpogrelate, a selective 5-HT$_{2A}$ receptor antagonist, is peripheral", *European Journal of Pharmacology*, vol. 404, pp. 95-102, 2000.

Ogawa, S., et al., "The 5-HT$_2$ receptor antagonist sarpogrelate reduces urinary and plasma levels of thromboxane A2 and urinary albumin excretion in non-insulin-dependent diabetes mellitus patients", *Clinical and Experimental Pharmacology and Physiology*, vol. 26, pp. 461-464, 1999.

Otake, T., et al., "Bone atrophy in complex regional pain syndrome patients measured by microdensitometry", *Canadian Journal of Anesthesiology*, vol. 45(9), pp. 831-838, 1998.

Pietraszek, M.H., et al., "Blood serotonergic mechanisms in type 2 (non-insulin-dependent) diabetes mellitus", *Thrombosis Research*, vol. 66, pp. 765-774, 1992.

Pietraszek, M.H., et al., "Enhanced platelet response to serotonin in diabetes mellitus in relationship to vascular complications", *Thromb. Haemost.* 1991, 65, 985 (Abstract Only).

Pietraszek, M.H., et al., "The effect of MCI-9042 on serotonin-induced platelet aggregation in type 2 diabetes mellitus", *Thrombosis Research*, vol. 70, pp. 131-138, 1993.

Radulovacki, M., et al., "Ketanserin, a 5-HT$_2$ receptor antagonist, reduces sleep apneas in rats", *Research Communications in Biological Psychology and Psychiatry*, 26 (1,2), 2001.

Robertson, S.C., et al., "Effects of serotonin (5-HT) and selective 5-HT receptor antagonists on regional cerebral blood flow after middle cerebral artery occlusion", *Surgical Forum*, pp. 561-563.

Saxena, P.R., et al., "Excitatory 5-hydroxytryptamine receptors in the cat urinary bladder are of the M- and 5-HT2-type", *Journal of Autonomic Pharmacology*, vol. 5, pp. 101-107, 1985.

Schechter, L.E., et al., "Serotonergic antidepressants: current and future perspectives", *CPNS Investigational Drugs*, vol. 7(4), pp. 432-447, 1999.

Sorbera, L.A., et al., "MDL-100907", *Drugs of the Future*, vol. 23(9), pp. 955-965, 1998.

Stratz, T., et al., "Blockierung der S2-rezeptoren—ein neues behandlungspringzip der generlisierten tendomyopathie (fibromyalgie)?", *Zeitschrift fur Rheumatologie*, vol. 50, pp. 21-22, 1991. (Abstract Only).

Sugimoto, S., et al., "Characteristics of 5-HT$_{2A}$ receptors in the bladder smooth muscle of diabetic rats", *Nihon. Univ. J. Med.*, vol. 43, pp. 141-152, 2001.

Sumiyoshi, T., et al., "The effect of streptozotocin-induced diabetes on dopamine2, serotonin 1A, and serotonin 2A receptors in the rat brain", *Neuropsychopharmacology*, vol. 16(3), 183-190, 1997.

Takei, I., et al., "Effects of the 5-HT$_2$ receptor antagonist sarpogrelate on diabetic vascular disease", *Diabetes Research*, vol. 34, pp. 239-246, 1999.

Takenaka, H., et al., "The effect of anglag (saprogrepalte HCL), novel selective 5-HT$_2$ antagonist on intraocular presser in glaucoma patients", *Invest. Ophthalmol. Vis. Sci.* 1995, 36, S734. (Abstract Only).

Takimoto, Y., et al., "The effect of 5-HT$_2$antagonist for urinary frequency symptom on diabetes mellitus patients", *Jpn. J. Urol.* vol. 90(8), pp. 731-740, 1999. (Abstract Only).

Tammela, T.L.J., et al., "Temporal changes in micturition and bladder contractility after sucrose diuresis and streptozotocin-induced diabetes mellitus in rats", *The Journal of Urology*, vol. 153, pp. 2014-2021 1995.

Tokunaga, A., et al., "5-HT$_{2A}$ receptor subtype is involved in the thermal hyperalgesic mechanism of serotonin in the periphery", *Pain*, vol. 76, pp. 349-355, 1998.

Viola, A.U., et al., "Ritaserin, a serotonin-2 receptor antagonist, improves ultradian sleep rhythmicity in young poor sleepers", *Clinical Neurophysiology*, vol. 113, pp. 429-434, 2002.

Weinberger, D.R., et al., "Cognitive function in schizophrenia", *International Clinical Psychopharmacology*, vol. 12(supp.), pp. S29-S36, 1997.

Yoshida, A., et al., "5-hydroxytryptamine receptors, especially the 5-HT$_4$ receptor, in guinea pig urinary bladder", *Jpn. J. Pharmacol.*, vol. 89, pp. 349-355, 2002.

\* cited by examiner

AMINO-SUBSTITUTED 1H-PYRAZIN-2-ONES AND 1H-QUINOXALIN-2-ONES

RELATED APPLICATIONS

This application claims priority to Swedish application number 0202287-9, filed on Jul. 19, 2002, and U.S. provisional application No. 60/426,240, filed on Nov. 14, 2002, the contents of which are incorporated herein by reference.

TECHNICAL FIELD

The present invention relates to novel compounds, to pharmaceutical compositions comprising the compounds, to processes for their preparation, as well as to the use of the compounds for the preparation of a medicament.

BACKGROUND ART

Many disorders and conditions of the central nervous system are influenced by the serotonergic neurotransmitter system. For example, serotonin (5-hydroxytryptamine; 5-HT) has been implicated in a number of disorders and conditions that originate in the central nervous system. The serotonin receptors are divided into seven main classes $5\text{-}HT_1\text{-}5\text{-}HT_7$. Additionally, the $5\text{-}HT_2$ family of serotonin receptors is subdivided into the $5\text{-}HT_{2A}$, $5\text{-}HT_{2B}$ and $5\text{-}HT_{2C}$ receptor subtypes. For reviews dealing with the classification and function characteristics of serotonin receptors, see for example: Hoyer, D. et al. Pharmacol. Rev. 1994, 46, 157-203; Saxena, P. R. Pharmacol. Ther. 1995, 66, 339-368; Barnes, N. M. et al. Neuropharmacol. 1999, 38, 1083-1152; Roth, B. L. et al. Pharmacol. Ther. 1998, 79, 231-257.

The $5\text{-}HT_{2A}$ receptor subtype is expressed in the human brain, including many cortical, limbic, and forebrain regions and is postulated to be involved in the modulation of higher cognitive and affective functions. The $5\text{-}HT_{2A}$ receptor subtype is also expressed on mature blood platelets where it mediates, in part, platelet aggregation, one of the initial steps in the process of vascular thrombosis. Several lines of evidence strongly implicate the $5\text{-}HT_{2A}$ receptor subtype in the etiology of such medical conditions as hypertension, thrombosis, migraine, vasospasm, ischemia, depression, anxiety, schizophrenia, obsessive-compulsive disorder, sexual function disorders, sleep disorders, and eating disorders, such as anorexia nervosa. They may further be effective in the lowering of intraocular pressure and may therefore be beneficial in treating glaucoma (cf. T. Mano et al. and H. Takaneka et al., Invest. Ophthalmol. Vis Sci. 1995, 36, 719 and 734, respectively). The compound (+)-α-(2,3-dimethoxyphenyl)-1-[2-(4-fluorophenyl)-ethyl]-4-piperidinemethanol (also known as M-100907) has been shown to be a potent antagonist of human $5\text{-}HT_{2A}$ receptors and is described in WO 91/18602.

The $5\text{-}HT_{2A}$ receptor subtype has further been suggested to be involved in urological disorders such as diabetic nephropathy and urinary incontinence (diabetic nephropathy, see: Ishimura, E. et al. Nephron 1997, 76, 227-229; urinary incontinence, including coexisting diabetes, see: Kodama, M. et al. Int. J. Urol 2000, 7, 231-235 and Ichiyanagi, N. et al. J. Urol. 2002, 168, 303-307).

Compounds that have an effect on the $5\text{-}HT_{2A}$ receptor may therefore have a therapeutic potential in the treatment of disorders like those mentioned above.

Information Disclosure

Various classes of compounds have been disclosed to act as antagonists at the $5\text{-}HT_{2A}$ receptor. For example, 4-aryl- or 4-heteroarylpiperazines such as those described in J. Med. Chem. 1991, 34, 2477, Chem. Pharm. Bull. 1987, 35, 1919-, Bioorg. Med. Chem. Lett. 1997, 7, 1635-1638, and Arch. Pharm. 1995, 328, 659-666. Other compound classes reported to act as $5\text{-}HT_{2A}$ antagonists are disclosed in WO 0114332, WO 0004017, WO 0043362, WO 0107434, WO 0107435 and WO 0151469. A further class of $5\text{-}HT_{2A}$ antagonists is represented by the N-aralkyl-piperidinemethanol derivatives disclosed in U.S. Pat. No. 5,169,096, encompassing M-100907 mentioned above. The class of $5\text{-}HT_{2A}$ antagonists disclosed in U.S. Pat. No. 5,169,096 are claimed to be useful in the treatment of a variety of disease states such as anorexia nervosa, variant angina, Raynaud's phenomenon, coronary vasospasms, hypertension, profylactic treatment of migraine, cardiovascular diseases such as hypertension, peripheral vascular disease, thrombotic episodes, cardiopulmonary emergencies and arrythmias, and has anesthetic properties. See also U.S. Pat. No. 4,877,798 (fibromyalgia); U.S. Pat. No. 4,908,369 (insomnia); U.S. Pat. No. 5,106,855 (glaucoma); U.S. Pat. No. 6,004,980 (anxiety, Raynaud's phenomenon, cardiac arrythmia; extrapyramidal symptoms; drug abuse, anorexia, fibromyalgia); EP 337136 (treatment of extrapyramidal side effects associated with neuroleptic therapy). Psychotic illness such as schizophrenia and mania, among other indications are disclosed uses for M-100907 in U.S. Pat. No. 5,134,149. The use of M-100907 for the treatment of various developmental neurological disorders such as autism and attention deficit hyperactivity disorder is disclosed in WO 99/56750. The use of M-100907, and prodrugs thereof, for the treatment of symptoms of dementia, such as Alzheimer's disease, is disclosed in WO 01/89498. The use of M-100907 for the treatment of obsessive-compulsive disorders (OCD) is disclosed in U.S. Pat. No. 5,618,824.

Ketanserin (3-[2-[4-(4-fluorobenzoyl)-1-piperidinyl] ethyl]-2,4(1H,3H)-quinazolinedione is a $5\text{-}HT_{2A}$ antagonist that has been on certain markets for hypertension and is patented by Janssen in EP 13612 B. The use of ketanserin for the treatment of glaucoma is disclosed in EP 522226 (cf. Ophthalmologica 2001, 215, 419-423).

Sarpogrelate (butanedioic acid, mono[2-(dimethylamino)-1-[[2-[2-(3-methoxyphenyl)ethyl]phenoxy]methyl] ethyl]ester, MCI-9042; Anplag™), Mitsubishi, Japan, is a $5\text{-}HT_{2A}$ antagonist used for the treatment of thromboembolism in Japan and is disclosed in EP 72942 B. The use of sarpogrelate for the treatment of glaucoma is disclosed by Mitsubishi in EP 695545 and by Senju Pharmaceutical in CA 2144810. Sarpogrelate is also reported to have therapeutic potential in the treatment of diabetic complications (cf. Hotta, N. et al. Clin. Drug Invest. 1999, 18, 199-207; Kobori, S. et al. Int. Congr. Ser. 2000, 1209, 283-286).

The $5\text{-}HT_{2A}$ antagonist amperozide (4-(4,4-bis(4-fluorophenyl)butyl)-N-ethyl-1-piperazinecarboxamide) has been disclosed to possess antipsychotic properties and was first claimed by Pharmacia's subsidiary Ferrosan in the patent DE 02941880. Its use for the treatment of substance abuse is disclosed in the associated patent WO 09216211.

Ajinomoto is developing the $5\text{-}HT_{2A}$ antagonist and platelet aggregation inhibitor, AT-1015 (N-[2-{4-(5H-dibenzo[a, d]cyclohepten-5-ylidene)piperidino}-ethyl]-1-formyl-4-piperidinecarboxamide monohydrochloride monohydrate) for the potential treatment of thrombotic conditions (cf. European Journal of Pharmacology 2001, 433(2-3), 157-162).

Senju Pharmaceuticals has disclosed a series of 1,5-benzoxa-thiepine derivatives (e.g., methyl 7-methoxy-3-oxo-3,4-dihydro-2H-1,5-benzoxathiepin-4-carboxylate) in U.S. Pat. No. 5,538,974 and which are stated to be serotonin $S_2$ receptor antagonists and being useful for the treatment of glaucoma.

WO 00/64441 discloses, inter alia, a series of known 5-HT$_{2A}$ antagonists (e.g., M-100907) for therapeutic or prophylactic treatment of disorders involving bronchoconstriction.

Some structurally related compounds to those of formula (I) in the present invention are disclosed in J. Med. Chem. 1981, 24, 93-101 and in GB 1,440,722. Particular compounds are 3-piperazin-1-yl-1H-quinoxalin-2-one, 1-methyl-3-piperazin-1-yl-1H-quinoxalin-2-one, 3-(4-methyl-piperazin-1-yl)-1H-quinoxalin-2-one, and 3-(1-piperazinyl)-1-[2-(dimethylamino)-ethyl]-2(1H)-quinoxalinone. 1-Benzyl-3-(4-methyl-piperazin-1-yl)-1H-quinoxalin-2-one is disclosed in Chem. Pharm. Bull. 1993, 41, 1832-1841. WO 00/76984 discloses pyrazinyl ether compounds that bind to the 5-HT$_{2C}$ receptor.

SUMMARY OF THE INVENTION

The present invention provides a new class of antagonists of the human 5-HT$_{2A}$ receptor of general formula (I):

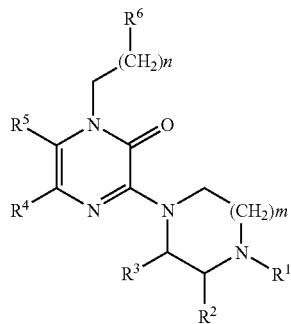

(I)

wherein
m represents 1 or 2;
n represents 0, 1, 2, 3, or 4;
$R^1$ is H or $C_{1-6}$-alkyl, aryl-$C_1$-$C_3$-alkyl, heteroaryl-$C_1$-$C_3$-alkyl, 2-hydroxyethyl, methoxy-$C_2$-$C_4$-alkyl, $C_1$-$C_4$-alkoxy-carbonyl, aryloxy-$C_2$-$C_3$-alkyl, or heteroaryloxy-$C_2$-$C_3$-alkyl; wherein
   any aryl or heteroaryl residue may be substituted with $C_{1-4}$-alkyl, $C_{1-4}$-alkoxy, $C_{1-4}$-alkylthio, halogen, trifluoromethyl, trifluoromethoxy or cyano;
$R^2$ and $R^3$ each, independently, represent H or $CH_3$;
$R^4$ and $R^5$ each, independently, represent H, halogen, methyl, or together with the ring, to which carbon atoms they are attached, form a 1H-quinoxalin-2-one nucleus; and
$R^6$ represents aryloxy, heteroaryloxy, arylthio, heteroarylthio, aryl-NH, heteroaryl-NH, aryl, arylcarbonyl, heteroaryl, or heteroarylcarbonyl; wherein
   any aryl or heteroaryl residue, alone or as part of another group, may be unsubstituted or substituted. Where substituted, one, two, three, four or five substituents may be present, preferably one or two for non-halogen substituents, and are independently selected from aryl, aryl-$C_{1-2}$-alkyl, arylcarbonyl, heteroaryl, heteroaryl-$C_{1-2}$-alkyl, heteroarylcarbonyl, aryloxy, heteroaryloxy, arylthio, heteroarylthio, arylamino, heteroarylamino, $C_{3-6}$-cycloalkyl, $C_{3-6}$-cycloalkyloxy, $C_{3-6}$-cycloalkyl-carbonyl, $C_{1-6}$-alkyl, $C_{2-6}$-alkanoyl, $C_{2-6}$-alkynyl, $C_{2-6}$-alkenyl, or fluoro-$C_{2-4}$-alkyloxy, halogen, trifluoromethyl, nitro, cyano, trifluoromethoxy, trifluoromethylthio, $C_{1-6}$-alkoxy, $C_{1-6}$-alkylthio, $C_{1-6}$-alkylamino, $C_{1-4}$-dialkylamino, hydroxy or oxo;
wherein
   any aryl or heteroaryl residue as substituents on aryl or heteroaryl, alone or as part of another group, in turn may be substituted in one, two, three, four or five positions, preferably one, independently of each other by $C_{1-4}$-alkyl, $C_{1-4}$-alkoxy, $C_{1-4}$-alkylthio, halogen, trifluoromethyl, trifluoromethoxy, or cyano;
and pharmaceutically acceptable salts, hydrates, geometrical isomers, tautomers, optical isomers, N-oxides and prodrug forms thereof, with the provisos that:
   $R^2$ and $R^3$ are not both $CH_3$;
   when $R^1$, $R^2$, $R^4$ and $R^5$ are H and $R^3$ is H or $CH_3$, then $R^6$ is not 3-pyridyloxy, 6-methyl-2-nitro-3-pyridyloxy, or 2-chloro-3-pyridyloxy;
   when n=0, then $R^6$ is not aryloxy, heteroaryloxy, arylthio, heteroarylthio, aryl-NH or heteroaryl-NH; and
   the compound of formula (I) is not 1-benzyl-3-(4-methyl-piperazin-1-yl)-1H-quinoxalin-2-one.

The compounds of the present invention may be regarded as structural isomers of compounds represented by formula (Ib), wherein $X_1$ is O, disclosed in WO 00/76984.

In case the compounds of formula (I) can be in the form of optical isomers, the invention comprises the racemic mixture as well as the individual enantiomers as such.

In case the compounds of formula (I) contain groups, which may exist in tautomeric forms, the invention comprises the tautomeric forms of the compounds as well as mixtures thereof.

In case the compounds of formula (I) can be in the form of geometrical isomers, the invention comprises the geometrical isomers as well as mixtures thereof.

According to another aspect, the invention provides the compounds according to formula (I) above for use in therapy in a number of disease states, including those delineated herein.

Still another aspect of the invention provides a pharmaceutical composition comprising a compound according to formula (I) above as the active ingredient, preferably together with a pharmaceutically acceptable carrier and, if desired, other pharmacologically active agents.

In yet another aspect, the invention provides a method for the treatment of a human or animal subject suffering from a serotonin-related disorder or medical condition, particularly 5-HT$_{2A}$ receptor-related, such as angina, Raynaud's phenomenon, intermittent claudication, coronary or peripheral vasospasms, hypertension, fibromyalgia, thrombotic illness (including stroke), memory disorders, such as Alzheimer's disease; schizophrenia; obsessive-compulsive disorder; mood disorders; autism; attention deficit hyperactivity disorder (ADHD); anxiety disorders; depression disorders (including depression with coexisting diabetes), sexual function disorders, sleep disorders such as insomnia and sleep apnea, pain; substance abuse; extrapyramidal symptoms (e.g., associated with neuroleptic drug therapy using drugs such as, for example, haloperidol and chlorpromazine); Parkinson's disease; glaucoma including normal tension glaucoma; urinary incontinence including urinary incontinence with co-existing diabetes; menopausal and postmenopausal hot flushes; premenstrual syndrome; bronchoconstriction disorders, such as asthma and chronic obstructive pulmonary disease; eating disorders, such as binge eating disorders, anorexia nervosa and bulimia; diabetic complications such as nephropathy, neuropathy and retinopathy.

The method includes administering to a subject (e.g., a mammal, a human, a horse, a dog, or a cat) in need thereof (e.g., identified as in need thereof) an effective amount of one or more compounds of formula (I),

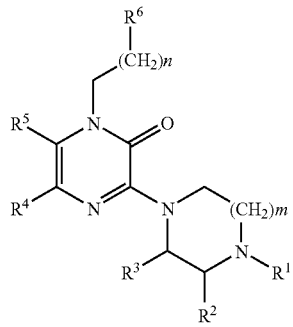

(I)

wherein
  m represents 1 or 2;
  n represents 0, 1, 2, 3, or 4;
  $R^1$ is H or $C_{1-6}$-alkyl, aryl-$C_1$-$C_3$-alkyl, heteroaryl-$C_1$-$C_3$-alkyl, 2-hydroxyethyl, methoxy-$C_2$-$C_4$-alkyl, $C_1$-$C_4$-alkoxycarbonyl, aryloxy-$C_2$-$C_3$-alkyl, or heteroaryloxy-$C_2$-$C_3$-alkyl; wherein
    any aryl or heteroaryl residue may be substituted with $C_{1-4}$-alkyl, $C_{1-4}$-alkoxy, $C_{1-4}$-alkylthio, halogen, trifluoromethyl, trifluoromethoxy or cyano;
  $R^2$ and $R^3$ each, independently, represent H or $CH_3$;
  $R^4$ and $R^5$ each, independently, represent H, halogen, methyl, or together with the ring, to which carbon atoms they are attached, form a 1H-quinoxalin-2-one nucleus; and
  $R^6$ represents aryloxy, heteroaryloxy, arylthio, heteroarylthio, aryl-NH, heteroaryl-NH, aryl, arylcarbonyl, heteroaryl, or heteroarylcarbonyl; wherein
    any aryl or heteroaryl residue, alone or as part of another group, may be unsubstituted or substituted. Where substituted, one, two, three, four or five substituents may be present, preferably one or two for non-halogen substituents, and are independently selected from aryl, aryl-$C_{1-2}$-alkyl, arylcarbonyl, heteroaryl, heteroaryl-$C_{1-2}$-alkyl, heteroarylcarbonyl, aryloxy, heteroaryloxy, arylthio, heteroarylthio, arylamino, heteroarylamino, $C_{3-6}$-cycloalkyl, $C_{3-6}$-cycloalkyloxy, $C_{3-6}$-cycloalkylcarbonyl, $C_{1-6}$-alkyl, $C_{2-6}$-alkanoyl, $C_{2-6}$-alkynyl, $C_{2-6}$-alkenyl, or fluoro-$C_{2-4}$-alkyloxy, halogen, trifluoromethyl, nitro, cyano, trifluoromethoxy, trifluoromethylthio, $C_{1-6}$-alkoxy, $C_{1-6}$-alkylthio, $C_{1-6}$-alkylamino, $C_{1-4}$-dialkylamino, hydroxy or oxo; wherein
      any aryl or heteroaryl residue as substituents on aryl or heteroaryl, alone or as part of another group, in turn may be substituted in one, two, three, four or five positions, preferably one, independently of each other by $C_{1-4}$-alkyl, $C_{1-4}$-alkoxy, $C_{1-4}$-alkylthio, halogen, trifluoromethyl, trifluoromethoxy, or cyano;
  and pharmaceutically acceptable salts, hydrates, geometrical isomers, tautomers, optical isomers, N-oxides and prodrug forms thereof, with the provisos that:
    $R^2$ and $R^3$ are not both $CH_3$;
    when $R^1$, $R^2$, $R^4$ and $R^5$ are H and $R^3$ is H or $CH_3$, then $R^6$ is not 3-pyridyloxy, 6-methyl-2-nitro-3-pyridyloxy, or 2-chloro-3-pyridyloxy;
    when n=0, then $R^6$ is not aryloxy, heteroaryloxy, arylthio, heteroarylthio, aryl-NH or heteroaryl-NH.

Another aspect of the invention relates to the use of the compounds of formula (I) for the manufacture of a medicament for the treatment of a serotonin-related disorder or medical condition, particularly 5-$HT_{2A}$ receptor-related, such as angina, Raynaud's phenomenon, intermittent claudication, coronary or peripheral vasospasms, hypertension, fibromyalgia, thrombotic illness (including stroke), memory disorders, such as Alzheimer's disease; schizophrenia; obsessive-compulsive disorder; mood disorders; autism; attention deficit hyperactivity disorder (ADHD); anxiety disorders; depression disorders (including depression with coexisting diabetes), sexual function disorders, sleep disorder, such as insomnia and sleep apnea, pain; substance abuse; extrapyramidal symptoms (e.g., associated with neuroleptic drug therapy using drugs such as, for example, haloperidol and chlorpromazine); Parkinson's disease; glaucoma including normal tension glaucoma; urinary incontinence including urinary incontinence with co-existing diabetes; menopausal and post-menopausal hot flushes; premenstrual syndrome; bronchoconstriction disorders, such as asthma and chronic obstructive pulmonary disease; eating disorders, such as binge eating disorders, anorexia nervosa and bulimia; diabetic complications such as nephropathy, neuropathy and retinopathy.

The methods delineated herein can also include the step of identifying that the subject is in need of treatment of the aforementioned diseases.

Finally a method for modulating 5-$HT_{2A}$ receptor function is an aspect of the invention.

This invention features a method of making a compound of formula (I), wherein $R^6$ is selected from aryloxy, heteroaryloxy, arylthio, heteroarylthio, aryl-NH, or heteroaryl-NH,
  by reacting a compound of the following formula (II):

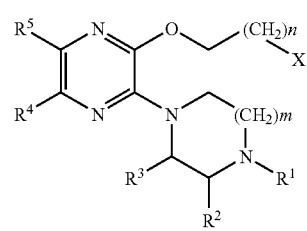

(II)

wherein
  m is 1 or 2;
  n is 1 or 2;
  X is OH;
  $R^1$ is H or $C_{1-6}$-alkyl, aryl-$C_1$-$C_3$-alkyl, heteroaryl-$C_1$-$C_3$-alkyl, 2-hydroxyethyl, methoxy-$C_2$-$C_4$-alkyl, $C_1$-$C_4$-alkoxycarbonyl, aryloxy-$C_2$-$C_3$-alkyl, or heteroaryloxy-$C_2$-$C_3$-alkyl; wherein
    any aryl or heteroaryl residue may be substituted with $C_{1-4}$-alkyl, $C_{1-4}$-alkoxy, $C_{1-4}$-alkylthio, halogen, trifluoromethyl, trifluoromethoxy or cyano;
  $R^2$ and $R^3$ each, independently, represent H or $CH_3$;
  $R^4$ and $R^5$ each, independently, represent H, halogen, methyl, or together with the ring, to which carbon atoms they are attached, form a 1H-quinoxalin-2-one nucleus;
  with an optionally substituted phenol or thiophenol; in a solvent.

This invention further features a method of preparing a compound of formula (I), wherein $R^6$ is selected from aryloxy, heteroaryloxy, arylthio, heteroarylthio, aryl-NH, heteroaryl-NH, aryl, arylcarbonyl, heteroaryl, or heteroarylcarbonyl, by reacting a compound of the following formula (IV),

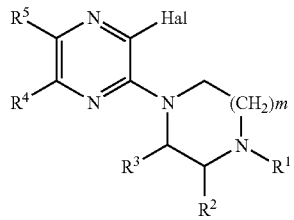

wherein
m is 1 or 2;
Hal is halogen;
$R^1$ is H or $C_{1-6}$-alkyl, aryl-$C_1$-$C_3$-alkyl, heteroaryl-$C_1$-$C_3$-alkyl, 2-hydroxyethyl, methoxy-$C_2$-$C_4$-alkyl, $C_1$-$C_4$-alkoxycarbonyl, aryloxy-$C_2$-$C_3$-alkyl, or heteroaryloxy-$C_2$-$C_3$-alkyl; wherein
  any aryl or heteroaryl residue may be substituted with $C_{1-4}$-alkyl, $C_{1-4}$-alkoxy, $C_{1-4}$-alkylthio, halogen, trifluoromethyl, trifluoromethoxy or cyano;
$R^2$ and $R^3$ each, independently, represent H or $CH_3$;
$R^4$ and $R^5$ each, independently, represent H, halogen, methyl, or together with the ring, to which carbon atoms they are attached, form a 1H-quinoxalin-2-one nucleus;
with an alkali metal or alkaline earth metal basic salt (e.g., in aqueous media) to produce a compound of formula (V),

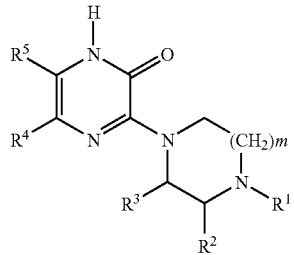

wherein
m is 1 or 2;
$R^1$ is H or $C_{1-6}$-alkyl, aryl-$C_1$-$C_3$-alkyl, heteroaryl-$C_1$-$C_3$-alkyl, 2-hydroxyethyl, methoxy-$C_2$-$C_4$-alkyl, $C_1$-$C_4$-alkoxycarbonyl, aryloxy-$C_2$-$C_3$-alkyl, or heteroaryloxy-$C_2$-$C_3$-alkyl; wherein
  any aryl or heteroaryl residue may be substituted with $C_{1-4}$-alkyl, $C_{1-4}$-alkoxy, $C_{1-4}$-alkylthio, halogen, trifluoromethyl, trifluoromethoxy or cyano;
$R^2$ and $R^3$ each, independently, represent H or $CH_3$; and
$R^4$ and $R^5$ each, independently, represent H, halogen, methyl, or together with the ring, to which carbon atoms they are attached, form a 1H-quinoxalin-2-one nucleus;

followed by N-alkylation of the compound of formula (V) by reaction with a compound of formula (VI), $$R^6-CH_2-(CH_2)_n-Y \quad (VI)$$

wherein
n is 0, 1, 2, 3 or 4;
Y is a leaving group; and $R^6$ represents aryloxy, heteroaryloxy, arylthio, heteroarylthio, aryl-NH, heteroaryl-NH, aryl, arylcarbonyl, heteroaryl, or heteroarylcarbonyl; and
wherein any aryl or heteroaryl residue, alone or as part of another group is unsubstituted or substituted. Where substituted, one, two, three, four or five substitutents may be present, preferably on or two for non-halogen substituents, and are independently selected from aryl, aryl-$C_{1-2}$-alkyl, arylcarbonyl, heteroaryl, heteroaryl-$C_{1-2}$-alkyl, heteroarylcarbonyl, aryloxy, heteroaryloxy, arylthio, heteroarylthio, arylamino, heteroarylamino, $C_{3-6}$-cycloalkyl, $C_{3-6}$-cycloalkyloxy, $C_{3-6}$-cycloalkylcarbonyl, $C_{1-6}$-alkyl, $C_{2-6}$-alkanoyl, $C_{2-6}$-alkynyl, $C_{2-6}$-alkenyl, or fluoro-$C_{2-4}$-alkyloxy, halogen, trifluoromethyl, nitro, cyano, trifluoromethoxy, trifluoromethylthio, $C_{1-6}$-alkoxy, $C_{1-6}$-alkylthio, $C_{1-6}$-alkylamino, $C_{1-4}$-dialkylamino, hydroxy or oxo;
wherein any aryl or heteroaryl residue as substituents on aryl or heteroaryl, alone or as part of another group, in turn is optionally substituted in one or more positions, preferably one, independently of each other by $C_{1-4}$-alkyl, $C_{1-4}$-alkoxy, $C_{1-4}$-alkylthio, halogen, trifluoromethyl, trifluoromethoxy, or cyano; in the presence of a base in a suitable solvent at an elevated temperature.

DETAILED DESCRIPTION OF THE INVENTION

According to the present invention, a class of novel compounds that bind to the human 5-$HT_{2A}$ receptor has been developed. The compounds act as receptor antagonists at the human 5-$HT_{2A}$ receptor and may therefore be used for the treatment of serotonin-related disorders or medical conditions, particularly 5-$HT_{2A}$ receptor-related.

First, the various terms used, separately and in combinations, in the above definition of the compounds having the general formula (I) will be explained.

The expression "$C_{1-6}$ alkyl" refers to straight-chained and branched alkyl groups containing from 1 to 6 carbon atoms. Particular $C_{1-6}$ alkyl groups are methyl, ethyl, n-propyl, isopropyl, tert-butyl, and n-pentyl.

Derived expressions such as "$C_{1-6}$ alkoxy" and "$C_{1-6}$ alkylthio" are to be constructed accordingly. The expression "$C_{1-4}$-alkoxycarbonyl" refers to a $C_1$-$C_4$-alkoxy group directly connected to a carbonyl group. An exemplary $C_{1-4}$-alkoxycarbonyl is tert-butoxycarbonyl (t-BOC).

The expression "$C_{2-6}$ alkenyl" as used herein refers to straight-chained and branched alkenyl groups containing from 2 to 6 carbon atoms. Typical examples include vinyl, allyl (2-propenyl), dimethylallyl and butenyl groups.

The expression "$C_{2-6}$ alkynyl" as used herein refers to straight-chained and branched alkynyl groups containing from 2 to 6 carbon atoms. Typical examples include ethynyl and propargyl groups.

The expression "$C_{2-6}$ alkanoyl" as used herein refers to straight-chained and branched alkanoyl groups containing from 2 to 6 carbon atoms. Typical examples include acetyl, propionyl, n-butanoyl.

The expression "$C_{3-6}$-cycloalkyl" refers to cyclic alkyl groups containing from 3 to 6 carbon atoms. Particular $C_{3-6}$-cycloalkyl groups are cyclopropyl, cyclobutyl, cyclopentyl, and cyclohexyl.

By "heteroatom" is meant nitrogen, oxygen, sulphur, and in heterocyclic rings (including heteroaromatic as well as saturated and partially saturated heterocyclic rings), also selenium.

By "oxo" is meant that a group, especially an aryl or heteroaryl residue (having at least one non-aromatic ring in the residue), substituted by oxo is connected to an exocyclic oxygen atom through a double bond.

By "MPLC" is meant medium pressure liquid chromatography.

The term "base," as used herein, represents a reagent capable of accepting protons during the course of a reaction. Examples of bases include carbonate salts such as potassium carbonate, potassium bicarbonate, sodium carbonate, sodium bicarbonate, and cesium carbonate; halides such as cesium fluoride; phosphates such as potassium phosphate, potassium dihydrogen phosphate, and potassium hydrogen phosphate; hydroxides such as lithium hydroxide, sodium hydroxide, and potassium hydroxide; alkoxides such as sodium tert-butoxide, potassium tert-butoxide, and lithium tert-butoxide; alkylamines such as triethylamine, diisopropylamine, and diisopropylethylamine; heterocyclic amines such as 4-dimethylaminopyridine, 2,6-lutidine, 1-methylimidazole, pyridine; bicyclic amines such as 1,8-diazabicyclo(4.3.0)undec-7-ene; and hydrides such as lithium hydride, sodium hydride, and potassium hydride. The base chosen for a particular conversion depends on the nature of the starting materials, the solvent or solvents in which the reaction is conducted, and the temperature at which the reaction is conducted.

The term "aryl" refers to aromatic rings (e.g., monocyclic or bicyclic) having from 6 to 10 ring carbon atoms, such as phenyl, 1-naphthyl, 2-naphthyl, 1,2,3,4-tetrahydronaphthyl, and indanyl, but only one ring of a multicyclic system need be aromatic. The aryl group can be linked to the remainder of the molecule via a carbon atom in any ring.

The term "heteroaryl" means a mono- or bicyclic aromatic ring system, only one ring need be aromatic, and the said heteroaryl moiety can be linked to the remainder of the molecule via a carbon or nitrogen atom in any ring, and having from 5 to 10 ring atoms (mono- or bicyclic), in which one or more of the ring atoms are other than carbon, such as nitrogen, sulphur, oxygen and selenium. Examples of such heteroaryl rings are pyrrole, imidazole, thiophene, furan, thiazole, isothiazole, thiadiazole, oxazole, isoxazole, oxadiazole, pyridine, pyrazine, pyrimidine, pyridazine, pyrazole, triazole, tetrazole, chroman, isochroman, coumarin, quinoline, quinoxaline, isoquinoline, phthalazine, cinnoline, quinazoline, indole, isoindole, indoline, isoindoline, benzothiophene, benzofuran, 2,3-dihydrobenzofuran, isobenzofuran, benzoxazole, 2H-chromene, benzisoxazol, 1,3-benzooxathiole, 2,1,3-benzoxadiazole, benzothiazole, 2,1,3-benzothiadiazole, 2,1,3-benzoselenadiazole, benzimidazole, indazole, 2,3-dihydro-1,4-benzodioxine, 1,3-benzodioxole, 1,2,3,4-tetrahydroquinoline, 3,4-dihydro-2H-1,4-benzoxazine, 1,5-naphthyridine, 1,8-naphthyridine, 3,4-dihydro-2H-pyrido[3,2-b]-1,4-oxazine, 2,3-dihydro-1,4-benzoxathiine, and 1,2,4-triazolo[1,5-a]pyrimidine. If a bicyclic aryl or heteroaryl ring is substituted, it may be substituted in any ring.

Halogen refers to fluorine, chlorine, bromine or iodine. Fluorine is a preferred halogen when it is part of $R^6$ as substituent.

The term "leaving group" refers to a group which is removed or replaced during a reaction. Examples of leaving groups are halogen, mesylate and tosylate.

Where it is stated above that aryl and heteroaryl residues may be substituted (in one or more positions), this applies to aryl and heteroaryl per se as well as to any combined groups containing aryl or heteroaryl residues, such as heteroaryl-$C_{1-3}$-alkyl and arylcarbonyl, etc.

The term "N-oxides" means that one or more nitrogen atoms, when present in a compound, are in N-oxide form (N→O).

The term "prodrug forms" means a pharmacologically acceptable derivative, such as a carbamate or an amide, which derivative is biotransformed in the body to form the active drug. Reference is made to Goodman and Gilman's, The Pharmacological basis of Therapeutics, $8^{th}$ ed., McGraw-Hill, Int. Ed. 1992, "Biotransformation of Drugs, p. 13-15, and "The Organic Chemistry of Drug Design and Drug Action" by Richard B. Silverman. Chapter 8, p 352 (Academic Press, Inc.

1992. ISBN 0-12-643730-0). "Pharmaceutically acceptable" means being useful in preparing a pharmaceutical composition that is generally safe, non-toxic and neither biologically nor otherwise undesirable and includes being useful for veterinary use as well as human pharmaceutical use.

"Pharmaceutically acceptable salts" mean salts which are pharmaceutically acceptable, as defined above, and which possess the desired pharmacological activity. Such salts include acid addition salts formed with organic and inorganic acids, such as hydrogen chloride, hydrogen bromide, hydrogen iodide, sulfuric acid, phosphoric acid, acetic acid, glycolic acid, maleic acid, malonic acid, malic acid, oxalic acid, toluenesulphonic acid, methanesulphonic acid, fumaric acid, succinic acid, tartaric acid, citric acid, benzoic acid, ascorbic acid, trifluoroacetic acid, isethionic acid (i.e. 2-hydroxyethylsulphonic acid), and the like.

The expression "comprising" means "including but not limited to." Thus, other non-mentioned substances, additives or carriers may be present.

"Extrapyramidal symptoms" are symptoms that may manifest upon administration of neuroleptic drugs. The symptoms include a parkinsonian-like syndrome wherein the patient experiences muscular rigidity and tremors. Some experience akathesia and acute dystonic reactions.

The expressions "N-t-BOC derivative" or "N-t-BOC intermediate" as mentioned in the Exemplary Section, refers to a compound of formula (I) where $R^1$ is t-butoxycarbonyl (t-BOC).

Preferred embodiments of the invention are compounds of formula (I) wherein
  n=1;
  $R^1$, $R^2$, $R^3$, $R^4$ and $R^5$ each are H; and
  $R^6$ is phenoxy, where the phenyl ring of the said phenoxy group may be unsubstituted or substituted. Where substituted, one, two, three, four or five substituents may be present, which may be the same or different, preferably one or two for non-halogen substituents. Examples of preferred substituents on the said $R^6$ phenoxy group are independently selected from halogen, 2-propenyl, $C_1$-$C_6$-alkyl, $C_1$-$C_6$-alkoxy, trifluoromethyl, phenyl, phenoxy, benzoyl, and $C_{3-6}$-cycloalkyl; wherein any of the phenyl, phenoxy or benzoyl in turn may be substituted in one, two or three positions, preferably by halogen. Exemplary phenoxy groups for $R^6$ are 2,4,5-trifluorophenoxy, 3-fluorophenoxy, 4-fluorophenoxy, 2,4-difluorophenoxy, 2,3,4-trifluorophenoxy, 2-fluoro-4-chlorophenoxy, 4-bromophenoxy, and 2,3-dichlorophenoxy.

In another preferred embodiment of the invention is a compound of formula (I) in which
  n=1;
  $R^1$ is methoxy-$C_2$-$C_4$-alkyl or straight-chained $C_1$-$C_4$-alkyl;
  $R^2$, $R^3$, $R^4$ and $R^5$ each are H; and
  $R^6$ is 2,4,5-trifluorophenoxy.

In still another preferred embodiment of the invention is a compound of formula (I) in which
n=1;
$R^1$, $R^2$, $R^3$, $R^4$ and $R^5$ each are H; and
$R^6$ is 2-oxo-1,3-benzoxathiol-5-yloxy.

In yet another preferred embodiment of the invention is a compound of formula (I) in which
n=0;
$R^1$, $R^2$, $R^3$, $R^4$ and $R^5$ each are H; and
$R^6$ is phenyl, where the said phenyl may be substituted with halogen, preferably fluorine, in one, two, three, four or five positions. Even more preferably, $R^6$ represents 2,4,5-trifluorophenyl.

In still another preferred embodiment of the invention is a compound of formula (I) in which
n=1;
$R_1$ is aryl-$C_1$-$C_3$-alkyl (e.g., benzyl and 2-phenylethyl);
$R_2$, $R_3$, $R_4$ and $R_5$ are each H; and
$R^6$ is 2,4,5-trifluorophenoxy.

Preferred compounds of the general formula (I) above are:
1-[2-(2-fluoro-4-nitrophenoxy)ethyl]-3-(1-piperazinyl)-2(1H)-pyrazinone,
1-{2-[(2-oxo-2H-chromen-7-yl)oxy]ethyl}-3-(1-piperazinyl)-2(1H)-pyrazinone,
3-(1-piperazinyl)-1-[2-(2,4,5-trifluorophenoxy)ethyl]-2(1H)-pyrazinone,
3-(1-piperazinyl)-1-[2-(2,3,5,6-tetrafluorophenoxy)ethyl]-2(1H)-pyrazinone,
1-[2-(2,3,4,5,6-pentafluorophenoxy)ethyl]-3-(1-piperazinyl)-2(1H)-pyrazinone,
1-[2-(4-chloro-2-fluorophenoxy)ethyl]-3-(1-piperazinyl)-2(1H)-pyrazinone,
1-[2-(3-cyanophenoxy)ethyl]-3-(1-piperazinyl)-2(1H)-pyrazinone,
1-[2-(4-cyclopentylphenoxy)ethyl]-3-(1-piperazinyl)-2(1H)-pyrazinone,
1-[2-(1,2-benzisoxazol-3-yloxy)ethyl]-3-(1H-piperazinyl)-2(1H)-pyrazinone,
1-[2-(3-methoxyphenoxy)ethyl]-3-(1-piperazinyl)-2(1H)-pyrazinone,
1-[2-(3-n-butyloxyphenoxy)ethyl]-3-(1-piperazinyl)-2(1H)-pyrazinone,
1-[2-([1,1'-biphenyl]-3-yloxy)ethyl]-3-(1-piperazinyl)-2(1H)-pyrazinone,
3-(1-piperazinyl)-1-[2-(2,3,4-trifluorophenoxy)ethyl]-2(1H)-pyrazinone,
1-[2-(2,3-dichlorophenoxy)ethyl]-3-(1-piperazinyl)-2(1H)-pyrazinone,
1-[2-(1,3-benzodioxol-5-yloxy)ethyl]-3-(1-piperazinyl)-2(1H)-pyrazinone,
1-[2-(2,4-difluorophenoxy)ethyl]-3-(1-piperazinyl)-2(1H)-pyrazinone,
1-{2-[(2-oxo-1,3-benzoxathiol-5-yl)oxy]ethyl}-3-(1-piperazinyl)-2(1H)-pyrazinone,
1-[2-(3-hydroxyphenoxy)ethyl]-3-(1-piperazinyl)-2(1H)-pyrazinone,
3-(1-piperazinyl)-1-[2-(6-quinoxalinyloxy)ethyl]-2(1H)-pyrazinone,
1-{2-[3-(N,N-dimethylamino)phenoxy]ethyl}-3-(1-piperazinyl)-pyrazin-2(1H)-one,
3-(1-piperazinyl)-1-{2-[3-(trifluoromethyl)phenoxy]ethyl}-2(1H)-pyrazinone,
1-[2-(3-fluorophenoxy)ethyl]-3-(1-piperazinyl)-2(1H)-pyrazinone,
1-[2-(3-nitrophenoxy)ethyl]-3-(1-piperazinyl)-2(1H)-pyrazinone,
1-[2-(3-benzoylphenoxy)ethyl]-3-(1-piperazinyl)-2(H)-pyrazinone,
1-[2-(3,5-difluorophenoxy)ethyl]-3-(1-piperazinyl)-2(1H)-pyrazinone,
1-[2-(phenoxy)ethyl]-3-(1-piperazinyl)-2(1H)-pyrazinone,
1-[2-(2,6-difluorophenoxy)ethyl]-3-(1-piperazinyl)-2(1H)-pyrazinone,
1-[2-(2-cyanophenoxy)ethyl]-3-(1-piperazinyl)-2(1H)-pyrazinone,
1-[2-(4-trifluoromethylphenoxy)ethyl]-3-(1-piperazinyl)-2(1H)-pyrazinone,
1-[2-(4-bromophenoxy)ethyl]-3-(1-piperazinyl)-2(1H)-pyrazinone,
1-[2-{4-phenoxy-(phenoxy)}ethyl]-3-(1-piperazinyl)-2(1H)-pyrazinone,
1-[2-(4-fluorophenoxy)ethyl]-3-(1-piperazinyl)-2(1H)-pyrazinone,
1-[2-(4-isopropylphenoxy)ethyl]-3-(1-piperazinyl)-2(1H)-pyrazinone,
1-[2-(2,4,5-trichlorophenoxy)ethyl]-3-(1-piperazinyl)-2(1H)-pyrazinone,
1-[2-(2-methylthiophenoxy)ethyl]-3-(1-piperazinyl)-2(1H)-pyrazinone,
1-[2-(3-methoxyphenylthio)ethyl]-3-(1-piperazinyl)-2(1H)-pyrazinone,
1-[2-{(4-allyl-2-methoxy)phenoxy}ethyl]-3-(1-piperazinyl)-2(1H)-pyrazinone,
1-[2-(5,6,7,8-tetrahydro-naphthalen-2-yloxy)ethyl]-3-(1-piperazinyl)-2(1H)-pyrazinone,
1-[2-(2,6-difluorophenoxy)ethyl]-3-(3-methyl-1-piperazinyl)-2(1H)-pyrazinone,
1-[2-(4-trifluoromethylphenoxy)ethyl]-3-(3-methyl-1-piperazinyl)-2(1H)-pyrazinone,
1-[2-(4-bromophenoxy)ethyl]-3-(3-methyl-1-piperazinyl)-2(1H)-pyrazinone,
1-[2-(phenoxy)ethyl]-3-(3-methyl-1-piperazinyl)-2(1H)-pyrazinone,
1-[2-(2,4,5-trifluorophenoxy)ethyl]-3-(3-methyl-1-piperazinyl)-2(1H)-pyrazinone,
1-[2-(2,4,5-trifluorophenoxy)ethyl]-3-(1,4-diazepan-1-yl)-2(1H)-pyrazinone,
1-[2-(4-fluorophenoxy)ethyl]-3-(1,4-diazepan-1-yl)-2(1H)-pyrazinone,
1-[2-(4-isopropylphenoxy)ethyl]-3-(1,4-diazepan-1-yl)-2(1H)-pyrazinone,
1-[2-(2-methylthiophenoxy)ethyl]-3-(1,4-diazepan-1-yl)-2(1H)-pyrazinone,
1-(2,4,5-trifluorobenzyl)-3-(1-piperazinyl)-2(1H)-pyrazinone,
1-[3-(2,4,5-trifluorophenyl)propyl]-3-(1-piperazinyl)-2(1H)-pyrazinone,
1-(2,3-dihydro-benzo[1,4]dioxin-2-ylmethyl)-3-(1-piperazinyl)-2(1H)-pyrazinone,
3-piperazin-1-yl-{[2-(2,4,5-trifluoro-phenoxy)-ethyl]-1H-quinoxalin-2-one,
1-[2-(2,4,5-trifluorophenoxy)ethyl]-3-(4-n-butyl-1-piperazinyl)-2(1H)-pyrazinone,
1-[2-(2,4,5-trifluorophenoxy)ethyl]-3-[4-(2-methoxyethyl)-1-piperazinyl]-2(1H)-pyrazinone,
1-[2-(2,4,5-trifluorophenoxy)ethyl]-3-(4-methyl-1-piperazinyl)-2(1H)-pyrazinone,
1-[2-(2,4,5-trifluorophenoxy)ethyl]-3-(4-isopropyl-1-piperazinyl)-2(1H)-pyrazinone,
1-{2-[(5-methyl[1,2,4]triazolo[1,5-a]pyrimidin-7-yl)oxy]ethyl}-3-(1-piperazinyl)-2(1H)-pyrazinone, 1-[2-(4-Cyanophenoxy)ethyl]-3-(1-piperazinyl)-2(1H)-pyrazinone,
1-[4-(2,4,5-trifluorophenoxy)butyl]-3-(1-piperazinyl)-2(1H)-pyrazinone,
1-[3-(2,4,5-trifluorophenoxy)propyl]-3-(1-piperazinyl)-2(1H)-pyrazinone,
3-[4-(1-phenylethyl)piperazin-1-yl]-1-[2-(2,4,5-trifluorophenoxy)ethyl]-pyrazin-2(1H)-one,
3-[4-(2-phenoxyethyl)piperazin-1-yl]-1-[2-(2,4,5-trifluorophenoxy)ethyl]-pyrazin-2(1H)-one,
3-[4-(2-Phenylethyl)piperazin-1-yl]-1-[2-(2,4,5-trifluorophenoxy)ethyl]pyrazin-2(1H)-one, hydrochloride,
3-(4-Benzylpiperazin-1-yl)-1-[2-(2,4,5-trifluorophenoxy)ethyl]pyrazin-2(1H)-one hydrochloride,
3-[(2R)-2-methylpiperazin-1-yl]-1-[2-(2,4,5-trifluorophenoxy)ethyl]-pyrazin-2(1H)-one,
3-piperazin-1-yl-1-[2-(3-thienyl)ethyl]pyrazin-2(1H)-one,
3-piperazin-1-yl-1-[2-(2-thienyl)ethyl]pyrazin-2(1H)-one,
1-[2-(1H-indol-3-yl)ethyl]-3-piperazin-1-ylpyrazin-2(1H)-one,
1-[2-(2,3-dihydro-1,4-benzodioxin-5-yloxy)ethyl]-3-piperazin-1-ylpyrazin-2(1H)-one,
1-[2-(phenylthio)ethyl]-3-piperazin-1-ylpyrazin-2(1H)-one,
1-(3-oxo-3-phenylpropyl)-3-piperazin-1-ylpyrazin-2(1H)-one, and
1-[3-(4-fluorophenyl)-3-oxopropyl]-3-piperazin-1-ylpyrazin-2(1H)-one, and their pharmacologically acceptable salts and solvates.

As mentioned above, the compounds of the present invention are useful for the treatment, including prophylactic treatment, of serotonin-related, especially 5-HT$_{2A}$ receptor-related, disorders and medical conditions, in a human being or in an animal, including e.g. pets, such as angina; Raynaud's phenomenon; intermittent claudication; coronary or peripheral vasospasms; hypertension; fibromyalgia; thrombotic illness, including stroke; memory disorders, such as Alzheimer's disease; schizophrenia; obsessive-compulsive disorder; mood disorders; autism; attention deficit hyperactivity disorder (ADHD); anxiety disorders; depression disorders, including depression with coexisting diabetes; sexual function disorders; sleep disorders, such as insomnia and sleep apnea; pain; substance abuse; extrapyramidal symptoms (e.g., associated with neuroleptic drug therapy using drugs such as, for example, haloperidol and chlorpromazine); Parkinson's disease; glaucoma including normal tension glaucoma; urinary incontinence including urinary incontinence with co-existing diabetes; menopausal and post-menopausal hot flushes; premenstrual syndrome; bronchoconstriction disorders, such as asthma and chronic obstructive pulmonary disease; eating disorders, such as binge eating disorders, anorexia nervosa and bulimia; diabetic complications such as nephropathy, neuropathy and retinopathy.

The compounds of the present invention in radiolabelled form may be used as a diagnostic agent. Examples of such labels are known in the art and include $^{131}$I, $^{35}$S, $^{32}$P, $^{18}$F, $^{14}$C, $^{11}$C, $^{3}$H, and the like.

Processes for Preparation

This invention also relates to methods of making compounds of any formulae delineated herein comprising reacting any one or more of the compounds or formulae delineated herein including any processes delineated herein.

In one aspect, the invention is a method of making a compound of formula (I) delineated herein. The compounds of general formula (I) above may be prepared by, or in analogy with, conventional methods, and especially according to or in analogy with the following methods:

Compounds of formula (I) are prepared by reacting a compound of the structural formula (II):

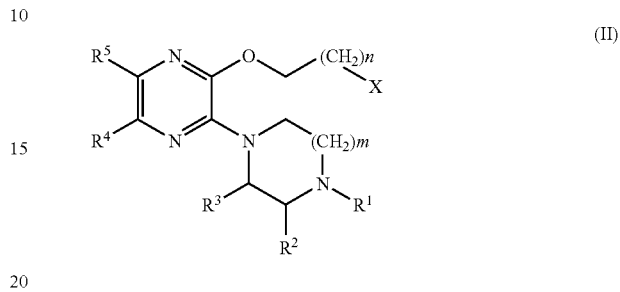

(II)

wherein
m represents 1 or 2;
n represents 1 or 2;
X is OH; and
R$^1$, R$^2$, R$^3$, R$^4$ and R$^5$ are as defined for formula (I); with 1 to 10 molar equivalents of an optionally substituted phenol or thiophenol under Mitsunobu conditions (cf. Org. Reactions 1992, 42, 335-656 and Tetrahedron Lett. 1995, 36, 3789-3792) to produce a compound of formula (I):

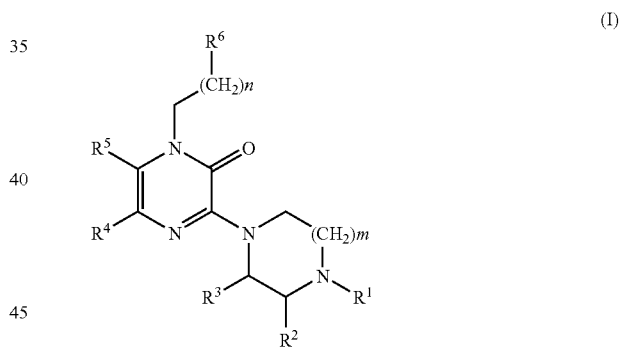

(I)

wherein
m represents 1 or 2;
n represents 1 or 2;
R$^1$, R$^2$, R$^1$, R$^4$, R$^5$ and n are as defined for formula (I);
R$^6$ is selected from aryloxy, heteroaryloxy, arylthio, heteroarylthio, aryl-NH, or heteroaryl-NH, aryl, arylcarbonyl, heteroaryl, or heteroarylcarbonyl; wherein
any aryl or heteroaryl residue, alone or as part of another group, may be unsubstituted or substituted. Where substituted, one, two, three, four or five substituents may be present, preferably one or two for non-halogen substituents, and are independently selected from aryl, aryl-C$_{1-2}$-alkyl, arylcarbonyl, heteroaryl, heteroaryl-C$_{1-2}$-alkyl, heteroarylcarbonyl, aryloxy, heteroaryloxy, arylthio, heteroarylthio, arylamino, heteroarylamino, C$_{3-6}$-cycloalkyl, C$_{3-6}$-cycloalkyloxy, C$_{3-6}$-cycloalkylcarbonyl, C$_{1-6}$-alkyl, C$_{2-6}$-alkanoyl, C$_{2-6}$-alkynyl, C$_{2-6}$- alkenyl, or fluoro-$C_{2-4}$-alkyloxy, halogen, trifluoromethyl, nitro, cyano, trifluoromethoxy, trifluoromethylthio, $C_{1-6}$-alkoxy, $C_{1-6}$-alkylthio, $C_{1-6}$-alkylamino, $C_{1-4}$-dialkylamino, hydroxy or oxo; wherein any aryl or heteroaryl residue as substituents on aryl or heteroaryl, alone or as part of another group, in turn may be substituted in one or more positions, preferably one, independently of each other by $C_{1-4}$-alkyl, $C_{1-4}$-alkoxy, $C_{1-4}$-alkylthio, halogen, trifluoromethyl, trifluoromethoxy, or cyano.

Typically, the said Mitsunobu reaction is carried out in the presence of diethyl azodicarboxylate (DEAD) or 1,1'-azobis(N,N-dimethylformamide (TMAD), preferably TMAD, and triphenylphosphine or tri-n-butylphosphine, preferably triphenylphosphine, in a solvent such as N,N-dimethylformamide (DMF), dichloromethane or tetrahydrofuran (THF), especially DMF, or in a suitable mixture of solvents, such as THF:DMF, at −25 to 50° C., typically at room temperature, for 1-48 hours.

For compounds of formula (I) where $R^1$ is H, $R^1$ in the corresponding intermediate of formula (II) is a suitable protecting group, preferably tert-butoxycarbonyl (t-BOC) or trityl.

The intermediates of formula (II) may be prepared according to the methodology described in WO 00/76984 and as described in Examples 73-75.

The method described above for producing a compound of formula (I) from a compound of formula (II) may produce a mixture of structural isomers containing the desired compound of formula (I) according to the current invention and the corresponding structural isomer of formula (Ib) disclosed in WO 00/76984. The ratio of the two structural isomers may vary depending on the experimental conditions used. These compounds may be conveniently separated by conventional techniques including chromatography, such as column chromatography on silica gel or preparative HPLC. The identity of the individual structural isomers may be established by spectroscopic techniques such as nuclear magnetic resonance (NMR) spectroscopy, including proton and carbon NMR ($^1$H NMR and $^{13}$C NMR) spectroscopy, and infrared spectroscopy (1R).

Alternatively, the compounds of formula (I) can also be prepared by reacting a compound of formula (IV),

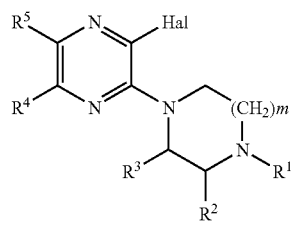

(IV)

wherein
m is 1 or 2;
Hal is halogen, typically chlorine; and
$R^1$, $R^2$, $R^3$, $R^4$, and $R^5$ are as defined for formula (I); with an alkali metal or alkaline earth metal basic salt, eg., a hydroxide or carbonate such as NaOH or $K_2CO_3$, in aqueous media, such as water:dimethyl sulfoxide (DMSO), at 25 to 150° C., to produce a compound of formula (V),

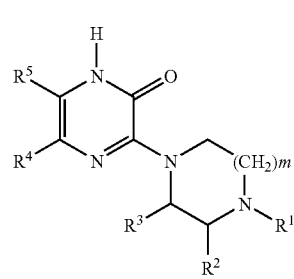

(V)

wherein m, $R^1$, $R^2$, $R^3$, $R^4$, and $R^5$ are as defined for formula (I), followed by N-alkylation of the compound of formula (V) by reaction with a compound of formula (VI),

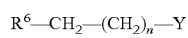

$R^6$—$CH_2$—$(CH_2)_n$—Y (VI)

wherein
n is 0, 1, 2, 3 or 4;
Y is a suitable leaving group such as mesylate, tosylate, chlorine, bromine or iodine; and
$R^6$ represents aryloxy, heteroaryloxy, arylthio, heteroarylthio, aryl-NH, heteroaryl-NH, aryl, arylcarbonyl, heteroaryl, or heteroarylcarbonyl; wherein any aryl or heteroaryl residue, alone or as part of another group, may be unsubstituted or substituted. Where substituted, one, two, three, four or five substituents may be present, preferably one or two for non-halogen substituents, and are independently selected from aryl, aryl-$C_{1-2}$-alkyl, arylcarbonyl, heteroaryl, heteroaryl-$C_{1-2}$-alkyl, heteroaylcarbonyl, aryloxy, heteroaryloxy, arylthio, heteroarylthio, arylamino, heteroarylamino, $C_{3-6}$-cycloalkyl, $C_{3-6}$-cycloalkyloxy, $C_{3-6}$-cycloalkylcarbonyl, $C_{1-6}$-alkyl, $C_{2-6}$-alkanoyl, $C_{2-6}$-alkynyl, $C_{2-6}$-alkenyl, or fluoro-$C_{2-4}$-alkyloxy, halogen, trifluoromethyl, nitro, cyano, trifluoromethoxy, trifluoromethylthio, $C_{1-6}$-alkoxy, $C_{1-6}$-alkylthio, $C_{1-6}$-alkylamino, $C_{1-4}$-dialkylamino, hydroxy or oxo; wherein any aryl or heteroaryl residue as substituents on aryl or heteroaryl, alone or as part of another group, in turn may be substituted in one or more postions, preferably one, independently of each other by $C_{1-4}$-alkyl, $C_{1-4}$-alkoxy, $C_{1-4}$-alkylthio, halogen, trifluoromethyl, trifluoromethoxy, or cyano;

typically in the presence of a base such as an alkali metal hydride, such as sodium hydride, or sodium or potassium tert-butoxide (t-BuONa or t-BuOK), or potassium carbonate or caesium carbonate or the like in a suitable solvent such as THF, dioxane, diglyme, 1,2-dimethoxyethane, DMF, DMSO, or acetonitrile, suitably at an elevated temperature, typically the reflux temperature of the solvent employed. The said N-alkylation reaction may be carried out in the presence of sodium iodide or potassium iodide in cases where Y in formula (VI) is other than iodine.

For compounds of formula (I) where $R^1$ is H, $R^1$ in the intermediate of formula (V) is a suitable protecting group, preferably tert-butoxycarbonyl (t-BOC) or trityl, particularly t-BOC.

The intermediates of formula (IV) may be prepared according to the methodology described in WO 00/76984 and as described in Example 54, Step 1, and Example 55, Step 1.

When $R^1$ is a nitrogen protecting group, such as tert-butoxycarbonyl (t-BOC) or trityl, the subsequent N-deprotection is carried out by conventional methods such as those described in Protective Groups in Organic Synthesis, John Wiley & Sons, 1991.

An obtained compound of formula (I) above may be converted to another compound of formula (I) by methods well known in the art. Different groups may be introduced, such as $C_{1-6}$-alkyl groups, aryl-$C_1$-$C_3$-alkyl or methoxy-$C_2$-$C_4$-alkyl groups for $R^1$ in the formula (I). The conditions may be those described in Example 52, Step 2; Example 53, Step 2; and Examples 60-63.

The chemicals used in the above-described synthetic routes may include, for example, solvents, reagents, catalysts, protecting group and deprotecting group agents. The methods described above may also additionally include steps, either before or after the steps described specifically herein, to add or remove suitable protecting groups in order to ultimately allow synthesis of the compounds of any of the formulae described above, their salt forms, or compositions that include the compounds or their salt forms. In addition, various synthetic steps may be performed in an alternate sequence or order to give the desired compounds. Synthetic chemistry transformations and protecting group methodologies (protection and deprotection) useful in synthesizing applicable compounds of the formula (I) are known in the art and include, for example, those described in R. Larock, *Comprehensive Organic Transformations*, VCH Publishers (1989); T. W. Greene and P. G. M. Wuts, *Protective Groups in Organic Synthesis*, $3^{rd}$ Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

The process that is described above may be carried out to give a compound of the invention in the form of a free base or as an acid addition salt. A pharmaceutically acceptable acid addition salt may be obtained by dissolving the free base in a suitable organic solvent and treating the solution with an acid, in accordance with conventional procedures for preparing acid addition salts from base compounds. Examples of addition salt forming acids are hydrogen chloride, hydrogen bromide, hydrogen iodide, sulfuric acid, phosphoric acid, acetic acid, glycolic acid, maleic acid, malonic acid, malic acid, oxalic acid, toluenesulphonic acid, methanesulphonic acid, fumaric acid, succinic acid, tartaric acid, citric acid, benzoic acid, ascorbic acid, trifluoroacetic acid, isethionic acid (i.e. 2-hydroxyethylsulphonic acid), and the like.

The compounds of formula (I) may possess one or more chiral carbon atoms, and they may therefore be obtained in the form of optical isomers, e.g. as a pure enantiomer, or as a mixture of enantiomers (racemate) or as a mixture containing diastereomers. The separation of mixtures of optical isomers to obtain pure enantiomers is well known in the art and may, for example, be achieved by fractional crystallization of salts with optically active (chiral) acids or by chromatographic separation on chiral columns.

The necessary starting materials for preparing the compounds of formula (I) are either known or may be prepared in analogy with the preparation of known compounds.

In accordance with the present invention, the compounds of formula (I), in the form of free bases or salts with physiologically acceptable acids, can be brought into suitable galenic forms, such as compositions for oral use, for injection, for nasal spray administration or the like, in accordance with accepted pharmaceutical procedures. Such pharmaceutical compositions according to the invention comprise an effective amount of the compounds of formula (I) in association with compatible pharmaceutically acceptable carrier materials, or diluents, as are well known in the art. The carriers may be any inert material, organic or inorganic, suitable for enteral, percutaneous, subcutaneous or parenteral administration, such as: water, gelatin, gum arabicum, lactose, microcrystalline cellulose, starch, sodium starch glycolate, calcium hydrogen phosphate, magnesium stearate, talcum, colloidal silicon dioxide, and the like. Such compositions may also contain other pharmacologically active agents, and conventional additives, such as stabilizers, wetting agents, emulsifiers, flavoring agents, buffers, and the like.

The compositions according to the invention can e.g. be made up in solid or liquid form for oral administration, such as tablets, pills, capsules, powders, syrups, elixirs, dispersable granules, cachets, suppositories and the like, in the form of sterile solutions, suspensions or emulsions for parenteral administration, sprays, e.g. a nasal spray, transdermal preparations, e.g. patches, and the like.

As mentioned above, the compounds of the invention may be used for the treatment of serotonin-related, especially 5-$HT_{2A}$ receptor-related, disorders and medical conditions in a human being or an animal, such as angina, Raynaud's phenomenon, intermittent claudication, coronary or peripheral vasospasms, hypertension, fibromyalgia, thrombotic illness (including stroke), memory disorders, such as Alzheimer's disease; schizophrenia; obsessive-compulsive disorder; mood disorders; autism; attention deficit hyperactivity disorder (ADHD); anxiety disorders; depression disorders (including depression with coexisting diabetes), sexual function disorders, sleep disorders, such as insomnia and sleep apnea, pain; substance abuse; extrapyramidal symptoms (e.g., associated with neuroleptic drug therapy using drugs such as, for example, haloperidol and chlorpromazine); Parkinson's disease; glaucoma including normal tension glaucoma; urinary incontinence including urinary incontinence with co-existing diabetes; menopausal and post-menopausal hot flushes; premenstrual syndrome; bronchoconstriction disorders, such as asthma and chronic obstructive pulmonary disease; eating disorders, such as binge eating disorders, anorexia nervosa and bulimia; diabetic complications such as nephropathy, neuropathy and retinopathy.

This invention relates to a method of treatment or prophylaxis of a 5-$HT_{2A}$-receptor-related disorder or medical condition. The method includes administering to a subject (e.g., a mammal, a human, a horse, a dog, or a cat) in need thereof an effective amount of one or more compounds of any of the formulae described above, their salt forms, or compositions that include the compounds or their salt forms.

Also within the scope of this invention is a method for modulating (e.g., inhibiting) 5-$HT_{2A}$ receptor activity. The above-mentioned disorders and medical conditions may be treated with a 5-$HT_{2A}$ antagonist. The method includes administering to a subject in need thereof an effective amount of one or more compounds of any of the formulae described above, their salt forms, or compositions that include the compounds or their salt forms.

The methods delineated herein can also include the step of identifying that the subject is in need of treatment of aforementioned disorders or medical conditions. The identification can be in the judgment of a subject or a health care professional and can be a subjective (e.g., opinion) or objective (e.g., measurable by a test or diagnostic method).

"An effective amount" refers to an amount of a compound that confers a therapeutic effect on the treated subject. The therapeutic effect may be objective (i.e., measurable by some test or marker) or subjective (i.e., subject gives an indication of or feels an effect). For clinical use, the compounds of the invention are formulated into pharmaceutical formulations for oral, rectal, parenteral, topical or other mode of administration. Usually the amount of active compounds is between 0.1-95% by weight of the preparation, preferably between 0.2-20% by weight in preparations for parenteral use and preferably between 1 and 50% by weight in preparations for oral administration.

The typical dose of the active substance varies within a wide range and will depend on various factors such as, for example, the individual requirement of each patient and the route of administration. In general, oral and parenteral dosages will be in the range of 5 to 1000 mg per day of active substance, preferably 50 to 150 mg per day.

The dose level, frequency of dosage, mode of administration, of the specific compound will vary depending on a variety of factors including the potency of the specific compound employed, the metabolic stability and length of action of that compound, the patient's age, body weight, general health, sex, diet, mode and time of administration, rate of excretion, drug combination, the severity of the condition to be treated, and the patient undergoing therapy.

All references cited herein, whether in print, electronic, computer readable storage media or other form, are expressly incorporated by reference in their entirety, including but not limited to, abstracts, articles, journals, publications, texts, treatises, internet web sites, databases, patents, and patent publications.

The invention will now be illustrated with the following examples, which however, are for illustrative purposes are not intended to limit the scope of the invention.

EXAMPLES

General. NMR spectra were recorded on a Bruker DPX 400, Bruker DRX 500, Jeol 270 or on a Varian Unity Inova 400 spectrometer. Column chromatography was performed on Silica gel 60 (230-400 mesh, E. Merck). The preparative HPLC purifications were performed on a YMC OPS-AQ CombiPrep column (50×20 mm, i.d., 5 µm particle size, 120 Å), using various gradients of acetonitrile-water containing 0.1% TFA as eluent at a flow rate of 30 mL/min, using a LC/MS Gilson-Finnigan instrument equipped with Gilson pumps, a Dynamax UV-1 detector and a Finnigan Mass detector. Analytical reversed-phase HPLC analyses were carried out on a ACE C8 column (50×4.6 mm) using various gradients of acetonitrile-water, containing 0.005 M ammonium acetate, at a flow rate of 1 mL/min, using a Waters ZQ LC-MS setup. "Speed-vac" refers to a Speed-vac Plus SC250DDA or a Gene-vac DD-4. The accurate mass analyses were determined on a Micromass LCT instrument using electrospray ionisation. The elemental analyses were performed by MikroKemi AB, Uppsala, Sweden or on an Elementar Vario EL instrument at Biovitrum AB, Stockholm, Sweden, and reported results were within ±0.4% of the theoretical values. Melting points, when given, were obtained on a Büchi Meltingpoint B-545, Electrothermal IA 9000, or a Gallenkamp MPD350 apparatus and are uncorrected. The intermediate 2-[3-(4-tert-butoxycarbonyl-1-piperazinyl)-pyrazinyloxy]ethanol was prepared as described in WO 00/76984, Example 52, Step 2.

Example 1

1-[2-(2-Fluoro-4-nitrophenoxy)ethyl]-3-(1-piperazinyl)-2(1H)-pyrazinone, Hydrochloride 2-Fluoro-4-nitrophenol (732 mg, 4.66 mmol), 2-[3-(4-tert-butoxycarbonyl-1-piperazinyl)-pyrazinyloxy]ethanol (1.375 g, 4.240 mmol) and triphenylphosphine (1.22 g, 4.66 mmol) were dissolved in THF (8 mL) and 1,1'-azobis(N,N-dimethylformamide (TMAD; 802 mg, 4.66 mmol) was added in three portions. The reaction mixture was stirred at room temperature overnight and then centrifugated. The supernatant was concentrated in vacuo. The residue was dissolved in EtOAc and washed with 5% $NaHCO_3$ and brine. The organic layer was concentrated in vacuo and the residue purified by flash-chromatography using EtOAc/toluene (4:6) as eluent to give 451 mg (23%) of the title compound as its N-t-BOC derivative. The N-t-BOC intermediate (440 mg, 0.949 mmol) was treated with trifluoroacetic acid (TFA)/dichloromethane/$H_2O$ (36:60:4, 3.6 mL) for 45 min. The solution was concentrated in vacuo and the residue precipitated with ether. This material was dissolved in 50% aqueous MeOH (15 mL) and passed through an anion exchange resin (Dowex-1 X8, $Cl^-$, 4 g) eluting with 50% aqueous MeOH. Evaporation of the solvent in vacuum gave the title compound. Yield: 364 mg (96%); mp 105-108° C.; MS-EI m/z 363 $(M)^+$. Anal. ($C_{16}H_{18}N_5O_4F.1.1$ HCl.0.2 $H_2O$)C, H, N.

Example 2

1-{2-[(2-Oxo-2H-chromen-7-yl)oxy]ethyl}-3-(1-piperazinyl)-2(1H)-pyrazinone, Hydrochloride Diethyl azodicarboxylate (DEAD; 0.63 mL, 4.0 mmol) was added over 20 min to a stirred mixture of 7-hydroxycoumarin (713 mg, 4.40 mmol), 2-[3-(4-tert-butoxycarbonyl-1-piperazinyl)-pyrazinyloxy]ethanol (1.29 g, 4.00 mmol) and triphenylphosphine (1.05 g, 4.00 mmol) in THF (15 mL). The reaction mixture was stirred at room temperature overnight. Removal of solvent in vacuum and purification of the residue by repeated chromatography on silica gel using EtOAc/toluene and dichloromethane/MeOH (96:4) as eluents, respectively, gave 871 mg (46%) of the title compound as its N-t-BOC derivative. The N-t-BOC intermediate (800 mg, 1.71 mmol) was treated with TFA/dichloromethane/$H_2O$ (40:55:5; 4.2 mL) for 70 min. The solution was evaporated and the residue precipitated with ether. This material (843 mg) was dissolved in 50% aqueous MeOH (10 mL) and passed through an anion exchange resin (Dowex-1 X8, $Cl^-$, 5 g) eluting with 50% aqueous MeOH. The resulting hydrochloride salt of the title compound was further purified by chromatography on LiChroprep RP-18 (Merck) reversed phase silica gel (5×2.5 cm) eluting with 25% acetonitrile in 0.02 M HCl. The product-containing fractions were pooled, concentrated in vacuo and freeze-dried to furnish 600 mg (85%) of the title compound. MS-EI m/z 368 $(M)^+$. Anal. ($C_{19}H_{20}N_4O_4.HCl.0.7$ $H_2O$)C, H, N.

Example 3

3-(1-Piperazinyl)-1-[2-(2,4,5-trifluorophenoxy)ethyl]-2(1H)-pyrazinone, Hydrochloride 2,4,5-Trifluorophenol (533 mg, 3.60 mmol), 2-[3-(4-tert-butoxycarbonyl-1-piperazinyl)-pyrazinyloxy]ethanol (972 mg, 3.00 mmol), TMAD (619 mg, 3.60 mmol) and polymer-bound triphenylphosphine (Fluka) (1.2 g, 3.6 mmol) were shaken in dichloromethane (10 mL) under nitrogen for about 21 h. The polymer was filtered off and washed with dichloromethane. The solvent was evaporated and the residue was dissolved in CHCl$_3$ and washed with 1 M Na$_2$CO$_3$ and brine. Removal of solvent in vacuo and purification of the residue by column chromatography on silica gel using CHCl$_3$→CHCl$_3$/MeOH (98:2) as eluent gave 791 mg (58%) of the title compound as its N-t-BOC derivative. The N-t-BOC intermediate (700 mg, 1.54 mmol) was treated with TFA/dichloromethane/H$_2$O (42:53:5; 4 mL) and kept at room temperature for 50 min with stirring. The solution was concentrated and the residue precipitated with MeOH/ether. This material was dissolved in 50% aqueous MeOH and passed through an anion exchange resin (Dowex-1 X8, Cl$^-$, 4 g) eluting with 50% aqueous MeOH. Evaporation of the solvent in vacuum gave the title compound. Yield: 513 mg (85%); mp 193-195° C.; MS-EI m/z 354 (M)$^+$; HRMS m/z calcd for C$_{16}$H$_{17}$F$_3$N$_4$O$_2$ (M)$^+$ 354.1304, found 354.1301. Anal. (C$_{16}$H$_{17}$F$_3$N$_4$O$_2$.HCl) C, H, N.

This compound, isolated as its acetate salt, has also been prepared according to the procedure of Example 65 by replacing 2-(4-allyl-2-methoxy-phenoxy)-ethyl methanesulfonate with 2-(2,4,5-trifluorophenoxy)ethyl methanesulfonate.

Example 4

3-(1-Piperazinyl)-1-[2-(2,3,5,6-tetrafluorophenoxy)ethyl]-2(1H)-pyrazinone, Hydrochloride 2,3,5,6-Tetrafluorophenol (556 mg, 3.35 mmol), 2-[3-(4-tert-butoxycarbonyl-1-piperazinyl)-pyrazinyloxy]ethanol (1.01 g, 3.10 mmol) and triphenylphosphine (813 mg, 3.10 mmol) were dissolved in THF (10 mL) and TMAD (533 mg, 3.10 mmol) was added in three portions over 50 min. The reaction mixture was stirred at room temperature overnight. A small amount of a white precipitate was filtered off. The filtrate was evaporated, redissolved in ether and filtered again. The filtrate was washed with 5% NaHCO$_3$ and brine, concentrated in vacuo, and the residue purified by flash chromatography using EtOAc/toluene (3:7 followed by 1:4) as eluent. This gave 584 mg (40%) of the title compound as its N-t-BOC derivative. The N-t-BOC intermediate (568 mg, 1.20 mmol) was treated with TFA/dichloromethane/H$_2$O (42:53:5; 3.1 mL) at room temperature for 50 min with stirring. The solution was evaporated and the residue precipitated with MeOH-ether. This product was dissolved in 50% aqueous MeOH and passed through an anion exchange resin (Dowex-1 X8, Cl$^-$, 4 g) eluting with 50% aqueous MeOH. Evaporation of the solvent in vacuum gave the title compound. Yield: 453 mg (92%); mp 196-198° C. (dec.); MS-EI m/z 372 (M)$^+$; HRMS m/z calcd for C$_{16}$H$_{16}$F$_4$N$_4$O$_2$ (M)$^+$ 372.1209, found 372.1196. Anal. (C$_{16}$H$_{16}$F$_4$N$_4$O$_2$.HCl) C, H, N.

Example 5

1-[2-(2,3,4,5,6-Pentafluorophenoxy)ethyl]-3-(1-piperazinyl)-2(1H)-pyrazinone, Hydrochloride Pentafluorophenol (608 mg, 3.30 mmol), 2-[3-(4-tert-butoxycarbonyl-1-piperazinyl)-pyrazinyloxy]ethanol (1.01 g, 3.10 mmol) and triphenylphosphine (813 mg, 3.10 mmol) were dissolved in THF (5 mL) and TMAD (533 mg, 3.1 mmol) was added in three portions. The reaction mixture was stirred at room temperature overnight. A small amount of a white precipitate was filtered off. The filtrate was concentrated in vacuo and the residue was dissolved in ether, washed with 5% NaHCO$_3$ and brine. Removal of solvent in vacuo and purification of the residue by flash chromatography using toluene/EtOAc (3:7 followed by 1:4) as eluent gave 332 mg (22%) of the title compound as its N-t-BOC derivative. This material (0.677 mmol) was treated with TFA/dichloromethane/H$_2$O (42:53:5; 1.74 mL) for 1 h. The solution was evaporated and the residue precipitated with MeOH/ether. This product was dissolved in 50% aqueous MeOH and passed through an anion exchange resin (Dowex-1 X8, Cl$^-$, 4 g) eluting with 50% aqueous MeOH. Evaporation of the solvent in vacuum gave the title compound. Yield: 275 mg (92%). MS-EI m/z 390 (M)$^+$. HRMS m/z calcd for C$_{16}$H$_{15}$F$_5$N$_4$O$_2$ (M)$^+$ 390.1115, found 390.1106. Anal. (C$_{16}$H$_{15}$F$_5$N$_4$O$_2$.HCl) C, H, N.

Example 6

1-[2-(4-Chloro-2-fluorophenoxy)ethyl]-3-(1-piperazinyl)-2(1H)-pyrazinone 1,1'-Azobis(N,N-dimethylformamide (TMAD; 0.217 g, 1.26 mmol) was added to a stirred mixture of 2-[3-(4-tert-butoxycarbonyl-1-piperazinyl)-pyrazinyloxy]ethanol (0.324 g, 1.00 mmol), triphenylphosphine (0.324 g, 1.23 mmol) and 4-chloro-fluorophenol (0.217 g, 1.48 mmol) in THF (1 mL) at room temperature. After 2 h, the reaction mixture was concentrated and the crude N-t-BOC derivative of the title compound was N-deprotected with TFA/dichloromethane/H$_2$O (45:50:5). Purification by chromatography on silica gel using EtOAc/toluene (4:6) as eluent gave 0.123 g (35%) of the title compound as a yellow oil. HRMS m/z calcd for C$_{16}$H$_{18}$ClFN$_4$O$_2$ (M)$^+$ 352.1102, found 352.1098.

Example 7

1-[2-(3-Cyanophenoxy)ethyl]-3-(1-piperazinyl)-2(1H)-pyrazinone

The title compound was prepared according to the procedure described in Example 6 starting from 3-cyanophenol (0.149 g, 1.25 mmol). This gave 115 mg (35%) of the title compound as a yellow solid: mp 49-52° C. HRMS m/z calcd for C$_{17}$H$_{19}$N$_5$O$_2$ (M)$^+$ 325.1539, found 325.1549.

Example 8

1-[2-(4-Cyclopentylphenoxy)ethyl]-3-(1-piperazinyl)-2(1H)-pyrazinone

The title compound was prepared according to the procedure described in Example 6 starting from 4-cyclopentylphenol (0.203 g, 1.25 mmol). This gave 30 mg (8%) of the title compound as a yellow oil. HRMS m/z calcd for C$_{21}$H$_{28}$N$_4$O$_2$ (M)$^+$ 368.2212, found 368.2193

Example 9

1-[2-(1,2-Benzisoxazol-3-yloxy)ethyl]-3-(1-piperazinyl)-2(1H)-pyrazinone, Dihydrochloride The title substance was prepared by dissolving 3-hydroxybenzisoxazole (0.324 g, 1.0 mmol), tri-n-butylphosphine (PBu$_3$; 0.360 mL, 1.46 mmol), 2-[3-(4-tert-butoxycarbonyl-1-piperazinyl)-pyrazinyloxy]ethanol (0.324 g, 1.00 mmol) in DMF (1 mL) and adding 1,1'-azobis(N,N-dimethylformamide (TMAD; 0.215 g, 1.25 mmol). The reaction was heated in a Labwell microwave reactor for 1 min at 75 W. The N-t-BOC derivative of the title compound was purified by chromatography on silica gel using MeOH/CHCl$_3$ (5:95) as eluent. The subsequent N-deprotection was carried out using TFA/dichloromethane/H$_2$O (45:50:5). The title product was isolated as a yellow solid. Yield: 0.085 g (20%); mp 174-176° C. HRMS m/z calcd for C$_{17}$H$_{19}$N$_5$O$_3$ (M)$^+$ 341.1488, found 341.1496.

Example 10

1-[2-(3-Methoxyphenoxy)ethyl]-3-(1-piperazinyl)-2 (1H)-pyrazinone

TMAD (0.060 g, 0.35 mmol) was dissolved in THF (1 mL) and DMF (0.5 mL) and the solution added dropwise to a mixture of 2-[3-(4-tert-butoxycarbonyl-1-piperazinyl)-pyrazinyloxy]ethanol (0.100 g, 0.310 mmol), triphenylphosphine (0.092 g, 0.35 mmol) and 3-methoxyphenol (0.124 g, 1.00 mmol) in THF (0.5 mL). The reaction mixture was stirred overnight at room temperature, concentrated, and put through a silica column using toluene/EtOAc (7:3) as eluent. Solvents were removed in vacuo and the N-t-BOC derivative of the title compound was treated with dichloromethane/TFA/H$_2$O (50:45:5; 5 mL) for 15 min. The mixture was concentrated and the residue was purified by chromatography on silica gel using EtOAc/HOAc/MeOH/H$_2$O (20:3:3:2) as eluent. The product-containing fractions were concentrated, washed between dichloromethane/5% aqueous NaOH, and put through a silica column using dichloromethane/MeOH (8:2) as eluent to give 40 mg (34%) of the title compound as an oil. HRMS m/z calcd for C$_{17}$H$_{22}$N$_4$O$_3$ (M)$^+$ 330.1692, found 330.1677.

Example 11

1-[2-(3-n-Butyloxyphenoxy)ethyl]-3-(1-piperazinyl)-2(1H)-pyrazinone

TMAD (0.060 g, 0.35 mmol) was dissolved in THF (1 mL) and DMF (0.5 mL) and the solution was added dropwise to a mixture of 2-[3-(4-tert-butoxycarbonyl-1-piperazinyl)-pyrazinyloxy]ethanol (0.100 g, 0.310 mmol), triphenylphosphine (0.092 g, 0.35 mmol) and 3-n-butyloxyphenol (0.166 g, 1.00 mmol) in THF (0.5 mL). The reaction mixture was stirred overnight at room temperature, concentrated, and put through a silica column using toluene/EtOAc (7:3) as eluent. Solvents were removed in vacuo and the resulting N-t-BOC derivative was treated with dichloromethane/TFA/H$_2$O (50:45:5; 5 mL) for 15 min with stirring. The mixture was concentrated and the residue purified by chromatography on silica gel using EtOAc/HOAc/MeOH/H$_2$O (20:3:3:2) as eluent. The product-containing fractions were concentrated, washed between dichloromethane/5% aqueous NaOH, and put through a silica column using dichloromethane/MeOH (8:2) as eluent to give 97 mg (7%) of the title compound. HRMS m/z calcd for C$_{20}$H$_{28}$N$_4$O$_3$ (M)$^+$ 372.2161, found 372.2149.

Example 12

1-[2-([1,1'-Biphenyl]-3-yloxy)ethyl]-3-(1-piperazinyl)-2(1H)-pyrazinone

TMAD (0.060 g, 0.35 mmol) was dissolved in THF (1 mL) and DMF (0.5 mL) and the resulting solution was added dropwise to a mixture of 2-[3-(4-tert-butoxycarbonyl-1-piperazinyl)-pyrazinyloxy]ethanol (0.100 g, 0.31 mmol), triphenylphosphine (0.092 g, 0.35 mmol) and 3-phenylphenol (0.170 g, 1.00 mmol) in THF (0.5 mL). The reaction mixture was stirred overnight at room temperature, concentrated, and put through a silica column using toluene/EtOAc (7:3) as eluent. Solvents were removed in vacuo and the resulting N-t-BOC derivative was treated with dichloromethane/TFA/H$_2$O (50:45:5; 5 mL) for 15 min with stirring. The mixture was concentrated and the residue purified by chromatography on silica gel using EtOAc/HOAc/MeOH/H$_2$O (20:3:3:2) as eluent. The product-containing fractions were concentrated, washed between dichloromethane/5% aqueous NaOH, and put through a silica column using dichloromethane/MeOH (8:2) as eluent to give 16 mg (16%) of the title compound. HRMS m/z calcd for C$_{22}$H$_{24}$N$_4$O$_2$ (M)$^+$ 376.1899, found 376.1888.

Example 13

3-(1-Piperazinyl)-1-[2-(2,3,4-trifluorophenoxy) ethyl]-2(1H)-pyrazinone

TMAD (0.207 g, 1.20 mmol) was added to a solution of 2-[3-(4-tert-butoxycarbonyl-1-piperazinyl)-pyrazinyloxy] ethanol (0.324 g, 1.00 mmol), triphenylphosphine (0.315 g, 1.20 mmol) and 2,3,4-trifluorophenol (0.296 g, 2.00 mmol) in THF (1 mL) at room temperature. After being stirred for 2 h, the mixture was concentrated in vacuo and put through a silica column using toluene/EtOAc (7:3) as eluent. Solvents were removed in vacuo and the resulting N-t-BOC derivative was treated with dichloromethane/TFA/H$_2$O (50:45:5; 5 mL) for 15 min with stirring. The mixture was concentrated and the residue purified by chromatography on silica gel using EtOAc/HOAc/MeOH/H$_2$O (20:3:3:2) as eluent. The product-containing fractions were concentrated, washed between dichloromethane/5% aqueous NaOH, and put through a silica column using dichloromethane/MeOH (8:2) as eluent to give 62 mg (17%) of the title compound. HRMS m/z calcd for C$_{16}$H$_{17}$F$_3$N$_4$O$_2$ (M)$^+$ 354.1304, found 354.1321.

Example 14

1-[2-(2,3-Dichlorophenoxy)ethyl]-3-(1-piperazinyl)-2(1H)-pyrazinone

TMAD (0.207 g, 1.20 mmol) was added to a solution of 2-[3-(4-tert-butoxycarbonyl-1-piperazinyl)-pyrazinyloxy] ethanol (0.324 g, 1.00 mmol), triphenylphosphine (0.315 g, 1.20 mmol) and 2,3-dichlorophenol (0.326 g, 2.00 mmol) in THF (1 mL) at room temperature. After being stirred for 2 h, the mixture was concentrated in vacuo and put through a silica column using toluene/EtOAc (7:3) as eluent. Solvents were removed in vacuo and the resulting N-t-BOC derivative was treated with dichloromethane/TFA/H$_2$O (50:45:5; 5 mL) for 15 min with stirring. The mixture was concentrated and the residue purified by chromatography on silica gel using EtOAc/HOAc/MeOH/H$_2$O (20:3:3:2) as eluent. The product-containing fractions were concentrated, washed between dichloromethane/5% aqueous NaOH, and put through a silica column using dichloromethane/MeOH (8:2) as eluent to give 60 mg (16%) of the title compound. HRMS m/z calcd for C$_{16}$H$_{18}$Cl$_2$N$_4$O$_2$ (M)$^+$ 368.0807, found 368.0818.

Example 15

1-[2-(1,3-Benzodioxol-5-yloxy)ethyl]-3-(1-piperazinyl)-2(1H)-pyrazinone

TMAD (0.207 g, 1.20 mmol) was added to a solution of 2-[3-(4-tert-butoxycarbonyl-1-piperazinyl)-pyrazinyloxy]

ethanol (0.324 g, 1.00 mmol), triphenylphosphine (0.315 g, 1.20 mmol) and sesamol (0.173 g, 1.25 mmol) in THF (1 mL) at room temperature. After being stirred for 2 h, the reaction mixture was concentrated and put through a silica column using toluene/EtOAc (7:3) as eluent. Solvents were removed in vacuo and the resulting N-t-BOC derivative was treated with dichloromethane/TFA/H$_2$O (50:45:5; 5 mL) for 15 min with stirring. The mixture was concentrated and the residue purified by chromatography on silica gel using EtOAc/HOAc/MeOH/H$_2$O (20:3:3:2) as eluent. The product-containing fractions were concentrated, washed between dichloromethane/5% aqueous NaOH, and put through a silica column using dichloromethane/MeOH (8:2) to give 78 mg (23%) of the title compound. HRMS m/z calcd for $C_{17}H_{20}N_4O_4$ (M)$^+$ 344.1485, found 344.1474.

Example 16

1-[2-(2,4-Difluorophenoxy)ethyl]-3-(1-piperazinyl)-2(1H)-pyrazinone

TMAD (0.129 g, 0.750 mmol) was added to a solution of 2-[3-(4-tert-butoxycarbonyl-1-piperazinyl)-pyrazinyloxy]ethanol (0.200 g, 0.620 mmol), triphenylphosphine (0.196 g, 1.23 mmol) and 2,4-difluorophenol (0.160 g, 1.23 mmol) in THF (1 mL) at room temperature. After being stirred for 2 h, the mixture was concentrated and put through a silica column using toluene/EtOAc (7:3) as eluent. Solvents were removed in vacuo and the resulting N-t-BOC derivative was treated with dichloromethane/TFA/H$_2$O (50:45:5; 5 mL) for 15 min with stirring. The mixture was concentrated and the residue purified by chromatography on silica gel using EtOAc/HOAc/MeOH/H$_2$O (20:3:3:2) as eluent. The product-containing fractions were concentrated, washed between dichloromethane/5% aqueous NaOH, and put through a silica column using dichloromethane/MeOH (8:2) as eluent to give 30 mg (14%) of the title compound. HRMS m/z calcd for $C_{16}H_{18}F_2N_4O_2$ (M)$^+$ 336.1398, found 336.1392.

Examples 17 and 18

General Procedure

TMAD (0.207 g, 1.20 mmol) was added to a mixture containing 2-[3-(4-tert-butoxycarbonyl-1-piperazinyl)-pyrazinyloxy]ethanol (0.325 g, 1.00 mmol), triphenylphosphine (0.328 g, 1.25 mmol) and the appropriate phenol (1.25 mmol). The reaction mixture was stirred until the starting material was consumed (by HPLC: 2-6 h) then concentrated and purified by chromatography on silica gel using toluene/EtOAc (9:1 to 1:1) as eluent. The N-BOC derivative of the title compound was treated with dichloromethane/TFA/H$_2$O (50:45:5; 5 mL) for 15 min with stirring. The mixture was concentrated and the residue purified by chromatography on silica gel using a gradient of dichloromethane→dichloromethane/MeOH (8:2) as eluent to provide the title compound.

Example 17

1-{2-[(2-Oxo-1,3-benzoxathiol-5-yl)oxy]ethyl}-3-(1-piperazinyl)-2(1H)-pyrazinone, Trifluoroacetate The title compound was prepared according to the procedure described above starting from 5-hydroxy-1,3-benzoxathiol-2-one (0.210 g, 1.25 mmol). Yield: 0.147 g (30%). HRMS m/z calcd for $C_{17}H_{18}N_4O_4S$ (M)$^+$ 374.1049, found 374.1044. Anal ($C_{17}H_{18}N_4O_4S.C_2F_3HO_2$) C, H, N.

Example 18

1-[2-(3-Hydroxyphenoxy)ethyl]-3-(1-piperazinyl)-2(1H)-pyrazinone, Trifluoroacetate The title compound was prepared according to the procedure described above starting from resorcinol (0.276 g, 0.250 mmol). Yield: 0.159 g (37%). HRMS m/z calcd for $C_{16}H_{20}N_4O_3$ (M)$^+$ 316.1535, found 316.1546.

Example 19

3-(1-Piperazinyl)-1-[2-(6-quinoxalinyloxy)ethyl]-2(1H)-pyrazinone, Hydrochloride TMAD (0.55 g, 3.20 mmol) was added to a stirred mixture of 2-[3-(4-tert-butoxycarbonyl-1-piperazinyl)-pyrazinyloxy]ethanol (1.00 g, 3.08 mmol), 6-hydroxyquinoxaline* (0.45 g, 3.08 mmol) and triphenylphosphine (0.85 g, 3.24 mmol) in THF (10 mL) at room temperature. After 20 h, the reaction mixture was concentrated and put through a silica column using toluene/EtOAc (1:1) as eluent. The chromatographic procedure was repeated once. Solvents were removed in vacuo and the resulting N-t-BOC derivative was treated with dichloromethane/TFA/H$_2$O (50:45:5; 20 mL) for 30 min with stirring. The reaction mixture was concentrated, dissolved in 0.1 M aqueous HCl and washed with toluene. The aqueous phase was frozen and lyophilized, dissolved in EtOH and concentrated to give 0.843 g (70%) of the title compound. HRMS m/z calcd for $C_{19}H_{20}N_6O_2$ (M)$^+$ 352.1648, found 352.1642.

*Prepared as described in J. Org. Chem. 1951, 16, 438-442.

Example 20

1-{2-[3-(N,N-Dimethylamino)phenoxy]ethyl}-3-(1-piperazinyl)-pyrazin-2(1H)-one, Fumarate 3-Dimethylaminophenol (0.97 g, 3.70 mmol), triphenylphosphine (0.97 g, 3.70 mmol) and TMAD (0.64 g, 3.70 mmol) were added to a stirred solution of 2-[3-(4-tert-butoxycarbonyl-1-piperazinyl)-pyrazinyloxy]ethanol (1.2 g, 3.7 mmol) in dry THF (10 mL) at room temperature. After 24 h, the reaction mixture was filtered and concentrated in vacuo. The residue was subjected to column chromatography on silica gel using toluene/EtOAc (3:1) containing 5% triethylamine as eluent to give 1.30 g (81%) of the N-t-BOC derivative of the title compound as an oil. This material (1.28 g, 2.89 mmol) was dissolved in dichloromethane (5 mL) and TFA (5 mL) was added. After being stirred at room temperature for 4 h, the reaction mixture was concentrated in vacuo. The residue was dissolved in dichloromethane and the solution was washed sequentially with 2 M aqueous NaOH, H$_2$O and brine. The organic layer was dried over MgSO$_4$ and concentrated in vacuo. The residue was purified by chromatography on silica gel using EtOAc/MeOH (3.5: 0.5) containing 5% triethylamine as eluent to furnish 0.35 g of the free base of the title compound. This material (1.03 mmol) was dissolved in dry MeOH (3 mL) and fumaric acid (0.12 g, 1.03 mmol) in dry MeOH (3 mL) was added dropwise. Diethyl ether was added dropwise. The precipitate formed was collected by filtration, washed with diethyl ether, dried, to give 0.37 g (22%) of the title compound; mp. 180-191° C. Anal. ($C_{18}H_{25}N_5O_2.C_4H_4O_4$) C, H, N.

Example 21

3-(1-Piperazinyl)-1-{2-[3-(trifluoromethyl)phenoxy]ethyl}-2(1H)-pyrazinone (TMAD; 129 mg, 0.75 mmol) was added to a mixture of 2-[3-(4-tert-butoxycarbonyl-1-piperazinyl)-pyrazinyloxy]ethanol (200 mg, 0.62 mmol), triphenylphosphine (323 mg, 1.23 mmol), 3-hydroxybenzotrifluoride (199 mg, 1.23 mmol) in THF (1.5 mL). After being stirred at room temperature for 1 h, the reaction mixture was concentrated in vacuo and the residue was purified by chromatography on silica gel using toluene/EtOAc (7:3) as eluent. The product-containing fractions were concentrated and the resulting N-t-BOC derivative was treated with dichloromethane/TFA/$H_2O$ (50:45:5) for 30 min with stirring. The mixture was concentrated in a speed vac overnight and the residue purified by chromatography on silica gel using $CHCl_3$/MeOH (9:1) as eluent to afford 109 mg (49%) of the title compound. HRMS m/z calcd for $C_{17}H_{19}F_3N_4O_2$ (M)$^+$ 368.1460, found 368.1465.

Examples 22-25

General Procedure

TMAD (256 mg, 1.5 mmol) was added to a mixture of 2-[3-(4-tert-butoxycarbonyl-1-piperazinyl)-pyrazinyloxy]ethanol (400 mg, 1.24 mmol), triphenylphosphine (646 mg, 2.46 mmol), and the appropriate phenol (1.23 mmol) in dry THF (3 mL) at room temperature. After being stirred for 4 h, the reaction mixture was concentrated in vacuo and the residue purified by chromatography on silica gel using toluene/EtOAc (8:2) as eluent. Solvents were removed in vacuo and the resulting N-t-BOC derivative of the title compound was treated with dichloromethane/TFA/$H_2O$ (50:45:5) for 30 min. The mixture was concentrated in a speed vac overnight. The residue was partitioned between 5 M aqueous NaOH/dichloromethane and the organic layer was dried over $K_2CO_3$. Removal of the solvent in vacuo and purification by chromatography on silica gel using $CHCl_3$/MeOH (9:1) as eluent gave the title compound.

Example 22

1-[2-(3-Fluorophenoxy)ethyl]-3-(1-piperazinyl)-2(1H)-pyrazinone

The title compound was prepared according to the procedure described above starting from 3-fluorophenol (276 mg, 1.23 mmol). Yield: 228 mg (58%). HRMS m/z calcd for $C_6H_{19}FN_4O_2$ (M)$^+$ 318.1492, found 318.1487.

Example 23

1-[2-(3-Nitrophenoxy)ethyl]-3-(1-piperazinyl)-2(1H)-pyrazinone

The title compound was prepared according to the general procedure described above starting from 3-nitrophenol (342 mg, 1.23 mmol). Yield: 195 mg (46%); mp 171° C. HRMS m/z calcd for $C_{16}H_{19}N_5O_4$ (M)$^+$ 345.1437, found 345.1420.

Example 24

1-[2-(3-Benzoylphenoxy)ethyl]-3-(1-piperazinyl)-2(1H)-pyrazinone

The title compound was prepared according to the general procedure described above starting from 3-benzoylphenol (488 mg, 1.23 mmol). Yield: 120 mg (24%); mp 69-70° C. HRMS m/z calcd for $C_{23}H_{24}N_4O_3$ (M)$^+$ 404.1848, found 404.1835.

Example 25

1-[2-(3,5-Difluorophenoxy)ethyl]-3-(1-piperazinyl)-2(1H)-pyrazinone

The title compound was prepared according to the general procedure described above starting from TMAD (384 mg, 2.25 mmol), 2-[3-(4-tert-butoxycarbonyl-1-piperazinyl)-pyrazinyloxy]ethanol (600 mg, 1.86 mmol), triphenylphosphine (969 mg, 3.69 mmol), 3,5-difluorophenol (239 mg, 1.84 mmol). Yield: 123 mg (20%); mp 119-121° C. HRMS m/z calcd for $C_{16}H_{18}F_2N_4O_2$ (M)$^+$ 336.1398, found 336.1409.

Examples 26-47

General Procedure

TMAD (103 mg, 0.60 mmol) was added to a mixture of 2-[3-(4-tert-butoxycarbonyl-1-piperazinyl)-pyrazinyloxy]ethanol (97 mg, 0.30 mmol; Examples 26-38); or 2-[3-(4-tert-butoxycarbonyl-3-methyl-1-piperazinyl)-pyrazinyloxy]ethanol* (102 mg, 0.30 mmol; Examples 39-43); or tert-Butyl 4-[3-(2-hydroxyethoxy)pyrazin-2-yl]-1,4-diazepane-1-carboxylate** (102 mg, 0.30 mmol; Examples 44-47), triphenylphosphine (157 mg, 0.60 mmol), and the appropriate phenol (0.60 mmol) in DMF (3.2 mL). The mixture was stirred under nitrogen at room temperature for approximately 18 h. The reaction mixture was filtered through a syringe with Celite and concentrated in a speed-vac. The N-t-BOC derivative of the title compound was dissolved in acetonitrile (1 mL) and purified by preparative HPLC. The product-containing fractions were pooled and concentrated in a speed-vac. N-Deprotection: The N-t-BOC intermediate was dissolved in dichloromethane (2 mL) and TFA (1 mL) was added at 0° C. The temperature was allowed to rise to room temperature and the mixture was stirred for 1 h. The reaction mixture was concentrated in a speed-vac to furnish the title compound.

*Prepared as described in Example 73. **Prepared as described in Example 75.

Example 26

1-[2-(Phenoxy)ethyl]-3-(1-piperazinyl)-2(1H)-pyrazinone, Trifluoroacetate

The title compound was prepared according to the procedure described above starting from phenol (56 mg, 0.60 mmol). Yield: 22 mg (18%). HPLC purity: 100%. MS m/z 301 (M+H)$^+$. HRMS m/z calcd for $C_{16}H_{20}N_4O_2$ (M)$^+$ 300.1586, found 300.1575.

Example 27

1-[2-(2,6-Difluorophenoxy)ethyl]-3-(1-piperazinyl)-2(1H)-pyrazinone, Trifluoroacetate The title compound was prepared according to the procedure described above starting from 2,6-difluorophenol (78 mg, 0.60 mmol). Yield: 55 mg (41%). HPLC purity: 99%. MS m/z 337 (M+H)$^+$. HRMS m/z calcd for $C_{16}H_{18}F_2N_4O_2$ (M)$^+$ 336.1398, found 336.1400.

Example 28

1-[2-(2-Cyanophenoxy)ethyl]-3-(1-piperazinyl)-2(1H)-pyrazinone, Trifluoroacetate The title compound was prepared according to the procedure described above starting from 2-cyanophenol (71 mg, 0.60 mmol). Yield: 47 mg (36%). HPLC purity: 96%. MS m/z 326 (M+H)$^+$. HRMS m/z calcd for $C_{17}H_{19}N_5O_2$ (M)$^+$ 325.1539, found 325.1536.

Example 29

1-[2-(4-Trifluoromethylphenoxy)ethyl]-3-(1-piperazinyl)-2(1H)-pyrazinone, Trifluoroacetate The title compound was prepared according to the procedure described above starting from 4-trifluoromethylphenol (97 mg, 0.60 mmol). Yield: 20 mg (14%). HPLC purity: 100%. MS m/z 369 (M+H)$^+$. HRMS m/z calcd for $C_{17}H_{19}F_3N_4O_2$ (M)$^+$ 368.1460, found 368.1465.

Example 30

1-[2-(4-Bromophenoxy)ethyl]-3-(1-piperazinyl)-2(1H)-pyrazinone, Trifluoroacetate The title compound was prepared according to the procedure described above starting from 4-bromophenol (104 mg, 0.60 mmol). Yield: 29 mg (20%). HPLC purity: 99%. MS m/z 380 (M+H)$^+$. HRMS m/z calcd for $C_{16}H_{19}BrN_4O_2$ (M)$^+$ 378.0691, found 378.0680.

Example 31

1-[2-{4-Phenoxy-(phenoxy)}ethyl]-3-(1-piperazinyl)-2(1H)-pyrazinone, Trifluoroacetate The title compound was prepared according to the procedure described above starting from 4-phenoxyphenol (112 mg, 0.60 mmol). Yield: 20 mg (13%). HPLC purity: 96%. MS m/z 393 (M+H)$^+$. HRMS m/z calcd for $C_{22}H_{24}N_4O_3$ (M)$^+$ 392.1848, found 392.1856.

Example 32

1-[2-(4-Fluorophenoxy)ethyl]-3-(1-piperazinyl)-2(1H)-pyrazinone, Trifluoroacetate The title compound was prepared according to the procedure described above starting from 4-fluorophenol (67 mg, 0.60 mmol). Yield: 36 mg (28%). HPLC purity: 100%. MS m/z 319 (M+H)$^+$. HRMS m/z calcd for $C_{16}H_{19}FN_4O_2$ (M)$^+$ 318.1492, found 318.1505.

Example 33

1-[2-(4-Isopropylphenoxy}ethyl]-3-(1-piperazinyl)-2(1H)-pyrazinone, Trifluoroacetate The title compound was prepared according to the procedure described above starting from 4-isopropylphenol (82 mg, 0.60 mmol). Yield: 59 mg (43%). HPLC purity: 99%. MS m/z 343 (M+H)$^+$. HRMS m/z calcd for $C_{19}H_{26}N_4O_2$ (M)$^+$ 342.2056, found 342.2062.

Example 34

1-[2-(2,4,5-Trichlorophenoxy)ethyl]-3-(1-piperazinyl)-2(1H)-pyrazinone, Trifluoroacetate The title compound was prepared according to the procedure described above starting from 2,4,5-trichlorophenol (118 mg, 0.60 mmol). Yield: 2.4 mg (2%). HPLC purity: 97%. MS m/z 403 (M+H)$^+$.

Example 35

1-[2-(2-Methylthiophenoxy)ethyl]-3-(1-piperazinyl)-2(1H)-pyrazinone, Trifluoroacetate The title compound was prepared according to the procedure described above starting from 2-methylsulfanyl-phenol (84 mg, 0.60 mmol). Yield: 38 mg (36%). HPLC purity: 97%. MS m/z 347 (M+H)$^+$. HRMS m/z calcd for $C_{17}H_{22}N_4O_2S$ (M)$^+$ 346.1463, found 346.1471.

Example 36

1-[2-(3-Methoxyphenylthio)ethyl]-3-(1-piperazinyl)-2(1H)-pyrazinone, Trifluoroacetate The title compound was prepared according to the procedure described above starting from 3-methoxy-thiophenol (84 mg, 0.60 mmol). Yield: 23 mg (22%). HPLC purity: 85%. MS m/z 347 (M+H)$^+$. HRMS m/z calcd for $C_{17}H_{22}N_4O_2S$ (M)$^+$ 346.1463, found 346.1468.

Example 37

1-[2-{(4-Allyl-2-methoxy)phenoxy}ethyl]-3-(1-piperazinyl)-2(1H)-pyrazinone, Trifluoroacetate The title compound was prepared according to the procedure described above starting from 4-allyl-2-methoxyphenol (99 mg, 0.60 mmol). Yield: 69 mg (47%). HPLC purity: 98%. MS m/z 371 (M+H)$^+$. HRMS m/z calcd for $C_{20}H_{26}N_4O_3$ (M)$^+$ 370.2005, found 370.2013.

Example 38

1-[2-(5,6,7,8-Tetrahydro-naphthalen-2-yloxy)ethyl]-3-(1-piperazinyl)-2(1H)-pyrazinone, Trifluoroacetate The title compound was prepared according to the procedure described above starting from 5,6,7,8-tetrahydro-naphthalen-2-ol (89 mg, 0.60 mmol). Yield: 26 mg (19%). HPLC purity: 96%. MS m/z 355 (M+H)$^+$. HRMS m/z calcd for $C_{20}H_{26}N_4O_2$ (M)$^+$ 354.2056, found 354.2070.

Example 39

1-[2-(2,6-Difluorophenoxy)ethyl]-3-(3-methyl-1-piperazinyl)-2(1H)-pyrazinone, Trifluoroacetate The title compound was prepared according to the procedure described above starting from 2,6-difluorophenol (78 mg, 0.60 mmol). Yield: 71 mg (51%). HPLC purity: 99%. MS m/z 351 (M+H)$^+$. HRMS m/z calcd for $C_{17}H_{20}F_2N_4O_2$ (M)$^+$ 350.1554, found 350.1539.

Example 40

1-[2-(4-Trifluoromethylphenoxy)ethyl]-3-(3-methyl-1-piperazinyl)-2(1H)-pyrazinone, Trifluoroacetate The title compound was prepared according to the procedure described above starting from 4-trifluoromethylphenol (97 mg, 0.60 mmol). Yield: 82 mg (55%). HPLC purity: 99%. MS m/z 383 (M+H)$^+$. HRMS m/z calcd for $C_{18}H_{21}F_3N_4O_2$ (M)$^+$ 382.1617, found 382.1617.

Example 41

1-[2-(4-Bromophenoxy)ethyl]-3-(3-methyl-1-piperazinyl)-2(1H)-pyrazinone, Trifluoroacetate The title compound was prepared according to the procedure described above starting from 4-bromophenol (104 mg, 0.60 mmol). Yield: 79 mg (52%). HPLC purity: 98%. MS m/z 394 (M+H)$^+$. HRMS m/z calcd for $C_{17}H_{21}BrN_4O_2$ (M)$^+$ 392.0848, found 392.0857.

Example 42

1-[2-(Phenoxy)ethyl]-3-(3-methyl-1-piperazinyl)-2(1H)-pyrazinone, Trifluoroacetate The title compound was prepared according to the procedure described above starting from phenol (56 mg, 0.60 mmol). Yield: 30 mg (32%). HPLC purity: 100%. MS m/z 315 (M+H)$^+$. HRMS m/z calcd for $C_{17}H_{22}N_4O_2$ (M)$^+$ 314.1743, found 314.1746.

Example 43

1-[2-(2,4,5-Trifluorophenoxy)ethyl]-3-(3-methyl-1-piperazinyl)-2(1H)-pyrazinone, Trifluoroacetate The title compound was prepared according to the procedure described above starting from 2,4,5-trifluorophenol (89 mg, 0.60 mmol). Yield: 25 mg (22%). HPLC purity: 100%. MS m/z 369 (M+H)$^+$. HRMS m/z calcd for $C_{17}H_{19}F_3N_4O_2$ (M)$^+$ 368.1460, found 368.1473.

Example 44

1-[2-(2,4,5-Trifluorophenoxy)ethyl]-3-(1,4-diazepan-1-yl)-2(1H)-pyrazinone, Trifluoroacetate The title compound was prepared according to the procedure described above starting from 2,4,5-trifluorophenol (89 mg, 0.60 mmol). Yield: 56 mg (51%). HPLC purity: 98%. MS m/z 369 (M+H)$^+$. HRMS m/z calcd for $C_{17}H_{19}F_3N_4O_2$ (M)$^+$ 368.1460, found 368.1454.

Example 45

1-[2-(4-Fluorophenoxy)ethyl]-3-(1,4-diazepan-1-yl)-2(1H)-pyrazinone, Trifluoroacetate The title compound was prepared according to the procedure described above starting from 4-fluorophenol (67 mg, 0.60 mmol). Yield: 65 mg (65%). HPLC purity: 99%. MS m/z 333 (M+H)$^+$. HRMS m/z calcd for $C_{17}H_{21}FN_4O_2$ (M)$^+$ 332.1649, found 332.1651.

Example 46

1-[2-(4-Isopropylphenoxy)ethyl]-3-(1,4-diazepan-1-yl)-2(1H)-pyrazinone, Trifluoroacetate The title compound was prepared according to the procedure described above starting from 4-isopropylphenol (82 mg, 0.60 mmol). Yield: 49 mg (46%). HPLC purity: 99%. MS m/z 357 (M+H)$^+$. HRMS m/z calcd for $C_{20}H_{28}N_4O_2$ (M)$^+$ 356.2212 found 356.2203.

Example 47

1-[2-{(2-Methylthio)phenoxy}ethyl]-3-(1,4-diazepan-1-yl)-2(1H)-pyrazinone, Trifluoroacetate The title compound was prepared according to the procedure described above starting from 2-methylsulfanyl-phenol (84 mg, 0.60 mmol). Yield: 51 mg (47%). HPLC purity: 98%. MS m/z 361 (M+H)$^+$. HRMS m/z calcd for $C_{18}H_{24}N_4O_2S$ (M)$^+$ 360.1620, found 360.1611.

Example 48

1-(2,4,5-Trifluorobenzyl)-3-(1-piperazinyl)-2(1H)-pyrazinone, Trifluoroacetate

Step 1: 3-(4-tert-Butoxycarbonyl-1-piperazinyl)-2(1H)-pyrazinone.

2-Chloro-3-(4-tert-butoxycarbonyl-1-piperazinyl)pyrazine* (60 g, 0.20 mol) was added to a mixture of NaOH (100 g, 2.50 mol), water (100 mL) and DMSO (100 g) at 100° C. After being stirred for 3 h, the mixture was allowed to cool and partitioned between toluene (100 g) and water (200 mL). Water (300 mL), crushed ice (200 g), EtOAc (600 g) and sodium chloride (100 g) were added to the aqueous layer. The layers were separated and the aqueous layer was extracted with an additional portion of EtOAc (600 g). The combined organic layers were concentrated in vacuo to furnish 38 g (68%) of the title product. $^1$H and $^{13}$C NMR data support the stated structure. HPLC purity: 100%. HRMS m/z calcd for $C_{13}H_{20}N_4O_3$ (M)$^+$ 280.1535, found 280.1530.

*Prepared according to the procedure described in WO 00/76984, Example 52, Step 1.

Step 2. 1-(2,4,5-Trifluorobenzyl)-3-(4-tert-butoxycarbonyl-1-piperazinyl)-2(1H)-pyrazinone.

To a solution of 3-(4-tert-butoxycarbonyl-1-piperazinyl)-2(1H)-pyrazinone (obtained in Step 1 above; 1.30 g, 4.66 mmol) in THF (20 mL) was added t-BuOK (0.53 g, 4.66 mmol) and the mixture was stirred at room temperature for 10 min. The resulting solution was added dropwise to a stirred solution of 2,4,5-trifluorobenzyl bromide (1.20 g, 5.33 mmol) in THF (20 mL) at room temperature. After 2 h, the reaction mixture was cooled to 0° C. and partitioned between water (20 mL) and EtOAc (50 mL). The organic layer was washed with brine (10 mL) and dried over Na$_2$SO$_4$. Evaporation of the solvent gave 1.82 g (96%) of the title compound as an oil which crystallized upon standing. The product can be recrystallized from tert-butyl methyl ether. HPLC purity: 94%. $^1$NMR and MS analyses support the stated structure.

Step 3. 1-(2,4,5-Trifluorobenzyl)-3-(1-piperazinyl)-2(1H)-pyrazinone, Trifluoroacetate.

To a solution of 1-(2,4,5-trifluorobenzyl)-3-(4-tert-butoxycarbonyl-1-piperazinyl)-2(1H)-pyrazinone (obtained in Step 2 above; 0.50 g, 1.18 mmol) in dichloromethane (10 mL) was added TFA (2 mL) dropwise at 0° C. After being stirred for 1 h at room temperature, the solvent and TFA were removed in vacuum resulting in a colorless oil. Trituration with ether gave white crystals which were filtered off after cooling the mixture to 0° C. The crystals were washed with cold ether and dried in vacuum at 50° C. to furnish 0.50 g (98%) of the title compound. HPLC purity: 95%. $^1$H NMR analysis supports the stated structure. HRMS m/z calcd for $C_{15}H_{15}F_3N_4O$ (M)$^+$ 324.1198, found 324.1195.

Example 49

1-[3-(2,4,5-Trifluorophenyl)propyl]-3-(1-piperazinyl)-2(1H)-pyrazinone, Trifluoroacetate Step 1. 3-(2,4,5-Trifluorophenyl)propionic acid.

3-(2,4,5-Trifluorophenyl)acrylic acid (3.50 g, 17.3 mmol) was dissolved in glacial acetic acid (40 mL) and treated with active carbon (~0.5 g). The mixture was stirred for 20 min, the carbon filtered off and washed with glacial acetic acid (20 mL). To the resulting solution Pd on carbon catalyst (0.45 g, 10% Pd) was added and the mixture was stirred under hydrogen at atmospheric pressure overnight. The suspension was filtered and concentrated in vacuo. Residual acetic acid was removed by addition of a small volume of toluene followed by concentration in vacuo. The resulting oil crystallized upon standing and this material was dried in vacuum at 50° C. to give 3.34 g (95%) of the title compound.

Step 2. 3-(2,4,5-Trifluorophenyl)propan-1-ol.*

3-(2,4,5-Trifluorophenyl)propionic acid (3.25 g, 16.0 mmol; from Step 1) was dissolved in THF (15 mL) and cooled to 0° C. To this solution was added $Me_2S.BH_3$ (3.2 mL, ~32 mmol) dropwise under 30 min and the resulting mixture was then heated at 70° C. for 30 min. After cooling to 0° C., 6 M aqueous HCl (20 mL) was added dropwise. The mixture was heated at 70° C. for 1 h. After cooling to room temperature the mixture was extracted with ether (2×20 mL) and the combined organic layers were washed with brine and dried over $Na_2SO_4$. Evaporation and drying in vacuum gave the title compound as a colorless liquid (3.17 g, 97% pure by HPLC) that was used directly in the next step.

*Previously reported in EP 369812.

Step 3. 3-(2,4,5-Trifluorophenyl)propyl Methanesulfonate.

Methanesulfonyl chloride (0.45 g, 3.88 mmol) was added dropwise to a solution of 3-(2,4,5-trifluorophenyl)propan-1-ol (0.46 g, 2.41 mmol; from Step 2) and triethylamine (0.71 g, 7.0 mmol) in dichloromethane (5 mL) at 0° C. The mixture was stirred at room temperature for 2 h. After complete disappearance of the alcohol (HPLC monitoring), dichloromethane (10 mL) and water (10 mL) were added. The aqueous phase was saturated with NaCl and extraction performed. The organic layer was washed with brine, dried over $Na_2SO_4$ and concentrated in vacuo to give 0.66 g (100%) of the title compound as a yellow oil. Purity by HPLC: 87%. This material was used directly in the next step.

Step 4: 1-[3-(2,4,5-Trifluorophenyl)propyl]-3-(4-tert-butoxycarbonyl-1-piperazinyl)-2(1H)-pyrazinone.

To a solution of 3-(4-tert-butoxycarbonyl-1-piperazinyl)-2(1H)-pyrazinone (obtained in Example 48, Step 1; 0.53 g, 1.91 mmol) in THF (10 mL) was added t-BuOK (0.21 g, 1.91 mmol) and the mixture was stirred at room temperature for 10 min. The resultant mixture was added dropwise to a solution of 3-(2,4,5-trifluorophenyl)propyl methanesulfonate (0.66 g, ~2.1 mmol; from Step 3) in THF (10 mL). The mixture was stirred at 35° C. for 3 days. Then, the solution was cooled to 0° C. and water (20 mL) and EtOAc (25 mL) were added. The aqueous phase was saturated with NaCl (2 g) and extraction performed. After separation and repeated extraction with EtOAc (15 mL) the combined organic layers were washed with brine and dried over $Na_2SO_4$. Concentration in vacuum gave 0.75 g of a yellowish oil which was purified by column chromatography on silica gel using EtOAc/n-hexane (4:1) as eluent. This gave 0.50 g (57%) of the title compound as a colorless oil. HPLC purity: 91%. $^1$H NMR and MS analyses support the stated structure.

Step 5. 1-[3-(2,4,5-Trifluorophenyl)propyl]-3-(1-piperazinyl)-2(1H)-pyrazinone, Trifluoroacetate.

TFA (2 mL) was added dropwise to a solution of 1-[3-(2,4,5-trifluorophenyl)propyl]-3-(4-tert-butoxycarbonyl-1-piperazinyl)-2(1H)-pyrazinone (0.46 g, 1.02 mmol; from Step 4) in dichloromethane (10 mL) at 0° C. After being stirred for 1 h at room temperature, the solvent and TFA were removed in vacuo resulting in a colorless oil. Trituration with ether gave pale white crystals which were filtered off after cooling the mixture to 0° C. The crystals were washed with cold ether and dried in vacuum at 50° C. to furnish 0.38 g (79%) of the title compound. HPLC purity: 96%. $^1$H NMR analysis supports the stated structure. HRMS m/z calcd for $C_{17}H_{19}F_3N_4O$ (M)$^+$ 352.1511, found 352.1524.

Example 50

1-(2,3-Dihydro-benzo[1,4]dioxin-2-ylmethyl)-3-(1-piperazinyl)-2(1H)-pyrazinone, Trifluoroacetate Step 1: 1-(2,3-Dihydro-benzo[1,4]dioxin-2-ylmethyl)-3-(4-tert-butoxycarbonyl-1-piperazinyl)-2(1H)-pyrazinone.

A mixture of 3-(4-tert-butoxycarbonyl-1-piperazinyl)-2(1H)-pyrazinone (4.00 g, 14.3 mmol; from Example 48, Step 1), 2-chloromethyl-2,3-dihydro-benzo[1,4]dioxine (2.60 g, 14.3 mmol), DMF (10 g) and potassium carbonate (4.00 g, 28.9 mmol) was heated at 120° C. for 3 h. Water (100 g) and EtOAc (200 g) were added to the reaction mixture and the layers were separated. The organic layer was concentrated and the residue purified by chromatography on a MPLC column using a continuous gradient (0-100% EtOAc in heptane) as eluent. This provided 0.60 g (15%) of the title compound as an oil. $^1$H NMR analysis supports the stated structure.

Step 2: 1-(2,3-Dihydro-benzo[1,4]dioxin-2-ylmethyl)-3-(1-piperazinyl)-2(1H)-pyrazinone, Trifluoroacetate.

Trifluoroacetic acid (5 g) was added to a mixture of 1-(2,3-dihydro-benzo[1,4]dioxin-2-ylmethyl)-3-(4-tert-butoxycarbonyl-1-piperazinyl)-2(1H)-pyrazinone (0.6 g, 1.4 mmol; from Step 1) and dichloromethane (20 g). The mixture was stirred overnight and then concentrated in vacuo. Methyl tert-butyl ether (40 g) was added to the residue and the crystals that formed instantly were collected. This furnished 0.30 g (48%) of the title compound as white crystals. HPLC purity: 97%. MS and NMR analyses support the stated structure. HRMS m/z calcd for $C_{17}H_{20}N_4O_3$ (M)$^+$ 328.1535, found 328.1538.

Example 51

3-Piperazin-1-yl-1-[2-(2,4,5-trifluoro-phenoxy)-ethyl]-1H-quinoxalin-2-one, Trifluoroacetate Step 1: 4-(3-Chloro-quinoxalin-2-yl)-piperazine-1-carboxylic acid tert-butyl ester.

Di-tert-butyl dicarbonate (5.8 g, 0.027 mol) was added to a mixture of 2-chloro-3-piperazin-1-yl-quinoxalin* (6.6 g, 0.027 mol), triethylamine (5.5 g, 0.054 mol) and dichloromethane (100 g) at 0° C. The mixture was stirred at room temperature overnight. Toluene (300 g) and water (100 g) were added to the reaction mixture and the layers were separated. The organic layer was concentrated in vacuo to furnish 9.4 g (100%) of the title compound. $^1$H NMR analysis supports the stated structure.
*Reported in WO 00/76984, Example 162, Step 1.

Step 2: 4-(3-Oxo-3,4-dihydro-quinoxalin-2-yl)-piperazine-1-carboxylic acid tert-butyl ester.

4-(3-Chloro-quinoxalin-2-yl)-piperazine-1-carboxylic acid tert-butyl ester (10.0 g, 28.7 mmol; from Step 1) was added to a mixture of sodium hydroxide (40 g), water (40 g) and DMSO (40 g) at 100° C. After being stirred for 1 h at this temperature, water (200 g) and methyl tert-butyl ether (1000 g) and sodium chloride (50 g) were added. The crystals formed from the organic layer were collected by filtration and dried. This furnished 4.0 g (42%) of the title compound as white crystals. $^1$H NMR analysis supports the stated structure.

Step 3: 4-{3-Oxo-4-[2-(2,4,5-trifluoro-phenoxy)-ethyl]-3,4-dihydro-quinoxalin-2-yl}-piperazine-1-carboxylic acid tert-butyl ester.

t-BuOK (1.0 g, 8.9 mmol) was added to a mixture of 4-(3-oxo-3,4-dihydro-quinoxalin-2-yl)-piperazine-1-carboxylic acid tert-butyl ester (1 g, 9 mmol; from Step 2), THF (20 g) and DMSO (5 g) at room temperature. This mixture is added to a solution of 2-(2,4,5-trifluorophenoxy)ethyl methanesulfonate (2.45 g, 9.00 mmol; from Example 54, Step 4) in THF (20 g). After being stirred at room temperature overnight, water (100 g) and EtOAc (200 g) were added to the reaction mixture. The layers were separated and the organic layer was concentrated in vacuo. The residue was purified by chromatography on an MPLC-columnn using a continuous gradient (0-100% EtOAc in heptane) as eluent. Evaporation of solvent gave 0.5 g of the title compound as greasy crystals (not pure). $^1$H NMR analysis supports the stated structure. This material was used directly in the next step.

Step 4: 3-Piperazin-1-yl-1-[2-(2,4,5-trifluoro-phenoxy)-ethyl]-1H-quinoxalin-2-one, Trifluoroacetate.

Trifluoroacetic acid (5 g) was added to a mixture of 4-{3-oxo-4-[2-(2,4,5-trifluoro-phenoxy)-ethyl]-3,4-dihydro-quinoxalin-2-yl}-piperazine-1-carboxylic acid tert-butyl ester (0.5 g, 1 mmol; from Step 3) and dichloromethane (20 g). After being stirred at room temperature for 2 h, the reaction mixture was concentrated in vacuo. The residue was purified by chromatography (prep-HPLC) to give 0.12 g (23%) of the title compound. $^1$H NMR and MS analyses support the stated structure. HPLC purity: 94%. HRMS m/z calcd for $C_{20}H_{19}F_3N_4O_2$ (M)$^+$ 404.1460, found 404.1475.

Example 52

1-[2-(2,4,5-Trifluorophenoxy)ethyl]-3-(4-n-butyl-1-piperazinyl)-2(1H)-pyrazinone Step 1: Methanesulfonic acid n-butyl ester*

Methanesulfonyl chloride (15.45 g, 0.13 mol) was added to a mixture of n-butanol (10 g, 0.13 mol), triethylamine (26.3 g, 0.26 mol) and dichloromethane (150 g) at 10° C. After being stirred at room temperature overnight, water (100 g) was added to the reaction mixture and the layers were separated. The organic layer was concentrated in vacuo at room temperature. This gave 18 g (90%) of the title mesylate as an oil. $^1$H NMR analysis supports the stated structure.
*Previously described in J. Am. Chem. Soc. 1933, 55, 345-349.

Step 2:1-[2-(2,4,5-Trifluorophenoxy)ethyl]-3-(4-n-butyl-1-piperazinyl)-2(1H)-pyrazinone.

Methanesulfonic acid butyl ester (0.30 g, 1.97 mmol; from Step 1) was added to a mixture of 3-(1-piperazinyl)-1-[2-(2,4,5-trifluorophenoxy)ethyl]-2(1H)-pyrazinone (0.50 g, 1.4 mmol; from the free base of Example 3) and potassium carbonate (0.10 g, 2.89 mmol) in DMSO (3 g). After being stirred for 3 h at 60° C., water (50 g) and EtOAc (100 g) were added to the reaction mixture. The layers were separated and the organic layer was concentrated in vacuo. The residue was purified by chromatography on a MPLC column using a continuous gradient (0-100% EtOAc in heptane) as eluent. This furnished 33 mg (8%) of the title compound as an oil. $^1$H NMR analysis supports the stated structure. HPLC purity: 100%. HRMS m/z calcd for $C_{20}H_{25}F_3N_4O_2$ (M)$^+$ 410.1930, found 410.1920.

Example 53

1-[2-(2,4,5-Trifluorophenoxy)ethyl]-3-[4-(2-methoxyethyl)-1-piperazinyl]-2(1H)-pyrazinone, Trifluoroacetate.

Step 1: Methanesulfonic acid 2-methoxy-ethyl ester.*

Methanesulfonyl chloride (15 g, 0.13 mol) was added to a mixture of 2-methoxy ethanol (10 g, 0.13 mol), triethylamine (26.5 g, 0.26 mol) and dichloromethane (150 g) at 0° C. After being stirred at room temperature overnight, water (100 g) was added to the reaction mixture. The layers were separated and the organic layer was concentrated in vacuo at room temperature. This gave 13.1 g (65%) of the title mesylate as an oil. $^1$H NMR analysis supports the stated structure.
*Previously reported in Tetrahedron 1995, 51, 4867-4890.

Step 2: 1-[2-(2,4,5-Trifluorophenoxy)ethyl]-3-[4-(2-methoxyethyl)-1-piperazinyl]-2(1H)-pyrazinone, Trifluoroacetate.

Methanesulfonic acid 2-methoxy-ethyl ester (0.15 g, 0.97 mmol; from Step 1) was added to a mixture of 3-(1-piperazinyl)-1-[2-(2,4,5-trifluorophenoxy)ethyl]-2(1H)-pyrazinone (0.30 g, 0.85 mmol; from the free base of Example 3) and potassium carbonate (0.30 g, 2.17 mmol) in DMSO (6 g). After being stirred at 60° C. for 3 h, water (5 g) and EtOAc (30 g) were added to the reaction mixture. The layers were separated and the organic layer concentrated in vacuo. The residue (0.2 g) was purified by chromatography (prep-HPLC) to furnish 60 mg (13%) of the title compound. $^1$H NMR and MS analyses support the stated structure. HPLC purity: 95%.

Example 54

1-[2-(2,4,5-Trifluorophenoxy)ethyl]-3-(4-methyl-1-piperazinyl)-2(1H)-pyrazinone

Step 1. 1-(3-Chloro-2-pyrazinyl)-4-methylpiperazine.*

A mixture of 2,3-dichloropyrazine (5.0 g, 34 mmol), N-methylpiperazine (5.1 g, 51 mmol) and potassium carbonate (7.0 g, 51 mmol) in acetonitrile (100 mL) was stirred at ambient temperature for 2 h. Addition of hexane, followed by filtration and concentration of the filtrate gave 7.3 g of the crude product as an orange liquid. Purification by filtration through silica using heptane/EtOAc (3:1) followed by EtOAc/acetone (1:1) gave 4.1 g (57%) of the title compound as a yellow oil which solidified upon cooling. HPLC purity: 100%. MS m/z 213 (M+H)⁺.

*Reported in WO 00/76984, Example 169, Step 1.

Step 2. 3-(4-Methyl-1-piperazinyl)-2(1H)-pyrazinone.

To a solution of NaOH (5.4 g, 125 mmol) in a mixture of water/DMSO (1:1; 15 mL) at 80° C. was added 1-(3-chloro-2-pyrazinyl)-4-methylpiperazine (obtained in Step 1 above; 2.5 g, 12 mmol). After being stirred for 2 h, the dark red solution was cooled to room temperature, extracted with EtOAc overnight to give, after drying and solvent removal in vacuo, 0.96 g (43%) of the title compound as an off-white solid. HPLC purity: 88%. MS m/z 195 (M+H)⁺. HRMS m/z calcd for $C_9H_{14}N_4O$ (M)⁺ 194.1168, found 194.1159.

Step 3. 2-(2,4,5-Trifluorophenoxy)ethanol.

t-BuOK (3.0 g, 27 mmol) was added to a mixture of 1,2,4,5-tetrafluorobenzene (2.0 g, 13.3 mmol) and ethylene glycol (7.5 mL, 133 mmol) in DMSO (50 mL) and heated at 80° C. for 1 h and then at 60° C. overnight. EtOAc was added and the resulting solution was washed several times with water. The organic layer was dried ($Na_2SO_4$) and concentrated carefully in vacuo at 30° C. to furnish 1.5 g (containing ~14% EtOAc) of the title compound as a white semisolid. NMR analysis supports the stated structure. This material was used directly in the next step.

Step 4. 2-(2,4,5-Trifluorophenoxy)ethyl Methanesulfonate.

Triethylamine (1.8 mL, 13.2 mmol) was added to a cold (0° C.) solution of a mixture of the 2-(2,4,5-trifluorophenoxy)ethanol (1.3 g, 6.6 mmol; from Step 3) and methanesulfonyl chloride (0.61 mL, 7.9 mmol) in dichloromethane (40 mL). After being stirred for 1.5 h, water was added and the mixture was concentrated. The residue was dissolved in EtOAc and the solution was washed with 1 M $KHSO_4$, then with brine, dried ($Na_2SO_4$) and concentrated to give 1.78 g (quantitative yield) of the title compound as an orange oil. NMR analysis supports the stated structure. This material was used directly in the next step.

Step 5. 1-[2-(2,4,5-Trifluorophenoxy)ethyl]-3-(4-methyl-1-piperazinyl)-2(1H)-pyrazinone.

A mixture of 3-(4-methyl-1-piperazinyl)-2(1H)-pyrazinone (obtained in Step 2 above; 0.5 g, 2.6 mmol) and t-BuOK (440 mg, 3.90 mmol) in THF (40 mL) was stirred until the mixture became thick (about 10 min), and then a solution of 2-(2,4,5-trifluorophenoxy)ethyl methanesulfonate (0.90 g, 2.2 mmol; from Step 4) in THF (10 mL) was added. After being stirred for 5 days at ambient temp, HPLC showed only 50% conversion. The reaction solution was then heated to 60° C. overnight which gave almost full conversion. The reaction was worked up according to the following: water was added, THF was evaporated off and the aqueous mixture was extracted twice with EtOAc, dried ($Na_2SO_4$) and concentrated to yield 1.08 g of the crude product as a yellow oil. Purification by chromatography on silica gel [eluent: 2% MeOH in $CHCl_3$+$NH_3$ (g)] gave the title compound as a yellow oil, which solidified upon cooling. Yield: 304 mg (32%). HPLC purity: 100%. MS m/z 369 (M+H)⁺. HRMS m/z calcd for $C_{17}H_{19}F_3N_4O_2$ (M)⁺ 368.1460, found 368.1462.

Example 55

1-[2-(2,4,5-Trifluorophenoxy)ethyl]-3-(4-isopropyl-1-piperazinyl)-2(1H)-pyrazinone Step 1: 2-Chloro-3-(4-isopropylpiperazin-1-yl)pyrazine.

A mixture 2,3-dichloro-pyrazine (5.0 g, 34 mmol), 1-isopropylpiperazine (6.5 g, 51 mmol) and potassium carbonate (7.0 g, 51 mmol) in acetonitrile (100 mL) was stirred at ambient temperature for 2 h. Addition of hexane, followed by filtration and concentration of the filtrate gave 9.5 g of crude material as an orange liquid. Purification by filtration through silica using heptane/EtOAc (3:1), followed by EtOAc/acetone (1:1), provided 6.5 g (79%) of the title compound as a yellow oil which solidified upon cooling. HPLC purity: 98%. MS m/z 241 (M+H)⁺. HRMS m/z calcd for $C_{11}H_{17}ClN_4$ (M)⁺ 240.1142, found 240.1138.

Step 2: 3-(4-Isopropyl-1-piperazinyl)-2(1H)-pyrazinone.

To a solution of NaOH (5.4 g, 125 mmol) in a mixture of water/DMSO (1: 1; 15 mL) was added 2-chloro-3-(4-isopropylpiperazin-1-yl)pyrazine (2.66 g, 12 mmol; from Step 1). After being stirred at 80° C. for 2 h, the dark red solution was cooled to room temperature, extracted with EtOAc overnight to give, after drying and solvent removal in vacuo, 2.6 g (70%) of the title compound as a white solid. HPLC purity: 87%. MS m/z 223 (M+H)⁺. HRMS m/z calcd for $C_{11}H_{18}N_4O$ (M)⁺ 222.1481, found 222.1489.

Step 3: 1-[2-(2,4,5-Trifluorophenoxy)ethyl]-3-(4-isopropyl-1-piperazinyl)-2(1H)-pyrazinone.

A mixture of 3-(4-isopropyl-1-piperazinyl)-2(1H)-pyrazinone (0.58 g, 2.6 mmol; from Step 2) and t-BuOK (440 mg, 3.90 mmol) in THF (40 mL) was stirred until the mixture became thick (about 10 min), and then a solution of 2-(2, 4,5-trifluorophenoxy)ethyl methanesulfonate (0.90 g, 2.2 mmol; from Example 54, Step 4) in THF (10 mL) was added. After being stirred for 5 days at ambient temperature, HPLC showed only 25% conversion. The reaction solution was then heated to 60° C. overnight which gave almost full conversion. The reaction was worked up according to the following: water was added, THF was evaporated off and the aqueous mixture was extracted twice with EtOAc, dried and concentrated to yield 1.18 g of the crude product as a yellow oil. Purification by chromatography on silica gel (eluent: 2.5% MeOH in $CHCl_3$+$NH_3$ (g)) gave the title compound as a colourless oil, which solidified upon cooling. Yield: 120 mg (14%). HPLC purity: 99%. MS m/z 397 (M+H)⁺. HRMS m/z calcd for $C_{19}H_{23}F_3N_4O_2$ (M)⁺ 396.1773, found 396.1771.

Example 56

1-{2-[(5-Methyl[1,2,4]triazolo[1,5-a]pyrimidin-7-yl)oxy]ethyl}-3-(1-piperazinlyl)-2(1H)-pyrazinone, Hydrochloride DEAD (0.485 μL, 3.08 mmol) was added to a stirred solution of 2-[3-(4-tert-butoxycarbonyl-1-piperazinyl)-pyrazinyloxy]ethanol (1.00 g, 3.08 mmol), 5-methyl-s-triazolo[1,5-a]pyrimidin-7-ol (0.465 g, 3.08 mmol) and triphenylphosphine (0.85 g, 3.24 mmol) in THF (10 ml). After being stirred for 2 h, the reaction mixture was concentrated and put through a silica column using toluene/EtOAc (1:1) as eluent. The obtained N-t-BOC derivative of the title compound was treated with dichloromethane/TFA/$H_2O$ (50:45:5; 10 mL) for 45 minutes, concentrated, dissolved in 0.1 M aqueous HCl and washed with toluene. The water phase was concentrated to give 0.21 g (17%) of the title compound. Pos-EI-MS shows M++11 ions supporting the stated structure. HRMS m/z calcd for $C_{16}H_{20}N_8O_2$ (M)⁺356.1709, found 356.1719.

Example 57

1-[2-(4-Cyanophenoxy)ethyl]-3-(1-piperazinyl)-2(1H)-pyrazinone, Maleate

Step 1: tert-Butyl 4-{4-[2-(4-cyanophenoxy)ethyl]-3-oxo-3,4-dihydro-2-pyrazinyl}-1-piperazinecarboxylate.

DEAD (0.520 ml, 3.3 mmol) was added to a slurry of 2-[3-(4-tert-butoxycarbonyl-1-piperazinyl)-pyrazinyloxy]ethanol (1.00 g, 3.08 mmol), 4-cyanophenol (0.381 g, 3.20 mmol) and resin bound triphenylphosphine (1.1 g, 3.3 mmol) in dichloromethane (10 mL) and shaken overnight. The reaction mixture was filtered, concentrated and purified by chromatography on silica gel using toluene/EtOAc (1:1) as eluent to give 0.168 g (13%) of the title compound. $^1$H NMR and MS analyses support the stated structure. HRMS m/z calcd for $C_{22}H_{27}N_5O_4$ (M)$^+$ 425.2063, found 425.2075.

Step 2: 1-[2-(4-Cyanophenoxy)ethyl]-3-(1-piperazinyl)-2(1H)-pyrazinone, Maleate.

tert-Butyl 4-{4-[2-(4-cyanophenoxy)ethyl]-3-oxo-3,4-dihydro-2-pyrazinyl}-1-piperazinecarboxylate (0.145 g, 0.34 mmol; from Step 1) was treated with dichloromethane/TFA/$H_2O$ (50:45:5; 5 mL) for 30 minutes and poured into 5% aqueous NaOH and extracted with diethyl ether. The ether phase was dried and concentrated to give 0.104 g of the free base of the title compound. This material and maleic acid (0.037 g, 0.32 mmol) were dissolved in MeOH and concentrated to give 0.133 g (88%) of the title compound. Pos-EI-MS shows M$^+$+11 ions supporting the stated structure. HRMS m/z calcd for $C_{17}H_{19}N_5O_2$ (M)$^+$ 325.1539, found 325.1531.

Example 58

1-[4-(2,4,5-Trifluorophenoxy)butyl]-3-(1-piperazinyl)-2(1H)-pyrazinone, Trifluoroacetate Step 1: 4-(2,4,5-Trifluoro-phenoxy)butan-1-ol.

To a mixture of 1,4-butanediol (15 g, 0.17 mol) and t-BuOK (8.0 g, 0.071 mol) were added 1,2,4,5-tetrafluorobenzene (5.0 g, 33 mmol) and DMSO (50 g) at 60° C. After being stirred at this temperature for 18 h, toluene (200 mL), water (50 mL) and sodium chloride (10 g) were added to the reaction mixture. The layers were separated and the organic layer was concentrated in vacuo giving the title compound. This material was used directly in the next step.

Step 2: Methanesulfonic acid 4-(2,4,5-trifluoro-phenoxy)butyl ester.

Triethylamine (2.5 mL, 18.2 mmol) was added to a cold (0° C.) solution of a mixture of 4-(2,4,5-trifluorophenoxy)butan-1-ol (2.0 g, 9.1 mmol; from Step 1) and methanesulfonyl chloride (0.77 mL, 10 mmol) in dichloromethane (40 mL). After being stirred for 1 h, water was added and the organic phase isolated, dried and concentrated to give 2.45 g (90%) of the title mesylate as a colorless oil. Its structure was confirmed by $^1$H NMR analysis.

Step 3: tert-Butyl 4-{4-[4-(2,4,5-trifluorophenoxy)butyl]-3-oxo-3,4-dihydro-2-pyrazinyl}-1-piperazinecarboxylate.

A mixture of 3-(4-tert-butoxycarbonyl-1-piperazinyl)-2(1H)-pyrazinone (1.20 g, 4.30 mmol; from Example 48, Step 1) and t-BuOK (730 mg, 6.50 mmol) in THF (10 mL) was stirred for 10 min, and then added to a solution of methanesulfonic acid 4-(2,4,5-trifluoro-phenoxy)butyl ester (1.23 g, 4.3 nmol; from Step 2) in THF (50 mL). After being stirred at room temperature for 1 day, HPLC showed about 30% conversion. After 3 days, the reaction was worked up: water was added, THF was evaporated off and the aqueous mixture was extracted twice with EtOAc, dried and concentrated to yield 2.21 g of the crude product as a yellow oil. HPLC analysis showed a 5/1 ratio between the title product and the isomeric O-alkylated product.* Purification by chromatography on silica gel using EtOAc/hexane (1/2 to 1/1) as eluent gave 870 mg (42%) of the title product as a colorless oil. HPLC purity: 95%. MS m/z 483 (M+H)$^+$. *Assignments were based on NMR analysis.

Step 4: 1-[4-(2,4,5-Trifluorophenoxy)butyl]-3-(1-piperazinyl)-2(1H)-pyrazinone, Trifluoroacetate.

tert-Butyl 4-{4-[4-(2,4,5-trifluorophenoxy)butyl]-3-oxo-3,4-dihydro-2-pyrazinyl}-1-piperazinecarboxylate (830 mg, 1.80 mmol; from Step 3) was N-deprotected by reaction with TFA (4 mL) in dichloromethane (15 mL) over 1.5 h at room temperature. Evaporation of excess TFA and solvent followed by addition of diethyl ether gave, after filtration and washing with ether, the title compound as a light pink solid. Yield: 800 mg (91%), mp 113.4-116.6 (dec). HPLC purity: 100% MS m/z 383 (M+H)$^+$. HRMS m/z calcd for $C_{19}H_{21}F_3N_4O_2$ (M)$^+$ 382.1617, found 382.1622.

Example 59

1-[3-(2,4,5-Trifluorophenoxy)propyl]-3-(1-piperazinyl)-2(1H)-pyrazinone, Trifluoroacetate Step 1: 3-(2,4,5-Trifluoro-phenoxy)propan-1-ol.

To a mixture of 1,3-propanediol (15 g, 0.20 mol) and t-BuOK (8.0 g, 0.071 mol) were added 1,2,4,5-tetrafluorobenzene (5.0 g, 33 mol) and DMSO (50 g) at 60° C. After being stirred at this temperature for 18 h, toluene (200 mL), water (50 mL) and sodium chloride (10 g) were added to the reaction mixture. The layers were separated and the organic layer was concentrated in vacuo to the title compound that was used directly in the next step.

Step 2: Methanesulfonic acid 3-(2,4,5-trifluoro-phenoxy)propyl ester.

Triethylamine (1.36 mL, 9.80 mmol) was added to a cold (0° C.) solution of a mixture of the 3-(2,4,5-trifluorophenoxy)propan-1-ol (1.0 g, 4.9 mmol; from Step 1) and mesyl chloride (0.418 mL, 5.40 mmol) in dichloromethane (20 mL). After being stirred for 1 h, water was added and the organic phase isolated, dried and concentrated to give 1.35 g (97%) of the title mesylate as a colorless oil.

Step 3: tert-Butyl 4-{4-[3-(2,4,5-trifluorophenoxy)propyl]-3-oxo-3,4-dihydro-2-pyrazinyl}-1-piperazinecarboxylate.

A mixture of 3-(4-tert-butoxycarbonyl-1-piperazinyl)-2(1H)-pyrazinone (0.83 g, 3.0 mmol; from Example 48, Step 1) and t-BuOK (497 mg, 4.4 mmol) in THF (5 mL) was stirred for 10 min, and then added to methanesulfonic acid 3-(2,4,5-trifluoro-phenoxy)-propyl ester (0.80 g, 3.0 mmol; from Step 2) in THF (50 mL). After being stirred at room temperature for 1 day, HPLC showed about 20% conversion. After 6 days, the reaction was worked up: water was added, THF was evaporated and the aqueous mixture was extracted twice with EtOAc, dried and concentrated to yield 1.33 g of the crude product as a yellow oil. HPLC analysis showed a 1/1 ratio between the title product and the isomeric O-alkylated product. Purification by chromatography on silica gel using EtOAc/hexane (1/3 to 1/1.7) as eluent gave 427 mg (30%) of the title product as a colorless oil. HPLC purity: 96%. MS m/z 469 (M+H)$^+$.

Step 4: 1-[3-(2,4,5-Trifluorophenoxy)propyl]-3-(1-piperazinyl)-2(1H)-pyrazinone, Trifluoroacetate.

tert-Butyl 4-{4-[3-(2,4,5-trifluorophenoxy)propyl]-3-oxo-3,4-dihydro-2-pyrazinyl}-1-piperazinecarboxylate (395 mg, 0.84 mmol; from Step 3) was N-deprotected by reaction with TFA (2 mL) in dichloromethane (10 mL) over 1.5 h at room temperature. Evaporation of excess TFA and solvent followed by addition of diethyl ether gave, after filtration, washing with ether and drying, the title compound as a light pink solid. Yield: 350 mg (73%); mp. 100.3-100.9 (dec); HPLC purity: 100%; MS m/z 369 (M+H)$^+$. HRMS m/z calcd for $C_{17}H_{19}F_3N_4O_2$ (M)$^+$ 368.1460, found 368.1466.

Example 60

3-[4-(1-Phenylethyl)piperazin-1-yl]-1-[2-(2,4,5-trifluorophenoxy)ethyl]pyrazin-2(1H)-one, Hydrochloride (racemic)

A mixture of 3-(1-piperazinyl)-1-[2-(2,4,5-trifluorophenoxy)ethyl]-2(1H)-pyrazinone (354 mg, 1.00 mmol; from the free base of Example 3), 1-bromo-1-phenylethane (204 mg, 1.10 mmol) and $K_2CO_3$ (276 mg, 2.00 mmol) in acetonitrile (10 mL) was stirred at 30° C. overnight. The reaction mixture was filtered and the filtrate was concentrated in vacuo. The residue was purified on a $SiO_2$ column using dichloromethane/MeOH (95:5) as eluent. The product was isolated as HCl salt. Yield: 0.26 g (50%); HPLC purity: >99%; mp 137-139° C. HRMS calc for $C_{24}H_{25}F_3N_4O_2$ (M)$^+$ 458.1930, found 458.1933.

Example 61

3-[4-(2-Phenoxyethyl)piperazin-1-yl]-1-[2-(2,4,5-trifluorophenoxy)ethyl]pyrazin-2(1H)-one, Hydrochloride The title compound was prepared according to the procedure of Example 60 starting from 3-(1-piperazinyl)-1-[2-(2,4,5-trifluorophenoxy)ethyl]-2(1H)-pyrazinone (0.35 g, 1.0 mmol; from the free base of Example 3) and 2-bromoethyl phenyl ether (0.22 g, 1.1 mmol). Yield 0.14 g (27%). HPLC purity: 99%. HRMS calc for $C_{24}H_{25}F_3N_4O_3$ (M)$^+$ 474.1879, found 474.1887.

Example 62

3-[4-(2-Phenylethyl)piperazin-1-yl-]1-[2-(2,4,5-trifluorophenoxy)ethyl]pyrazin-2(1H)-one, Hydrochloride.

The title compound was prepared according to the procedure of Example 60 starting from 3-(1-piperazinyl)-1-[2-(2,4,5-trifluorophenoxy)ethyl]-2(1H)-pyrazinone (0.71 g, 2.0 mmol; from the free base of Example 3) and (2-bromoethyl)benzene (0.41 g, 2.2 mmol). Yield: 0.20 g (20%). HPLC purity: 96%. HRMS calc for $C_{24}H_{25}F_3N_4O_2$ (M)$^+$ 458.1930, found 458.1928.

Example 63

3-(4-Benzylpiperazin-1-yl)-1-[2-(2,4,5-trifluorophenoxy)ethyl]pyrazin-2(1H)-one hydrochloride The title compound was prepared according to the procedure of Example 60 starting from 3-(1-piperazinyl)-1-[2-(2,4,5-trifluorophenoxy)ethyl]-2(1H)-pyrazinone (0.35 g, 1.0 mmol; from the free base of Example 3) and benzyl bromide (0.19 g, 1.1 mmol) Yield: 0.17 g (35%); HPLC purity: 99%; mp 214-214.5° C. HRMS calc for $C_{23}H_{23}F_3N_4O_2$ (M)$^+$ 444.1773, found 444.1789.

Example 64

3-[(2R)-2-Methylpiperazin-1-yl]-1-[2-(2,4,5-trifluorophenoxy)ethyl]pyrazin-2(1H)-one, Trifluoroacetate To a solution of tert-butyl (3R)-4-[3-(2-hydroxyethoxy)pyrazin-2-yl]-3-methylpiperazine-1-carboxylate (from Example 74; 338 mg, 1.00 mmol), 2,4,5-trifluorophenol (178 mg, 1.2 mmol) and triphenylphosphine (315 mg, 1.20 mmol) in THF (5 mL) was added DEAD (210 mg, 1.2 mmol) and the resulting mixture left stirring at room temperature for 4 h. The mixture was concentrated and the residue put through a silica column using dichloromethane dichloromethane/MeOH (95:5) as eluent. The purified material, the N-t-BOC derivative of the title compound, was dissolved in dichloromethane (5 mL) and TFA (1 mL) was added. The mixture was stirred at room temperature for 60 h, concentrated in vacuo, and the residue purified by preparative HPLC to get 125 mg (25%) of the title product. HPLC purity: 95%. HRMS m/z calc for $C_{17}H_{19}F_3N_4O_2$ (M)$^+$ 368.1460, found 368.1448.

Example 65

1-[2-(4-Allyl-2-methoxyphenoxy)ethyl]-3-piperazin-1-ylpyrazin-2(1H)-one, Maleate*

3-(4-tert-Butoxycarbonyl-1-piperazinyl)-2(1H)-pyrazinone (from Example 48, Step 1; 3.08 g, 11.0 mmol) was dissolved in THF (20 mL). t-BuOK (1.23 g, 11 mmol) was added and the mixture stirred for 10 min at room temperature before adding a solution of 2-(4-allyl-2-methoxy-phenoxy)-ethyl methanesulfonate** (3.15 g, 11 mmol) in THF (15 mL). The resulting mixture was left stirring over the weekend. EtOAc (150 mL) and brine (30 mL) were added and the mixture stirred for a few minutes. The organic layer was dried with $Na_2SO_4$ and concentrated to get an oily residue that was purified on a $SiO_2$ column eluting with dichloromethane→dichloromethane/MeOH (97.5:2.5). The fractions containing the N-T-BOC derivative of the title compound were combined and concentrated. This gave 1.46 g of an oil that was redissolved in dichloromethane (60 mL) and TFA (8 g) was added. After being stirred for 2 h, the mixture was concentrated and the residue dissolved in water, added $Na_2CO_3$ (s) and dichloromethane; stirred for 5 min; separated the dichloromethane phase; dried ($Na_2SO_4$) and concentrated to get a greenish oil (900 mg). This material was purified on a $SiO_2$ column using dichloromethane/MeOH (97.5:2.5→90:10) as eluent. The obtained product was isolated as the maleate salt. Yield: 0.46 g (9%); HPLC purity: 93%; mp 158-160° C.; MS m/z 371 (M+H)$^+$. HRMS m/z calc for $C_{20}H_{26}N_4O_3$ (M)$^+$ 370.2005, found 370.2005.

*This compound, as its trifluoroacetate salt, has been prepared by an alternative method in Example 37. **Prepared according to the general procedure described in Example 76.

Example 66

3-Piperazin-1-yl-1-[2-(3-thienyl)ethyl]pyrazin-2(1H)-one, Maleate

The title compound was prepared according to the procedure of Example 65 starting from 3-(4-tert-butoxycarbonyl-1-piperazinyl)-2(1H)-pyrazinone (2.24 g, 8.0 mmol; from Example 48, Step 1), 2-(3-thienyl)ethyl methanesulfonate* (1.65 g, 8.00 mmol) and t-BuOK (1.35 g, 12.0 mmol). Yield: 0.48 g (20%). HPLC purity: 96%. MS m/z 291 (M+H)$^+$. HRMS m/z calc for $C_{14}H_{18}N_4OS$ (M)$^+$ 290.1201, found 290.1208.
*Prepared according to the procedure of Example 76 and previously reported in J. Am. Chem. Soc. 1987, 109, 1858-1859.

Example 67

3-Piperazin-1-yl-1-[2-(2-thienyl)ethyl]pyrazin-2 (1H)-one, Trifluoroacetate

The title compound was prepared according to the procedure of Example 65 starting from 3-(4-tert-butoxycarbonyl-1-piperazinyl)-2(1H)-pyrazinone (2.24 g, 8.0 mmol; from Example 48, Step 1), 2-(2-thienyl)ethyl methanesulfonate* (1.65 g, 8.00 mmol) and t-BuOK (1.35 g, 12.0 mmol). Yield: 0.62 g (19%). HPLC purity: 96%. MS m/z 291 (M+H)$^+$. HRMS m/z calc for $C_{14}H_{18}N_4OS$ (M)$^+$ 290.1201, found 290.1203.
*Prepared according to the procedure of Example 76 and previously reported in J. Med. Chem. 1989, 32, 1108-1118.

Example 68

1-[2-(1H-Indol-3-yl)ethyl]-3-piperazin-1-ylpyrazin-2 (1H)-one, Trifluoroacetate

The title compound was prepared according to the procedure of Example 65 starting from 3-(4-tert-butoxycarbonyl-1-piperazinyl)-2(1H)-pyrazinone (0.93 g, 3.4 mmol; from Example 48, Step 1), 2-(indol-3-yl) ethyl methanesulphonate* (1.1 g, 3.4 mmol) and t-BuOK (0.38 g, 3.4 mmol). Yield: 22 mg (2%). HPLC purity: 95%. HRMS m/z calc for $C_{18}H_{21}N_5O$ (M)$^+$ 323.1746, found 323.1754.
*Prepared according to the procedure of Example 76.

Example 69

1-[2-(2,3-Dihydro-1,4-benzodioxin-5-yloxy)ethyl]-3-piperazin-1-ylpyrazin-2(1H)-one, Trifluoroacetate The title compound was prepared according to the procedure of Example 65 starting from 3-(4-tert-butoxycarbonyl-1-piperazinyl)-2(1H)-pyrazinone (0.72 g, 2.6 mmol; from Example 48, Step 1), 2-(2,3-dihydro-1,4-benzodioxin-5-yloxy)ethyl methanesulphonate* (0.86 g, 2.6 mmol) and t-BuOK (0.29 g, 2.6 mmol). Yield: 185 mg (15%). HPLC purity: 99%. HRMS m/z calc for $C_{18}H_{22}N_4O_4$ (M)$^+$ 358.1641, found 358.1650.
*Prepared according to the procedure of Example 76. The corresponding alcohol 2-(2,3-dihydro-1,4-benzodioxin-5-yloxy)ethanol was prepared according to the general procedure described in WO 00/76984, Example 91, Step 1.

Example 70

1-[2-(Phenylthio)ethyl]-3-piperazin-1-ylpyrazin-2 (1H)-one, Trifluoroacetate

The title compound was prepared according to the procedure of Example 65 starting from 3-(4-tert-butoxycarbonyl-1-piperazinyl)-2(1H)-pyrazinone (2.41 g, 8.62 mmol; from Example 48, Step 1), 2-phenylsulfanyl-ethyl methanesulfonate* (2.00 g, 8.62 mmol) and t-BuOK (0.97 g, 8.62 mmol). Yield: 80 mg (2%). HPLC purity: 99%. HRMS m/z calc for $C_{16}H_{20}N_4OS$ (M)$^+$ 316.1358, found 316.1357.
*Prepared according to the procedure of Example 76.

Example 71

1-(3-Oxo-3-phenylpropyl)-3-piperazin-1-ylpyrazin-2 (1H)-one, Trifluoroacetate (also known as 4'-(3-Oxo-3-phenyl-propyl)-3,4,5,6-tetrahydro-2H,4'H-[1, 2']bipyrazinyl-3'-one, trifluoroacetate)

The title compound was prepared according to the procedure of Example 65 starting from 3-(4-tert-butoxycarbonyl-1-piperazinyl)-2(1H)-pyrazinone (0.56 g, 2.00 mmol; from Example 48, Step 1), commercially available 3-chloro-1-phenyl-propan-1-one (0.34 g, 2.0 mmol) and t-BuOK (0.22 g, 2.0 mmol). Yield: 0.45 g (52%). HPLC purity: 97%. MS m/z 313 (M+H)$^+$. HRMS m/z calc for $C_{17}H_{20}N_4O_2$ (M)$^+$ 312.1586, found 312.1587.

Example 72

1-[3-(4-Fluorophenyl)-3-oxopropyl]-3-piperazin-1-ylpyrazin-2(1H)-one, Trifluoroacetate (also known as 4'-[3-(4-Fluoro-phenyl)-3-oxo-propyl]-3,4,5,6-tetrahydro-2H,4'H-[1,2']bipyrazinyl-3'-one; trifluoroacetate)

The title compound was prepared according to the procedure of Example 65 starting from 3-(4-tert-butoxycarbonyl-1-piperazinyl)-2(1H)-pyrazinone (0.56 g, 2.00 mmol; from Example 48, Step 1), commercially available 3-chloro-1-(4-fluoro-phenyl)-propan-1-one (0.37 g, 2.0 mmol) and t-BuOK (0.22 g, 2.0 mmol). Yield: 0.14 g (15%). HPLC purity: 98%. MS m/z 331 (M+H)$^+$. HRMS m/z calc for $C_{17}H_{19}FN_4O_2$ (M)$^+$ 330.1492, found 330.1498.

Example 73

Intermediate

2-[3-(4-tert-Butoxycarbonyl-3-methyl-1-piperazinyl)-pyrazinyloxy]ethanol

Step 1. 2-Chloro-3-(3-methylpiperazin-1-yl)pyrazine.
A mixture of 2,3-dichloropyrazine (2.80 g, 18.8 mmol), racemic 2-methylpiperazine (1.88 g, 18.8 mmol) and $K_2CO_3$ (3.90 g, 28.2 mmol) in acetonitrile (25 mL) was heated at 65° C. for 15 h with stirring. The reaction mixture was filtered and concentrated. The crude product was purified by flash chromatography on silica gel using $CHCl_3$/MeOH (15:1) as eluent to give 3.2 g (79%) of the title compound. MS m/z 213 (M+H)$^+$.

Step 2. tert-Butyl 4-(3-chloropyrazin-2-yl)-2-methylpiperazine-1-carboxylate.
Triethylamine (1.82 g, 17.9 mmol) was added to a solution of 2-chloro-3-(3-methylpiperazin-1-yl)pyrazine (3.18 g, 15.0 mmol; from Step 1) in dichloromethane (20 mL) at 0° C. Di-tert-butyl dicarbonate (3.92 g, 17.9 mmol) in dichloromethane (20 mL) was added dropwise and the resulting mixture was stirred at 0° C. for 30 min. The mixture was allowed to warm to room temperature and stirring was continued for a further 15 h. The reaction mixture was washed with water, the organic layer dried over $MgSO_4$, and concentrated in vacuo to give 3.12 g (67%) of the title compound. MS m/z 313 (M+H)$^+$.

Step 3. 2-[3-(4-tert-Butoxycarbonyl-3-methyl-1-piperazinyl)-pyrazinyloxy]-ethanol.
To a mixture of tert-butyl 4-(3-chloropyrazin-2-yl)-2-methylpiperazine-1-carboxylate (3.0 g, 9.6 mmol; from Step 2) in ethylene glycol (10 mL) and dioxane (30 mL) was added t-BuOK (1.18 g, 10.6 mmol). The resulting mixture was stirred at 90° C., under $N_2$, overnight. Water (10 mL) was added to the light brown reaction mixture and extracted with dichloromethane (3×20 mL). The organic layer was dried over $MgSO_4$, filtered, and concentrated in vacuo. The residue was purified by column chromatography using toluene/EtOAc (2:3) as eluent to furnish 3.19 g (98%) of the title compound. HPLC purity: 99%. MS m/z 339 $(M+H)^+$. HRMS m/z calcd for $C_{16}H_{26}N_4O_4 (M)^+$ 338.1954, found 338.1953.

Example 74

Intermediate tert-Butyl (3R)-4-[3-(2-hydroxyethoxy)pyrazin-2-yl]-3-methylpiperazine-1-carboxylate.

A mixture of tert-butyl (3R)-4-(3-chloropyrazin-2-yl)-3-methylpiperazine-1-carboxylate* (35 g, 0.11 mol), ethylene glycol (100 g, 1.61 mol) and t-BuOK (25 g, 0.22 mol) in DMSO (150 g) was stirred at 50° C. for 3 h. After this time, the reaction mixture was partitioned between EtOAc (500 g) and water (500 g) and sodium chloride (20 g) was added. The organic layer was concentrated in vacuo to furnish 32.5 g (87%) of the title product. HPLC purity: 75%. HRMS m/z calcd for $C_{16}H_{26}N_4O_4$ $(M)^+$ 338.1954, found 338.1959.
*Described in WO 00/76984, Example 172, Step 2.

Example 75

Intermediate tert-Butyl 4-[3-(2-hydroxyethoxy)pyrazin-2-yl]-1,4-diazepane-1-carboxylate Step 1: tert-Butyl 4-(3-chloropyrazin-2-yl)-1,4-diazepane-1-carboxylate.

To a stirred mixture of 2,3-dichloropyrazine (1.91 g, 12.8 mmol) and N-t-BOC-homopiperazine, (2.57 g, 12.8 mmol) in acetonitrile (25 mL), was added $K_2CO_3$ (2.65 g, 19.2 mmol). The mixture was heated in an oil bath (65° C.) overnight. The solution was filtered and the solvent evaporated. The oil contained a white precipitate, so this was dissolved in acetonitrile and filtered again. The crude mixture was purified by flash chromatography using toluene/EtOAc (7:3) as eluent. $^1$H NMR analysis supports the stated structure. Yield: 2.13 g (53%). HPLC purity: 97%.

Step 2: tert-Butyl 4-[3-(2-hydroxyethoxy)pyrazin-2-yl]-1,4-diazepane-1-carboxylate.

To a stirred mixture of tert-butyl 4-(3-chloropyrazin-2-yl)-1,4-diazepane-1-carboxylate (2.5 g, 8.0 mmol; from Step 1) in ethylene glycol (8 mL) and dioxane (25 mL), was added t-BuOK (0.99 g, 8.8 mmol). The mixture was heated at 90° C. with condenser, under $N_2$, overnight. Water (10 mL) was added to the light brown mixture and extracted with dichloromethane (3×20 mL). The organic phase was dried over $MgSO_4$. The solution was filtered and the solvent evaporated. The residue was purified by chromatography on silica gel using toluene/EtOAc (2:3) as eluent. $^1$H NMR analysis supports the stated structure. Yield: 1.66 g (61%). HPLC purity: 100%. MS m/z 339 $(M+H)^+$.

Example 76

General procedure for the preparation of the mesylates used in Examples 65-70: The starting alcohol (1 equiv) and triethylamine (2 equiv) were dissolved in dichloromethane; the solution cooled on ice/water; methanesulphonyl chloride (1.5 equiv) was added dropwise under stirring; the mixture stirred at room temperature for 1 h; diluted the mixture with dichloromethane; washed with water; dried with $Na_2SO_4$ and concentrated to get the mesylate. The crude mesylate contains residual triethylamine (up to 0.6 mol equiv).

Preparation of a Pharmaceutical Composition

EXAMPLE

Preparation of tablets

| | Ingredients | mg/tablet |
|---|---|---|
| 1. | Active compound of formula (I) | 10.0 |
| 2. | Cellulose, microcrystalline | 57.0 |
| 3. | Calcium hydrogen phosphate | 15.0 |
| 4. | Sodium starch glycolate | 5.0 |
| 5. | Silicon dioxide, colloidal | 0.25 |
| 6. | Magnesium stearate | 0.75 |

The active ingredient 1 is mixed with ingredients 2, 3, 4 and 5 for about 10 minutes. The magnesium stearate is then added, and the resultant mixture is mixed for about 5 minutes and compressed into tablet form with or without film-coating.

Pharmacological Methods

The ability of a compound of the invention to bind or act at specific 5-HT receptor subtypes can be determined using in vitro and in vivo assays known in the art. The biological activity of compounds prepared in the Examples was tested using different tests.

Affinity assay

The 5-$HT_{2A}$ receptor affinity of compounds in the Examples was determined in competition experiments, where the ability of each compound in serial dilution to displace $^3$H-labeled lysergic diethyl amide (LSD), bound to membranes prepared from a transfected CHO cell line stably expressing the human 5-$HT_{2A}$ receptor protein, was measured after rapid filtration through glass fiber filters. Non-specific binding was defined using mianserin (5 μM). The 5-$HT_{2A}$ receptor affinity values are expressed as $K_i$ values. Results obtained for exemplary compounds of the invention are illustrated in Table 1 below. The $K_i$ values for the compounds towards the human 5-$HT_{2A}$ receptor were in the range 0.1-1500 nM.

TABLE 1

Human 5-$HT_{2A}$ receptor Affinity

| Compound | $K_i$ (nM) |
|---|---|
| Example 2 | 152 |
| Example 3 | 2.2 |
| Example 11 | 2.5 |
| Example 13 | 29 |
| Example 23 | 13 |
| Example 24 | 3.6 |
| Example 29 | 8 |

TABLE 1-continued

| Human 5-HT$_{2A}$ receptor Affinity | |
|---|---|
| Compound | K$_i$ (nM) |
| Example 31 | 4.4 |
| Example 62 | 0.15 |
| Example 63 | 1.4 |

In Vitro Functional Assay

The antagonist activity at the 5-HT$_{2A}$ receptor of the compounds in the Examples of the present invention was judged from their inability to mobilise intracellular calcium in transfected CHO cells, stably expressing the human 5-HT$_{2A}$ receptor protein, using the calcium-chelating fluorescent dye FLUO-3 (Sigma, St. Louis, Mo., U.S.A.) at a substrate concentration of 1 μM. Additionally, the antagonist activity at the 5-HT$_{2A}$ receptor of the said compounds could be verified by their ability to inhibit 5-HT-induced calcium release in transfected CHO cells, stably expressing the human 5-HT$_{2A}$ receptor protein, using cumulative dose-response techniques. From these experiments, the apparent functional inhibitory constant K$_b$ could be estimated.

The invention claimed is:

1. A compound of the general formula (I):

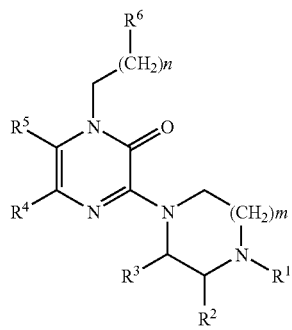

(I)

wherein m is 1 or 2;

n is 0, 1, 2, 3 or 4;

R$^1$ is H, C$_{1-6}$-alkyl, aryl-C$_1$-C$_3$-alkyl, heteroaryl-C$_1$-C$_3$-alkyl, 2-hydroxyethyl, methoxy-C$_2$-C$_4$-alkyl, C$_1$-C$_4$-alkoxycarbonyl, aryloxy-C$_2$-C$_3$-alkyl, or heteroaryloxy-C$_2$-C$_3$-alkyl; wherein any aryl or heteroaryl residue may be substituted with C$_{1-4}$-alkyl, C$_{1-4}$-alkoxy, C$_{1-4}$-alkylthio, halogen, trifluoromethyl, trifluoromethoxy or cyano;

R$^2$ and R$^3$ each, independently, represent H or CH$_3$;

R$^4$ and R$^5$ each, independently, represent H, halogen, methyl, or together with the ring, to which carbon atoms they are attached, form a 1H-quinoxalin-2-one nucleus; and R$^6$ represents aryloxy, heteroaryloxy, arylthio, heteroarylthio, aryl-NH, heteroaryl-NH, aryl, arylcarbonyl, heteroaryl, or heteroarylcarbonyl; wherein any aryl or heteroaryl residue, alone or as part of another group, may be unsubstituted or substituted with one, two, three, four or five substituents, independently selected from aryl, aryl-C$_{1-2}$-alkyl, arylcarbonyl, heteroaryl, heteroaryl-C$_{1-2}$-alkyl, heteroarylcarbonyl, aryloxy, heteroaryloxy, arylthio, heteroarylthio, arylamino, heteroarylamino, C$_{3-6}$-cycloalkyl, C$_{3-6}$-cycloalkyloxy, C$_{3-6}$-cycloalkylcarbonyl, C$_{1-6}$-alkyl, C$_{2-6}$-alkanoyl, C$_{2-6}$-alkynyl, C$_{2-6}$-alkenyl, or fluoro-C$_{2-4}$-alkyloxy, halogen, trifluoromethyl, nitro, cyano, trifluoromethoxy, trifluoromethylthio, C$_{1-6}$-alkoxy, C$_{1-6}$-alkylthio, C$_{1-6}$-alkylamino, C$_{1-4}$-dialkylamino, hydroxy or oxo; wherein any aryl or heteroaryl residue as substituents on aryl or heteroaryl, alone or as part of another group, in turn may be substituted in one or more positions, independently of each other, by C$_{1-4}$-alkyl, C$_{1-4}$-alkoxy, C$_{1-4}$-alkylthio, halogen, trifluoromethyl, trifluoromethoxy or cyano;

and pharmaceutically acceptable salts, hydrates, geometrical isomers, tautomers, optical isomers, or N-oxides thereof, with the provisos that:

R$^2$ and R$^3$ are not both CH$_3$;

when n=1 and R$^1$, R$^2$, R$^4$ and R$^5$ are H and R$^3$ is H or CH$_3$, then R$^6$ is not 3-pyridyloxy, 6-methyl-2-nitro-3-pyridyloxy, or 2-chloro-3-pyridyloxy;

when n=0, then R$^6$ is not aryloxy, heteroaryloxy, arylthio, heteroarylthio, aryl-NH or heteroaryl-NH; and the compound of formula (I) is not 1-benzyl-3-(4-methyl-piperazin-1-yl)-1H-quinoxalin-2-one.

2. The compound according to claim 1, wherein any aryl or heteroaryl residue, alone or as part of another group, is substituted with one or two non-halogen substituents.

3. The compound according to claim 1, wherein any aryl or heteroaryl residue, alone or as part of another group, is substituted with at least one halogen substituent.

4. The compound according to claim 1 or 2, wherein any aryl or heteroaryl residue that is a substituent on another aryl or heteroaryl, alone or as part of another group, in turn is substituted in one position.

5. The compound according to claim 1, wherein n=1;

R$^1$, R$^2$, R$^3$, R$^4$ and R$^5$ each are H; and

R$^6$ is phenoxy, where the phenyl ring of the said phenoxy group may be unsubstituted or substituted with one, two, three, four or five substituents.

6. The compound according to claim 5, wherein the phenyl ring of R$^6$ is substituted with one, two, three, four or five substituents independently selected from halogen, 2-propenyl, C$_1$-C$_6$-alkyl, C$_1$-C$_6$-alkoxy, trifluoromethyl, phenyl, phenoxy, benzoyl, and C$_{3-6}$-cycloalkyl;

wherein the phenyl, phenoxy or benzoyl substituent in turn may be unsubstituted or substituted in one or more positions, independently of each other, by C$_{1-4}$-alkyl, C$_{1-4}$-alkoxy, C$_{1-4}$-alkylthio, halogen, trifluoromethyl, trifluoromethoxy or cyano.

7. The compound according to claim 6, wherein the phenyl ring of R$^6$ is substituted with one or two non-halogen substituents.

8. The compound according to claim 6, wherein the halogen substituent is fluorine.

9. The compound according to claim 1, wherein n=1;

R$^1$ is methoxy-C$_2$-C$_4$-alkyl or straight-chained C$_1$-C$_4$-alkyl;

R$^2$, R$^3$, R$^4$ and R$^5$ each are H; and

R$^6$ is 2,4,5-trifluorophenoxy.

10. The compound according to claim 1, wherein
n=1;
R¹, R², R³, R⁴ and R⁵ each are H; and
R⁶ is 2-oxo-1,3-benzoxathiol-5-yloxy.

11. The compound according to claim 1 wherein
n=0;
R¹, R², R³, R⁴ and R⁵ each are H; and
R⁶ is phenyl, where the said phenyl may be substituted with halogen, in one, two, three, four or five positions.

12. The compound according to claim 11 wherein the halogen is fluorine.

13. The compound according claim 1, which is:
- 1-[2-(2-fluoro-4-nitrophenoxy)ethyl]-3-(1piperazinyl)-2(1H)-pyrazinone,
- 1-{2-[(2-oxo-2H-chromen-7-yl)oxy]ethyl}-3-(1-piperazinyl)-2(1H)-pyrazinone,
- 3-(1-piperazinyl)-1-[2-(2,4,5-trifluorophenoxy)ethyl]-2(1H)-pyrazinone,
- 3-(1-piperazinyl)-1-[2-(2,3,5,6-tetrafluorophenoxy)ethyl]-2(1H)-pyrazinone,
- 1-[2-(2,3,4,5,6-pentafluorophenoxy)ethyl]-3-(1-piperazinyl)-2(1H)-pyrazinone,
- 1-[2-(4-chloro-2-fluorophenoxy)ethyl]-3-(1-piperazinyl)-2(1H)-pyrazinone,
- 1-[2-(3-cyanophenoxy)ethyl]-3-(1-piperazinyl)-2(1H)-pyrazinone,
- 1-[2-(4-cyclopentylphenoxy)ethyl]-3-(1-piperazinyl)-2(1H)-pyrazinone,
- 1-[2-(1,2-benzisoxazol-3-yloxy)ethyl]-3-(1-piperazinyl)-2(1H)-pyrazinone,
- 1-[2-(3-methoxyphenoxy)ethyl]-3-(1-piperazinyl)-2(1H)-pyrazinone,
- 1-[2-(3-n-butyloxyphenoxy)ethyl]-3-(1-piperazinyl)-2(1H)-pyrazinone,
- 1-[2-([1,1'-biphenyl]-3-yloxy)ethyl]-3-(1-piperazinyl)-2(1H)-pyrazinone,
- 3-(1-piperazinyl)-1-[2-(2,3,4-trifluorophenoxy)ethyl]-2(1H)-pyrazinone,
- 1-[2-(2,3-dichlorophenoxy)ethyl]-3-(1-piperazinyl)-2(1H)-pyrazinone,
- 1-[2-(1,3-benzodioxol-5-yloxy)ethyl]-3-(1-piperazinyl)-2(1H)-pyrazinone,
- 1-[2-(2,4-difluorophenoxy)ethyl]-3-(1-piperazinyl)-2(1H)-pyrazinone,
- 1-{2-[(2-oxo-1,3-benzoxathiol-5-yl)oxy]ethyl}-3-(1-piperazinyl)-2(1H)-pyrazinone,
- 1-[2-(3-hydroxyphenoxy)ethyl]-3-(1-piperazinyl)-2(1H)-pyrazinone,
- 3-(1-piperazinyl)-1-[2-(6-quinoxalinyloxy)ethyl]-2(1H)-pyrazinone,
- 1-{2-[3-(N,N-dimethylamino)phenoxy]ethyl}-3-(1-piperazinyl)-pyrazin-2(1H)-one,
- 3-(1-piperazinyl)-1-{2-[3-(trifluoromethyl)phenoxy]ethyl}-2(1H)-pyrazinone,
- 1-[2-(3-fluorophenoxy)ethyl]-3-(1-piperazinyl)-2(1H)-pyrazinone,
- 1-[2-(3-nitrophenoxy)ethyl]-3-(1-piperazinyl)-2(1H)-pyrazinone,
- 1-[2-(3-benzoylphenoxy)ethyl]-3-(1-piperazinyl)-2(1H)-pyrazinone,
- 1-[2-(3,5-difluorophenoxy)ethyl]-3-(1-piperazinyl)-2(1H)-pyrazinone,
- 1-[2-(phenoxy)ethyl]-3-(1-piperazinyl)-2(1H)-pyrazinone,
- 1-[2-(2,6-difluorophenoxy)ethyl]-3-(1-piperazinyl)-2(1H)-pyrazinone,
- 1-[2-(2-cyanophenoxy)ethyl]-3-(1-piperazinyl)-2(1H)-pyrazinone,
- 1-[2-(4-trifluoromethylphenoxy)ethyl]-3-(1-piperazinyl)-2(1H)-pyrazinone,
- 1-[2-(4-bromophenoxy)ethyl]-3-(1-piperazinyl)-2(1H)-pyrazinone,
- 1-[2-{4-phenoxy-(phenoxy)}ethyl]-3-(1-piperazinyl)-2(1H)-pyrazinone,
- 1-[2-(4-fluorophenoxy)ethyl]-3-(1-piperazinyl)-2(1H)-pyrazinone,
- 1-[2-(4-isopropylphenoxy)ethyl]-3-(1-piperazinyl)-2(1H)-pyrazinone,
- 1-[2-(2,4,5-trichlorophenoxy)ethyl]-3-(1-piperazinyl)-2(1H)-pyrazinone,
- 1-[2-(2-methylthiophenoxy)ethyl]-3-(1-piperazinyl)-2(1H)-pyrazinone,
- 1-[2-(3-methoxyphenylthio)ethyl]-3-(1-piperazinyl)-2(1H)-pyrazinone,
- 1-[2-{(4-allyl-2-methoxy)phenoxy}ethyl]-3-(1-piperazinyl)-2(1H)-pyrazinone,
- 1-[2-(5,6,7,8-tetrahydro-naphthalen-2-yloxy)ethyl]-3-(1-piperazinyl)-2(1H)-pyrazinone,
- 1-[2-(2,6-difluorophenoxy)ethyl]-3-(3-methyl-1-piperazinyl)-2(1H)-pyrazinone,
- 1-[2-(4-trifluoromethylphenoxy)ethyl]-3-(3-methyl-1-piperazinyl)-2(1H)-pyrazinone,
- 1-[2-(4-bromophenoxy)ethyl]-3-(3-methyl-1-piperazinyl)-2(1H)-pyrazinone,
- 1-[2-(phenoxy)ethyl]-3-(3-methyl-1-piperazinyl)-2(1H)-pyrazinone,
- 1-[2-(2,4,5-trifluorophenoxy)ethyl]-3-(3-methyl-1-piperazinyl)-2(1H)-pyrazinone,
- 1-[2-(2,4,5-trifluorophenoxy)ethyl]-3-(1,4-diazepan-1-yl)-2(1H)-pyrazinone,
- 1-[2-(4-fluorophenoxy)ethyl]-3-(1,4-diazepan-1-yl)-2(1H)-pyrazinone,
- 1-[2-(4-isopropylphenoxy)ethyl]-3-(1,4-diazepan-1-yl)-2(1H)-pyrazinone,
- 1-[2-(2-methylthiophenoxy)ethyl]-3-(1,4-diazepan-1-yl)-2(1H)-pyrazinone,
- 1-(2,4,5-trifluorobenzyl)-3-(1-piperazinyl)-2(1H)-pyrazinone,
- 1-[3-(2,4,5-trifluorophenyl)propyl]-3-(1-piperazinyl)-2(1H)-pyrazinone,
- 1-(2,3-dihydro-benzo[1,4]dioxin-2-ylmethyl)-3-(1-piperazinyl)-2(1H)-pyrazinone,
- 3-piperazin-1-yl-1 [2-(2,4,5-trifluoro-phenoxy)-ethyl]-1H-quinoxalin-2-one,
- 1-[2-(2,4,5-trifluorophenoxy)ethyl]-3-(4-n-butyl-1-piperazinyl)-2(1H)-pyrazinone,
- 1-[2-(2,4,5-trifluorophenoxy)ethyl]-3-[4-(2-methoxy-ethyl)-1-piperazinyl]-2(1H)-pyrazinone,
- 1-[2-(2,4,5-trifluorophenoxy)ethyl]-3-(4-methyl-1-piperazinyl)-2(1H)-pyrazinone,
- 1 [2-(2,4,5-trifluorophenoxy)ethyl]-3-(4-isopropyl-1-piperazinyl)-2(1H)-pyrazinone,
- 1-{2-[(5-methyl[1,2,4]triazolo[1,5-a]pyrimidin-7-yl)oxy]ethyl}-3-(1-piperazinyl)-2(1 H)-pyrazinone,
- 1-[2-(4-Cyanophenoxy)ethyl]-3-(1-piperazinyl)-2(1H)-pyrazinone,
- 1-[4-(2,4,5-trifluorophenoxy)butyl]-3-(1-piperazinyl)-2(1H)-pyrazinone,
- 1-[3-(2,4,5-trifluorophenoxy)propyl]-3-(1-piperazinyl)-2(1H)-pyrazinone,
- 3-[4-(1-phenylethyl)piperazin-1-yl]-1-[2-(2,4,5-trifluorophenoxy)ethyl]-pyrazin-2(1H)-one, 3-[4-(2-phenoxyethyl)piperazin-1-yl]-1-[2-(2,4,5-trifluorophenoxy)ethyl]-pyrazin-2(1H)-one,
3-[4-(2-Phenylethyl)piperazin-1-yl]-1-[2-(2,4,5-trifluorophenoxy)ethyl]pyrazin-2(1H)-one, hydrochloride,
3-(4-Benzylpiperazin-1-yl)-1-[2-(2,4,5-trifluorophenoxy)ethyl]pyrazin-2(1H)-one hydrochloride,
3-[(2R)-2-methylpiperazin-1-yl]-1-[2-(2,4,5-trifluorophenoxy)ethyl]-pyrazin-2(1H)-one,
3-piperazin-1-yl-1-[2-(3-thienyl)ethyl]pyrazin-2(1H)-one,
3-piperazin-1-yl-1-[2-(2-thienyl)ethyl]pyrazin-2(1H)-one,
1-[2-(1H-indol-3-yl)ethyl]-3-piperazin-1-ylpyrazin-2(1H)-one,
1-[2-(2,3-dihydro-1,4-benzodioxin-5-yloxy)ethyl]-3-piperazin-1-ylpyrazin-2(1H)-one,
1-[2-(phenylthio)ethyl]-3-piperazin-1-ylpyrazin-2(1H)-one,
1-(3-oxo-3-phenylpropyl)-3-piperazin-1-ylpyrazin-2(1H)-one, or
1-[3-(4-fluorophenyl)-3-oxopropyl]-3-piperazin-1-ylpyrazin-2(1H)-one, and their pharmacologically acceptable salts and hydrates.

14. A pharmaceutical composition comprising a compound according to claim 1 as an active ingredient, together with a pharmaceutically acceptable carrier.

15. A method for the treatment of a disorder or medical condition selected from angina; Raynaud's phenomenon; intermittent claudication; coronary or peripheral vasospasms; hypertension; schizophrenia; obsessive-compulsive disorder; attention deficit hyperactivity disorder (ADHD); anxiety disorders; depression disorders substance abuse; extrapyramidal symptoms; menopausal and post-menopausal hot flushes; premenstrual syndrome; bronchoconstriction disorders; or eating disorders, the method comprising administering to a subject in need thereof a therapeutically effective amount of a compound according to claim 1.

16. A method for the treatment of neuroleptic drug-induced extrapyramidalsy symptoms, the method comprising administering to a subject in need thereof a therapeutically effective amount of a compound according to claim 1.

17. The method according to claim 15 wherein the eating disorder is binge eating disorders, anorexia nervosa or bulimia.

18. A method of making a compound of formula (I) according to claim 1,
wherein $R^6$ is selected from aryloxy, heteroaryloxy, arylthio, heteroarylthio, aryl-NH, or heteroaryl-NH,
by reacting a compound of the following formula (II):

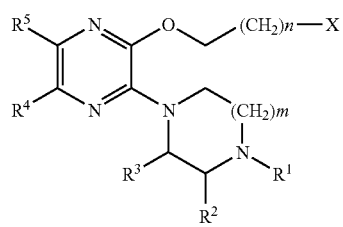

(II)

wherein
m is 1 or 2;
n is 1 or 2;
X is OH;

$R^1$ is H, $C_{1-6}$-alkyl, aryl-$C_1$-$C_3$-alkyl, heteroaryl-$C_1$-$C_3$-alkyl, 2-hydroxyethyl, methoxy-$C_2$-$C_4$-alkyl, $C_1$-$C_4$-alkoxycarbonyl, aryloxy-$C_2$-$C_3$-alkyl, or heteroaryloxy-$C_2$-$C_3$-alkyl; wherein
any aryl or heteroaryl residue may be substituted with $C_{1-4}$-alkyl, $C_{1-4}$-alkoxy, $C_{1-4}$-alkylthio, halogen, trifluoromethyl, trifluoromethoxy or cyano;
$R^2$ and $R^3$ each, independently, represent H or $CH_3$; and
$R^4$ and $R^5$ each, independently, represent H, halogen, methyl, or together with the ring, to which carbon atoms they are attached, form a 1H-quinoxalin-2-one nucleus;
with an optionally substituted phenol or thiophenol; in a solvent.

19. A method according to claim 18 for the preparation of compounds of formula (I) where $R^1$ is H, wherein $R^1$ in the corresponding intermediate of formula (II) is a protecting group selected from tert-butoxycarbonyl (t-BOC) or trityl.

20. A method according to any one of claims 18 or 19, wherein the intermediate of formula (II) is selected from:
2-[3-(4-tert-butoxycarbonyl-3-methyl-1-piperazinyl)-pyrazinyloxy]ethanol;
tert-Butyl (3R)-4-[3-(2-hydroxyethoxy)pyrazin-2-yl]-3-methylpiperazine-1-carboxylate; and
tert-Butyl 4-[3-(2-hydroxyethoxy)pyrazin-2-yl]-1,4-diazepane-1-carboxylate.

21. A method of preparing a compound of formula (I) according to claim 1,
wherein $R^6$ is selected from aryloxy, heteroaryloxy, arylthio, heteroarylthio, aryl-NH,
heteroaryl-NH, aryl, arylcarbonyl, heteroaryl, or heteroarylcarbonyl,
by reacting a compound of the following formula (IV),

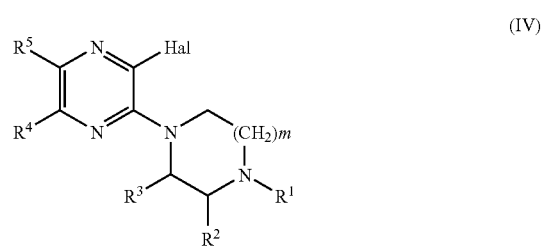

(IV)

wherein
m is 1 or 2;
Hal is halogen;
$R^1$ is H, $C_{1-6}$-alkyl, aryl-$C_1$-$C_3$-alkyl, heteroaryl-$C_1$-$C_3$-alkyl, 2-hydroxyethyl, methoxy-$C_2$-$C_4$-alkyl, $C_1$-$C_4$-alkoxycarbonyl, aryloxy-$C_2$-$C_3$-alkyl, or heteroaryloxy-$C_2$-$C_3$-alkyl; wherein
any aryl or heteroaryl residue may be substituted with $C_{1-4}$-alkyl, $C_{1-4}$-alkoxy, $C_{1-4}$-alkylthio, halogen, trifluoromethyl, trifluoromethoxy or cyano;
$R^2$ and $R^3$ each, independently, represent H or $CH_3$; and
$R^4$ and $R^5$ each, independently, represent H, halogen, methyl, or together with the ring, to which carbon atoms they are attached, form a 1H-quinoxalin-2-one nucleus;
with an alkali metal or alkaline earth metal basic salt, in aqueous media, at 25 to 150° C., to produce a compound of formula (V),

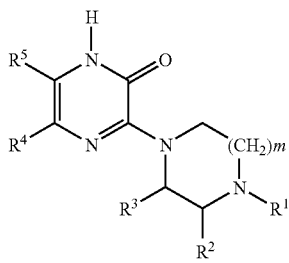

(V)

wherein
m is 1 or 2;
$R^1$ is H or $C_{1-6}$-alkyl, aryl-$C_1$-$C_3$-alkyl, heteroaryl-$C_1$-$C_3$-alkyl, 2-hydroxyethyl, methoxy-$C_2$-$C_4$-alkyl, $C_1$-$C_4$-alkoxycarbonyl, aryloxy-$C_2$-$C_3$-alkyl, or heteroaryloxy-$C_2$-$C_3$-alkyl; wherein
any aryl or heteroaryl residue may be substituted with $C_{1-4}$-alkyl, $C_{1-4}$-alkoxy, $C_{1-4}$-alkylthio, halogen, trifluoromethyl, trifluoromethoxy or cyano;
$R^2$ and $R^3$ each, independently, represent H or $CH_3$; and
$R^4$ and $R^5$ each, independently, represent H, halogen, methyl, or together with the ring, to which carbon atoms they are attached, form a 1H-quinoxalin-2-one nucleus;
followed by N-alkylation of the compound of formula (V) by reaction with a compound of formula (VI),

wherein
n is 0, 1, 2, 3 or 4;
Y is a leaving group; and
$R^6$ represents aryloxy, heteroaryloxy, arylthio, heteroarylthio, aryl-NH, heteroaryl-NH, aryl, arylcarbonyl, heteroaryl, or heteroarylcarbonyl; and
wherein any aryl or heteroaryl residue, alone or as part of another group, may be unsubstituted or substituted. Where substituted, one, two, three, four or five substituents may be present, preferably one or two for non-halogen substituents, and are independently selected from aryl, aryl-$C_{1-2}$-alkyl, arylcarbonyl, heteroaryl, heteroaryl-$C_{1-2}$-alkyl, heteroarylcarbonyl, aryloxy, heteroaryloxy, arylthio, heteroarylthio, arylamino, heteroarylamino, $C_{3-6}$-cycloalkyl, $C_{3-6}$-cycloalkyloxy, $C_{3-6}$-cycloalkylcarbonyl, $C_{1-6}$-alkyl, $C_{2-6}$-alkanoyl, $C_{2-6}$-alkynyl, $C_{2-6}$-alkenyl, or fluoro-$C_{2-4}$-alkyloxy, halogen, trifluoromethyl, nitro, cyano, trifluoromethoxy, trifluoromethylthio, $C_{1-6}$-alkoxy, $C_{1-6}$-alkylthio, $C_{1-6}$-alkylamino, $C_{1-4}$-dialkylamino, hydroxy or oxo;

wherein any aryl or heteroaryl residue as substituents on aryl or heteroaryl, alone or as part of another group, in turn may be substituted in one or more positions, preferably one, independently of each other by $C_{1-4}$-alkyl, $C_{1-4}$-alkoxy, $C_{1-4}$-alkylthio, halogen, trifluoromethyl, trifluoromethoxy, or cyano;
in the presence of a base in a suitable solvent.

22. A method according to claim 21 for the preparation of compounds of formula (I) where $R^1$ is H, wherein $R^1$ in the corresponding intermediate of formula (V) is a protecting group selected from tert-butoxycarbonyl (t-BOC) or trityl.

23. The method according to claim 19 wherein $R^1$ in the corresponding intermediate of formula (II) is tert-butoxycarbonyl (t-BOC).

24. The method according to claim 22 wherein $R^1$ in the corresponding intermediate of formula (V) is tert-butoxycarbonyl (t-BOC).

25. The compound according to claim 1 where in the compound of formula (I)
n=1;
$R^1$ is aryl-C1-C3-alkyl;
$R^2$, $R^3$, $R^4$ and $R^5$ are each H; and
$R^6$ is 2,4,5-trifluorophenoxy.

26. A method for the treatment of glaucoma, the method comprising administering to a subject in need thereof a therapeutically effective amount of a compound according to claim 1.

27. The method of claim 26, wherein the glaucoma is normal tension glaucoma.

28. A method for the treatment of urinary incontinence, the method comprising administering to a subject in need thereof a therapeutically effective amount of a compound according to claim 1.

29. The method of claim 28, wherein the urinary incontinence is urinary incontinence with co-existing diabetes.

30. The method of claim 15, wherein the depression disorder is depression with coexisting diabetes.

31. A method for the treatment of insomnia or sleep apnea, the method comprising administering to a subject in need thereof a therapeutically effective amount of a compound according to claim 1.

32. A method for the treatment of thrombosis, the method comprising administering to a subject in need thereof a therapeutically effective amount of a compound according to claim 1.

33. A method for the treatment of diabetic complications selected from nephropathy, neuropathy and retinopathy, the method comprising administering to a subject in need thereof a therapeutically effective amount of a compound according to claim 1.

* * * * *